(12) United States Patent
Araki et al.

(10) Patent No.: US 8,637,277 B2
(45) Date of Patent: Jan. 28, 2014

(54) METHOD FOR PRODUCING 3-MERCAPTOPROPIONIC ACID OR SALT THEREOF

(75) Inventors: Tadashi Araki, Chosei-gun (JP); Masayuki Furuya, Arao (JP); Hidetoshi Hayashi, Omuta (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 0 days.

(21) Appl. No.: 13/318,029

(22) PCT Filed: Apr. 30, 2010

(86) PCT No.: PCT/JP2010/003097
§ 371 (c)(1),
(2), (4) Date: Oct. 28, 2011

(87) PCT Pub. No.: WO2010/125829
PCT Pub. Date: Nov. 4, 2010

(65) Prior Publication Data
US 2012/0040418 A1 Feb. 16, 2012

(30) Foreign Application Priority Data
Apr. 30, 2009 (JP) .................................. 2009-111257

(51) Int. Cl.
*C12P 11/00* (2006.01)
*C12P 7/40* (2006.01)
*C12N 9/80* (2006.01)
*C12N 9/88* (2006.01)

(52) U.S. Cl.
USPC ............. 435/130; 435/228; 435/232; 435/41; 435/136

(58) Field of Classification Search
USPC .......................... 435/130, 228, 232, 41, 136
See application file for complete search history.

(56) References Cited

U.S. PATENT DOCUMENTS

| | | | |
|---|---|---|---|
| 5,130,235 A * | 7/1992 | Beppu et al. ................. | 435/227 |
| 5,702,930 A * | 12/1997 | Kiener et al. ................. | 435/122 |
| 5,932,454 A | 8/1999 | Matsuoka et al. | |
| 6,342,571 B1 | 1/2002 | Smith et al. | |
| 2007/0009985 A1 | 1/2007 | Yamaki et al. | |
| 2007/0172933 A1 | 7/2007 | Egorova et al. | |

FOREIGN PATENT DOCUMENTS

| | | | |
|---|---|---|---|
| CN | 1793117 A | | 6/2006 |
| CN | 101125827 A | | 2/2008 |
| JP | 58-201992 A | | 11/1983 |
| JP | 61-151163 A | | 7/1986 |
| JP | 04145063 A | * | 5/1992 |
| JP | 04-305563 A | | 10/1992 |
| JP | 10-179183 A | | 7/1998 |
| JP | 2001-187778 A | | 7/2001 |
| JP | 2004-194588 A | | 7/2004 |
| JP | 2004-254690 A | | 9/2004 |
| JP | 2005-176639 A | | 7/2005 |
| JP | 2006-340630 A | | 12/2006 |
| JP | 2008-022706 A | | 2/2008 |

OTHER PUBLICATIONS

Nagata T. et al. , JP 04145063 A (May 1992)—English abstract.*
International Search Report (PCT/ISA/210) issued on Jul. 27, 2010, by Japanese Patent Office as the International Searching Authority for International Application No. PCT/JP2010/003097.
L. Ciskanik et al., "Purification and Characterization of an Enantioselective Amidase from *Pseudomonas chlororaphis* B23," Applied and Environmental Microbiology, Mar. 1995 (month unknown), pp. 998-1003, vol. 61. No. 3.
M. Nawaz et al., "Degradation of Organic Cyanides by *Pseudomonas aeruginosa*," Applied Biochemistry and Biotechnology, 1991 (month unknown), pp. 865-875, vol. 28/29.
J. Song et al., "Kinetics of UV curable alkyl 3-mercaptopropionate-vinyl silizane," Front Chem. Eng. China, 2008 (month unknown), pp. 390-395, vol. 2, No. 4.
N. Klempier et al., "Selective Transformation of Nitriles into Amides and Carboxylic Acids by an Immobilized Nitrilase," Tetrahedon Letters, 1991 (month unknown), pp. 341-344, vol. 32, No. 3.
C. O'Reilly et al., "The nitrilase family of CN hydrolysing enzymes—a comparative study," Journal of Applied Microbiology, 2003 (month unknown), pp. 1161-1174, vol. 95.
D. Fournand et al., "Aliphatic and enantioselective amidases: from hydrolysis to acyl transfer activity," Journal of Applied Microbiology, 2001 (month unknown), pp. 381-393, vol. 91.
M. Maestracci et al., "Activity and regulation of an amidase (acylamide amodohydrolase, EC 3.5.1.4) with a wide substrate spectrum from a *Brevibacterium* sp.," Archives of Microbiology, 1984 (month unknown), pp. 315-320, vol. 138.
Nagasawa et al., Nitrile hydratase of *Pseudomonas chlororaphis* B23, Purification and characterization, Eur. J. Biochem. 162, pp. 691-698 (1987).
Xu Jiang, et al., Syntthesis of β-mercaptopropionic Acid, Fine Chemical Intermediates, Jun. 2004, pp. 48-49, vol. 35, No. 3, English Abstract only.
Song Jiale, et al., On Kinetics of Alkyl 3-Mercaptopropionate-Vinyl Silizane Copolymerized by UV, Journal of Northwestern Polytechnical University, February English abstract only, pp. 30-34, vol. 26, No. 1, (2008).

\* cited by examiner

*Primary Examiner* — Chih-Min Kam
(74) *Attorney, Agent, or Firm* — Buchanan Ingersoll & Rooney PC

(57) ABSTRACT

The present invention provides is a method for producing 3-mercaptopropionic acid from 3-mercaptopropionamide or a salt thereof with the use of an amidase. The method enables the production of 3-mercaptopropionic acid on an industrial scale through an enzymatic reaction.

12 Claims, 1 Drawing Sheet

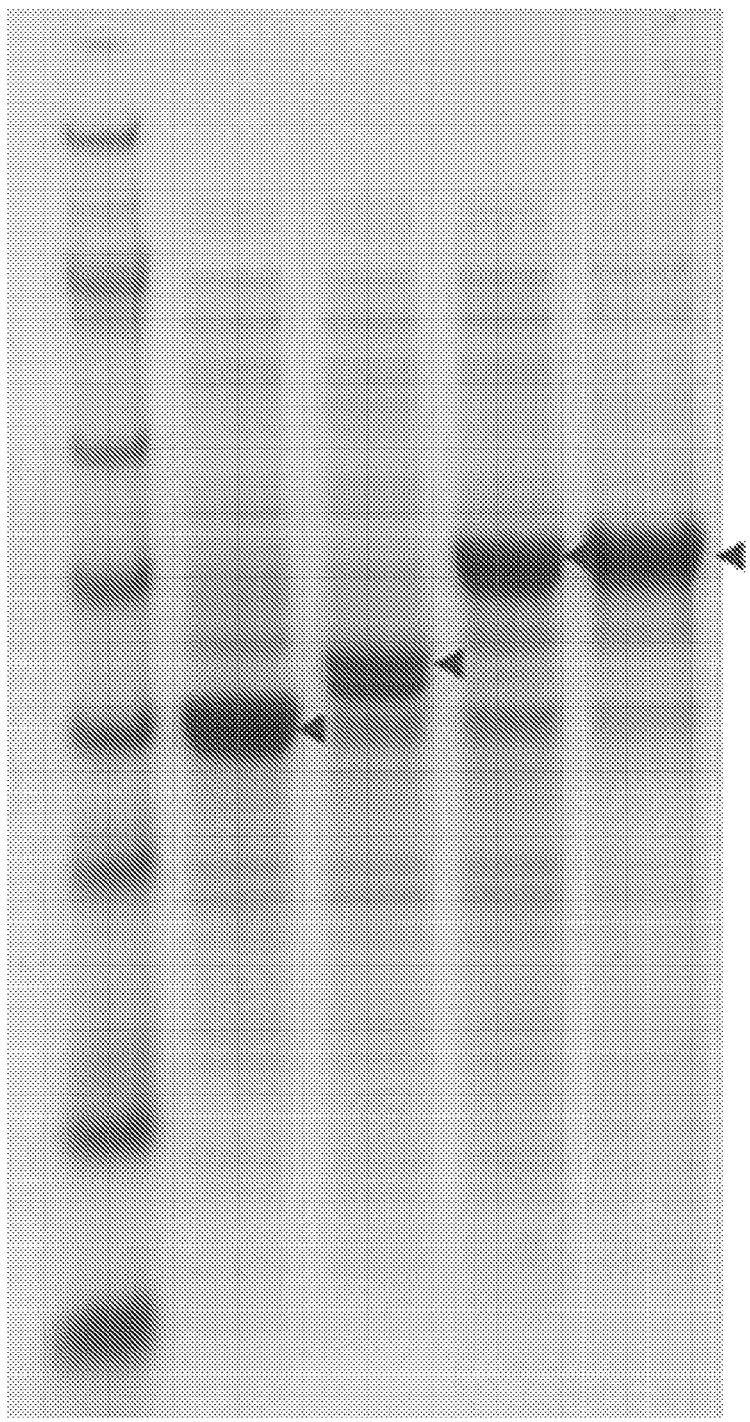

SEQUENCE LISTING

```
<160> NUMBER OF SEQ ID NOS: 121

<210> SEQ ID NO 1
<211> LENGTH: 504
<212> TYPE: PRT
<213> ORGANISM: Pseudomonas putida NBRC12668

<400> SEQUENCE: 1

Met Ala Ile Ile Arg Pro Thr Leu Glu Gln Leu Gln Ala Leu Ala Ser
1               5                   10                  15

Arg Leu His Met Gln Leu Thr Pro Glu Gln Ala Ser Glu Tyr Leu Ala
            20                  25                  30

Leu Met Gln Ala Ser Leu Asp Ala Tyr Asp Leu Val Asp Glu Leu Pro
        35                  40                  45

Asp Phe Ile Pro Leu Val Arg Tyr Glu Arg Thr Ala Gly Tyr Arg Pro
    50                  55                  60
```

```
Ser Ser Arg Glu Asn Pro Leu Asn Ala Trp Tyr Tyr Arg Thr Glu Val
 65                  70                  75                  80

Met Gly Ala Ser Thr Gly Lys Leu Leu Gly Lys Thr Val Ala Leu Lys
                 85                  90                  95

Asp Asn Ile Ser Leu Ala Gly Val Pro Met Met Asn Gly Ala Ala Pro
            100                 105                 110

Leu Ala Gly Phe Val Pro Ser Phe Asp Ala Thr Val Val Thr Arg Leu
        115                 120                 125

Leu Asp Ala Gly Val Thr Ile Leu Gly Lys Ala Thr Cys Glu His Tyr
    130                 135                 140

Cys Leu Ser Gly Ala Ser His Thr Ser Asp Pro Ala Pro Val His Asn
145                 150                 155                 160

Pro Leu Arg Pro Gly Phe Ser Thr Gly Gly Ser Ser Ser Gly Ser Ala
                165                 170                 175

Ala Leu Val Ala Ala Gly Glu Val Asp Leu Ala Val Gly Gly Asp Gln
            180                 185                 190

Gly Gly Ser Ala Arg Ile Pro Ala Ala Trp Cys Gly Ile Tyr Gly Met
        195                 200                 205

Lys Pro Thr Phe Gly Leu Val Pro Tyr Thr Gly Val Met Ala Ile Glu
    210                 215                 220

Ala Thr Phe Asp His Val Gly Pro Met Thr Ser Asn Val Arg Asp Asn
225                 230                 235                 240

Ala Leu Met Leu Glu Val Met Ala Gly Ala Asp Gly Leu Asp Pro Arg
                245                 250                 255

Gln Gly Val Pro Glu Val Asp Thr Tyr Gly Ser Tyr Leu Glu Arg Gly
            260                 265                 270

Val Arg Gly Leu Arg Ile Gly Ile Leu Gln Gln Gly Phe Gln Leu Ala
        275                 280                 285

Asn Leu Asp Gln Arg Val Gly Asp Lys Val Arg Ser Ala Ile Ala Arg
    290                 295                 300

Phe Glu Ala Leu Gly Ala Val Val Glu Glu Val Ser Val Ala Glu His
305                 310                 315                 320

Thr Leu Ala Gly Ser Leu Trp Ser Pro Ile Gly Cys Glu Gly Leu Thr
                325                 330                 335

Met Gln Met Met His Gly Asn Gly Ala Gly Phe Asn Trp Lys Gly Leu
            340                 345                 350

Tyr Asp Val Ala Leu Leu Asp Lys Gln Ala Gly Trp Arg Thr Gln Ala
        355                 360                 365

Asp Ala Leu Ser Pro Ser Leu Lys Leu Cys Met Leu Val Gly Gln Phe
    370                 375                 380

Gly Leu Glu His Tyr His Gly Arg Tyr Tyr Ala Lys Ala Gln Asn Ile
385                 390                 395                 400

Ala Arg Phe Ala Arg Ala Gly Tyr Asp Lys Ala Leu Glu Arg Tyr Asp
                405                 410                 415

Leu Leu Val Met Pro Thr Val Pro Ile Ile Ala Gln Pro Leu Pro Ala
            420                 425                 430

Pro Gly Cys Ser Ile Thr Glu Ser Val Ser Arg Ala Leu Glu Met Leu
        435                 440                 445

Gly Asn Thr Ala Ala Gln Asp Ile Thr Gly His Pro Ala Met Ser Ile
    450                 455                 460

Pro Cys Gly Leu Val Asp Gly Leu Pro Val Gly Leu Met Leu Val Gly
465                 470                 475                 480

Lys His Tyr Ala Glu Gly Thr Ile Tyr Gln Ala Ala Ala Ala Phe Glu
```

Ala Ala Val Asp Trp Arg Thr Leu
        500

<210> SEQ ID NO 2
<211> LENGTH: 1515
<212> TYPE: DNA
<213> ORGANISM: Pseudomonas putida NBRC12668

<400> SEQUENCE: 2

```
atggccatca tccgcccgac gctcgaacag ttgcaggccc tcgccagccg cctgcacatg      60
cagctgaccc ccgaacaagc cagcgaatac ctggcgctca tgcaggcaag cctcgacgcc     120
tatgacctgg tcgacgaact gccggacttc atccccttgg tgcgctacga gcgcactgcg     180
ggttaccgcc cctccagccg ggagaacccg ttgaacgcct ggtactaccg taccgaggtg     240
atgggcgcca gcaccggcaa actgctcggc aaaacagtcg cactcaagga caacatctcg     300
ctggcgggcg tgccgatgat gaacggtgcc gcgccactgg ccggttttgt accgtcattc     360
gatgccactg tggttacgcg tttgctcgac gccggggtga ccatcctcgg caaggccact     420
tgcgagcact actgcctgtc cggcgccagc cacacctcgg acccggcacc cgtgcacaac     480
ccattgcgcc ctggtttcag caccggcggc tcttcgtcgg gcagcgccgc gctggttgct     540
gcgggcgaag ttgacctggc ggtgggcggc gatcagggcg ttcagcgcg tattcccgca     600
gcgtggtgcg gcatctatgg catgaagccg actttcgggc tggtgccgta ccgggggtg      660
atggcgatcg aggccacctt cgaccatgtc ggcccgatga ccagcaacgt gcgcgacaac     720
gcgctcatgc tcgaagtcat ggccggtgcc gacggccttg acccacgcca gggcgtgccc     780
gaggtcgata cctatggcag ctacctcgag cgcggtgtac gcgggctgcg tatcggcatc     840
ctccagcaag gtttccagct cgctaacctt gatcagcgcg ttggcgacaa ggtgcgcagc     900
gccatcgctc gcttcgaggc gttgggcgca gtggtcgagg aagtatcggt tgccgagcat     960
acgctggccg gctcgctatg gagcccgatc ggctgcgaag gcctgaccat gcagatgatg    1020
cacggcaacg cgcgggcgtt taactggaag ggcctgtatg acgtcgcctt gctcgacaag    1080
caggccggct ggcgaaccca ggccgacgcc ctgtcgccct cgctcaagct gtgcatgctg    1140
gttggccagt ttggcctgga acactaccac ggccgttact acgcaaaggc gcagaacatc    1200
gcccgtttcg cgcgcgccgg ctacgacaag gcgctggagc gctacgacct gctggtaatg    1260
ccaaccgtgc ccatcatcgc ccagccgctg ccggcaccag gttgctcgat caccgagagt    1320
gtctcgcgcg cgctggagat gctcggcaat accgccgcac aagacatcac cggtcacccg    1380
gccatgtcca tcccttgcgg cctggtcgac ggcctgccgg tggggctgat gctggtcggc    1440
aagcactatg ccgaaggcac gatctatcag gccgcggcag cgttcgaggc cgcggtggac    1500
tggcgcacgc tgtga                                                     1515
```

<210> SEQ ID NO 3
<211> LENGTH: 205
<212> TYPE: PRT
<213> ORGANISM: Pseudonocardia thermophila

<400> SEQUENCE: 3

Met Thr Glu Asn Ile Leu Arg Lys Ser Asp Glu Glu Ile Gln Lys Glu
1               5                   10                  15

Ile Thr Ala Arg Val Lys Ala Leu Glu Ser Met Leu Ile Glu Gln Gly
            20                  25                  30

Ile Leu Thr Thr Ser Met Ile Asp Arg Met Ala Glu Ile Tyr Glu Asn

```
                35                  40                  45
Glu Val Gly Pro His Leu Gly Ala Lys Val Val Lys Ala Trp Thr
 50                  55                  60

Asp Pro Glu Phe Lys Lys Arg Leu Leu Ala Asp Gly Thr Glu Ala Cys
 65                  70                  75                  80

Lys Glu Leu Gly Ile Gly Gly Leu Gln Gly Glu Asp Met Met Trp Val
                 85                  90                  95

Glu Asn Thr Asp Glu Val His His Val Val Cys Thr Leu Cys Ser
                100                 105                 110

Cys Tyr Pro Trp Pro Val Leu Gly Leu Pro Pro Asn Trp Phe Lys Glu
                115                 120                 125

Pro Gln Tyr Arg Ser Arg Val Val Arg Glu Pro Arg Gln Leu Leu Lys
    130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
        195                 200                 205

<210> SEQ ID NO 4
<211> LENGTH: 233
<212> TYPE: PRT
<213> ORGANISM: Pseudonocardia thermophila

<400> SEQUENCE: 4

Met Asn Gly Val Tyr Asp Val Gly Gly Thr Asp Gly Leu Gly Pro Ile
 1               5                  10                  15

Asn Arg Pro Ala Asp Glu Pro Val Phe Arg Ala Glu Trp Glu Lys Val
                20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
 50                  55                  60

Glu Ser Pro Tyr Tyr Trp His Trp Ile Arg Thr Tyr Ile His His Gly
 65                  70                  75                  80

Val Arg Thr Gly Lys Ile Asp Leu Glu Glu Leu Glu Arg Arg Thr Gln
                 85                  90                  95

Tyr Tyr Arg Glu Asn Pro Asp Ala Pro Leu Pro Glu His Glu Gln Lys
                100                 105                 110

Pro Glu Leu Ile Glu Phe Val Asn Gln Ala Val Tyr Gly Gly Leu Pro
            115                 120                 125

Ala Ser Arg Glu Val Asp Arg Pro Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
```

```
                 210                 215                 220
Leu Val Asp Thr Lys Ala Ala Ala Ala
225                 230

<210> SEQ ID NO 5
<211> LENGTH: 618
<212> TYPE: DNA
<213> ORGANISM: Pseudonocardia thermophila

<400> SEQUENCE: 5
atgaccgaga acatcctgcg caagtcggac gaggagatcc agaaggagat cacggcgcgg      60
gtcaaggccc tggagtcgat gctcatcgaa cagggcatcc tcaccacgtc gatgatcgac     120
cggatggccg agatctacga gaacgaggtc ggcccgcacc tcggcgcgaa ggtcgtcgtg     180
aaggcctgga ccgacccgga gttcaagaag cgtctgctcg ccgacggcac cgaggcctgc     240
aaggagctcg gcatcggcgg cctgcagggc gaggacatga tgtgggtgga gaacaccgac     300
gaggtccacc acgtcgtcgt gtgcacgctc tgctcctgct accgtggcc ggtgctgggg      360 ctgccgccga actggttcaa ggagccgcag taccgctccc gcgtggtgcg tgagccccgg     420
cagctgctca aggaggagtt cggcttcgag gtcccgccga gcaaggagat caaggtctgg     480
gactccagct ccgagatgcg cttcgtcgtc ctcccgcagc gccccgcggg caccgacggg     540
tggagcgagg aggagctcgc caccctcgtc acccgcgagt cgatgatcgg cgtcgaaccg     600
gcgaaggcgg tcgcgtga                                                   618

<210> SEQ ID NO 6
<211> LENGTH: 702
<212> TYPE: DNA
<213> ORGANISM: Pseudonocardia thermophila

<400> SEQUENCE: 6
atgaacggcg tgtacgacgt cggcggcacc gatgggctgg gcccgatcaa ccggcccgcg      60
gacgaaccgg tcttccgcgc cgagtgggag aaggtcgcgt tcgcgatgtt cccggcgacg     120
ttccgggccg gcttcatggg cctggacgag ttccggttcg gcatcgagca gatgaacccg     180
gccgagtacc tcgagtcgcc gtactactgg cactggatcc gcacctacat ccaccacggc     240
gtccgcaccg gcaagatcga tctcgaggag ctggagcgcc gcacgcagta ctaccgggag     300
aaccccgacg ccccgctgcc cgagcacgag cagaagccgg agttgatcga gttcgtcaac     360
caggccgtct acggcgggct gcccgcaagc cgggaggtcg accgaccgcc caagttcaag     420
gagggcgacg tggtgcggtt ctccaccgcg agcccgaagg ccacgcccg  gcgcgcgcgg     480 tacgtgcgcg gcaagaccgg gacggtggtc aagcaccacg gcgcgtacat ctacccggac     540
accgccggca acggcctggg cgagtgcccc gagcacctct acaccgtccg cttcacggcc     600
caggagctgt gggggccgga agggacccg  aactccagcg tctactacga ctgctgggag     660
ccctacatcg agctcgtcga cacgaaggcg gccgcggcat ga                        702

<210> SEQ ID NO 7
<211> LENGTH: 45
<212> TYPE: DNA
<213> ORGANISM: Artificial Sequence
<220> FEATURE:
<223> OTHER INFORMATION: Oligonucleotide to act as a PCR primer

<400> SEQUENCE: 7
gtgaattcac aaaaaggata aaacaatggc catcatccgc ccgac                      45
```

```
<210> SEQ ID NO 8
<211> LENGTH: 28
<212> TYPE: DNA
<213> ORGANISM: Artificial Sequence
<220> FEATURE:
<223> OTHER INFORMATION: Oligonucleotide to act as a PCR primer

<400> SEQUENCE: 8
tcgaagcttt cacagcgtgc gccagtcc                                          28

<210> SEQ ID NO 9
<211> LENGTH: 48
<212> TYPE: DNA
<213> ORGANISM: Artificial Sequence
<220> FEATURE:
<223> OTHER INFORMATION: Oligonucleotide to act as a PCR primer

<400> SEQUENCE: 9
gtgaattcac aaaaaggata aacaatgtc ccaggaagtc atacgcgg                      48

<210> SEQ ID NO 10
<211> LENGTH: 32
<212> TYPE: DNA
<213> ORGANISM: Artificial Sequence
<220> FEATURE:
<223> OTHER INFORMATION: Oligonucleotide to act as a PCR primer

<400> SEQUENCE: 10
tcgaagcttt catgcggagc tcctctcagc ag                                     32

<210> SEQ ID NO 11
<211> LENGTH: 47
<212> TYPE: DNA
<213> ORGANISM: Artificial Sequence
<220> FEATURE:
<223> OTHER INFORMATION: Oligonucleotide to act as a PCR primer

<400> SEQUENCE: 11
gtgaattcac aaaaaggata aacaatggc cattactcgc cctaccc                      47

<210> SEQ ID NO 12
<211> LENGTH: 31
<212> TYPE: DNA
<213> ORGANISM: Artificial Sequence
<220> FEATURE:
<223> OTHER INFORMATION: Oligonucleotide to act as a PCR primer

<400> SEQUENCE: 12
tcgaagcttt tatcgttctt cggggggggcg g                                     31

<210> SEQ ID NO 13
<211> LENGTH: 50
<212> TYPE: DNA
<213> ORGANISM: Artificial Sequence
<220> FEATURE:
<223> OTHER INFORMATION: Oligonucleotide to act as a PCR primer

<400> SEQUENCE: 13
gtgaattcac aaaaaggata aacaatgat tcacggcgat atttcaagca                   50

<210> SEQ ID NO 14
<211> LENGTH: 34
<212> TYPE: DNA
<213> ORGANISM: Artificial Sequence
<220> FEATURE:
<223> OTHER INFORMATION: Oligonucleotide to act as a PCR primer

<400> SEQUENCE: 14
```

```
tcgaagcttt tacgcgactt cggtgccctg atgg                                34
```

<210> SEQ ID NO 15
<211> LENGTH: 49
<212> TYPE: DNA
<213> ORGANISM: Artificial Sequence
<220> FEATURE:
<223> OTHER INFORMATION: Oligonucleotide to act as a PCR primer

<400> SEQUENCE: 15

```
gtgaattcac aaaaaggata aaacaatgga aacgcgccat ccccctctcc               49
```

<210> SEQ ID NO 16
<211> LENGTH: 32
<212> TYPE: DNA
<213> ORGANISM: Artificial Sequence
<220> FEATURE:
<223> OTHER INFORMATION: Oligonucleotide to act as a PCR primer

<400> SEQUENCE: 16

```
tcgaagcttt taagcgagtg cgaggtcggc cg                                  32
```

<210> SEQ ID NO 17
<211> LENGTH: 45
<212> TYPE: DNA
<213> ORGANISM: Artificial Sequence
<220> FEATURE:
<223> OTHER INFORMATION: Oligonucleotide to act as a PCR primer

<400> SEQUENCE: 17

```
gtgaattcac aaaaaggata aaacaatgac ggcaacttca acccc                    45
```

<210> SEQ ID NO 18
<211> LENGTH: 29
<212> TYPE: DNA
<213> ORGANISM: Artificial Sequence
<220> FEATURE:
<223> OTHER INFORMATION: Oligonucleotide to act as a PCR primer

<400> SEQUENCE: 18

```
tcgaagcttt tagaaaatgg catcagccg                                      29
```

<210> SEQ ID NO 19
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 19

```
gaactgccgg acttcacccc cttggtgcgc tac                                 33
```

<210> SEQ ID NO 20
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 20

```
gtagcgcacc aaggggtga agtccggcag ttc                                  33
```

<210> SEQ ID NO 21
<211> LENGTH: 33
<212> TYPE: DNA
<213> ORGANISM: Artificial Sequence -continued

```
<220> FEATURE:
<223> OTHER INFORMATION: Oligonucleotide to act as a PCR primer

<400> SEQUENCE: 21
tgcgagcact actgcgtgtc cggcgccagc cac                                    33

<210> SEQ ID NO 22
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 22
gtggctggcg ccggacacgc agtagtgctc gca                                    33

<210> SEQ ID NO 23
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 23
tactgcctgt ccggcggcag ccacacctcg gac                                    33

<210> SEQ ID NO 24
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 24
gtccgaggtg tggctgccgc cggacaggca gta                                    33

<210> SEQ ID NO 25
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 25
gccgcgctgg ttgcttcggg cgaagttgac ctg                                    33

<210> SEQ ID NO 26
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 26
caggtcaact tcgcccgaag caaccagcgc ggc                                    33

<210> SEQ ID NO 27
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 27
gcgggcgaag ttgacatcgc ggtgggcggc gat                                    33
```

```
<210> SEQ ID NO 28
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 28
atcgccgccc accgcgatgt caacttcgcc cgc                                    33

<210> SEQ ID NO 29
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 29
gacctggcgg tgggcaccga tcagggcggt tca                                    33

<210> SEQ ID NO 30
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 30
tgaaccgccc tgatcggtgc ccaccgccag gtc                                    33

<210> SEQ ID NO 31
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 31
cagggcgtgc ccgaggccga tacctatggc agc                                    33

<210> SEQ ID NO 32
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 32
gctgccatag gtatcggcct cgggcacgcc ctg                                    33

<210> SEQ ID NO 33
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 33
gggctgcgta tcggcgtcct ccagcaaggt ttc                                    33

<210> SEQ ID NO 34
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 34
```
gaaaccttgc tggaggacgc cgatacgcag ccc                                      33

<210> SEQ ID NO 35
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 35
cttgatcagc gcgttgccga caaggtgcgc agc                                      33

<210> SEQ ID NO 36
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 36
gctgcgcacc ttgtcggcaa cgcgctgatc aag                                      33

<210> SEQ ID NO 37
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 37
gtcgaggaag tatcgattgc cgagcatacg ctg                                      33

<210> SEQ ID NO 38
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 38
cagcgtatgc tcggcaatcg atacttcctc gac                                      33

<210> SEQ ID NO 39
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 39
ggcctgtatg acgtcggctt gctcgacaag cag                                      33

<210> SEQ ID NO 40
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 40
ctgcttgtcg agcaagccga cgtcatacag gcc                                      33

<210> SEQ ID NO 41
<211> LENGTH: 33
<212> TYPE: DNA
<213> ORGANISM: Artificial Sequence

```
<220> FEATURE:
<223> OTHER INFORMATION: Oligonucleotide to act as a PCR primer

<400> SEQUENCE: 41
tcgctcaagc tgtgcctgct ggttggccag ttt                                    33

<210> SEQ ID NO 42
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 42
aaactggcca accagcaggc acagcttgag cga                                    33

<210> SEQ ID NO 43
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 43
atgctggttg gccagtatgg cctggaacac tac                                    33

<210> SEQ ID NO 44
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 44
gtagtgttcc aggccatact ggccaaccag cat                                    33

<210> SEQ ID NO 45
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 45
gcaaaggcgc agaacctcgc ccgtttcgcg cgc                                    33

<210> SEQ ID NO 46
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 46
gcgcgcgaaa cgggcgaggt tctgcgcctt tgc                                    33

<210> SEQ ID NO 47
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 47
atcaccgaga gtgtcgcgcg cgcgctggag atg                                    33
```

```
<210> SEQ ID NO 48
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 48
catctccagc gcgcgcgcga cactctcggt gat                                33

<210> SEQ ID NO 49
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 49
tcgcgcgcgc tggagacgct cggcaatacc gcc                                33

<210> SEQ ID NO 50
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 50
ggcggtattg ccgagcgtct ccagcgcgcg cga                                33

<210> SEQ ID NO 51
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 51
cgcgcgctgg agatgatcgg caataccgcc gca                                33

<210> SEQ ID NO 52
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 52
tgcggcggta ttgccgatca tctccagcgc gcg                                33

<210> SEQ ID NO 53
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 53
atcccttgcg gcctgctcga cggcctgccg gtg                                33

<210> SEQ ID NO 54
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 54
```

```
caccggcagg ccgtcgagca ggccgcaagg gat                                  33

<210> SEQ ID NO 55
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 55
gggctgatgc tggtcgccaa gcactatgcc gaa                                  33

<210> SEQ ID NO 56
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 56
ttcggcatag tgcttggcga ccagcatcag ccc                                  33

<210> SEQ ID NO 57
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 57
gcagcgttcg aggcctcggt ggactggcgc acg                                  33

<210> SEQ ID NO 58
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 58
cgtgcgccag tccaccgagg cctcgaacgc tgc                                  33

<210> SEQ ID NO 59
<211> LENGTH: 33
<212> TYPE: DNA
<213> ORGANISM: Artificial Sequence
<220> FEATURE:
<223> OTHER INFORMATION: Oligonucleotide to act as a PCR primer

<400> SEQUENCE: 59
tacgaattct aaggaggtct cagcatgaac ggc                                  33

<210> SEQ ID NO 60
<211> LENGTH: 21
<212> TYPE: DNA
<213> ORGANISM: Artificial Sequence
<220> FEATURE:
<223> OTHER INFORMATION: Oligonucleotide to act as a PCR primer

<400> SEQUENCE: 60
ctcggtcatg ccgcggccgc c                                               21

<210> SEQ ID NO 61
<211> LENGTH: 24
<212> TYPE: DNA
<213> ORGANISM: Artificial Sequence
```

```
<220> FEATURE:
<223> OTHER INFORMATION: Oligonucleotide to act as a PCR primer

<400> SEQUENCE: 61
atcctcacct cgtcgatgat cgac                                          24

<210> SEQ ID NO 62
<211> LENGTH: 17
<212> TYPE: DNA
<213> ORGANISM: Artificial Sequence
<220> FEATURE:
<223> OTHER INFORMATION: Oligonucleotide to act as a PCR primer

<400> SEQUENCE: 62
caggaaacag ctatgac                                                  17

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide to act as a PCR primer

<400> SEQUENCE: 63
ggccagtgcc tagcttacat                                               20

<210> SEQ ID NO 64
<211> LENGTH: 17
<212> TYPE: DNA
<213> ORGANISM: Artificial Sequence
<220> FEATURE:
<223> OTHER INFORMATION: Oligonucleotide to act as a PCR primer

<400> SEQUENCE: 64
gttttcccag tcacgac                                                  17

<210> SEQ ID NO 65
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 65
gagaaggtcg tgttcgcgat gttc                                          24

<210> SEQ ID NO 66
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 66
ttcccggcga ttttccgggc cggc                                          24

<210> SEQ ID NO 67
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 67
atgaacccgg tcgagtacct cgag                                          24
```

-continued

<210> SEQ ID NO 68
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 68
cagggcgagg agatgatgtg ggtg                                          24

<210> SEQ ID NO 69
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 69
atgaacccgg gcgagtacct cgag                                          24

<210> SEQ ID NO 70
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 70
ttctccacca atagcccgaa gggc                                          24

<210> SEQ ID NO 71
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 71
gaggacatga tgtgggtgga gaac                                          24

<210> SEQ ID NO 72
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 72
ttcccggcgg tgttccgggc cggc                                          24

<210> SEQ ID NO 73
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 73
tactacgaca tgtgggagcc ctac                                          24

<210> SEQ ID NO 74
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 74
cggcgcgcgt gttacgtgcg cggc                                         24

<210> SEQ ID NO 75
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 75
aagaccgggg aggtggtcaa gcac                                         24

<210> SEQ ID NO 76
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 76
tcgatgatct gcgtcgaacc ggcg                                         24

<210> SEQ ID NO 77
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 77
atcctcaccg ggtcgatgat cgac                                         24

<210> SEQ ID NO 78
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 78
gagctcgccg gcctcgtcac ccgc                                         24

<210> SEQ ID NO 79
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 79
cacggcgcgg ccatctaccc ggac                                         24

<210> SEQ ID NO 80
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 80
gtctactacg tctgctggga gccc                                         24

<210> SEQ ID NO 81
<211> LENGTH: 24
<212> TYPE: DNA
<213> ORGANISM: Artificial Sequence

```
<220> FEATURE:
<223> OTHER INFORMATION: Oligonucleotide to act as a PCR primer

<400> SEQUENCE: 81
atgaacggca tgtacgacgt cggc                                              24

<210> SEQ ID NO 82
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 82
tacgacgtcg ccggcaccga tggg                                              24

<210> SEQ ID NO 83
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 83
gagaaggtca tgttcgcgat gttc                                              24

<210> SEQ ID NO 84
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 84
cacggcgcga ccatctaccc ggac                                              24

<210> SEQ ID NO 85
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 85
tacatccaca acggcgtccg cacc                                              24

<210> SEQ ID NO 86
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 86
cgccgcacgc gttactaccg ggag                                              24

<210> SEQ ID NO 87
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 87
atgaacccgt gggagtacct cgag                                              24
```

```
<210> SEQ ID NO 88
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 88
gtctactacc actgctggga gccc                                           24

<210> SEQ ID NO 89
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 89
gccccgctga tggagcacga gcag                                           24

<210> SEQ ID NO 90
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 90
atcgagctca tcgacacgaa ggcg                                           24

<210> SEQ ID NO 91
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 91
atgaacccgt cggagtacct cgag                                           24

<210> SEQ ID NO 92
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 92
cggcgcgcga tgtacgtgcg cggc                                           24

<210> SEQ ID NO 93
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 93
cacgagcagg tgccggagtt gatc                                           24

<210> SEQ ID NO 94
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 94
```
gtctactaca tgtgctggga gccc                                          24

<210> SEQ ID NO 95
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 95
gacgaggagc tccagaagga gatc                                          24

<210> SEQ ID NO 96
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 96
atcctcaccg cgtcgatgat cgac                                          24

<210> SEQ ID NO 97
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 97
atctacgagc aagaggtcgg cccg                                          24

<210> SEQ ID NO 98
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 98
ctggagtcga tcctcatcga acag                                          24

<210> SEQ ID NO 99
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 99
cacggcgcga tgatctaccc ggac                                          24

<210> SEQ ID NO 100
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 100
gtctactacg gctgctggga gccc                                          24

<210> SEQ ID NO 101
<211> LENGTH: 24
<212> TYPE: DNA
<213> ORGANISM: Artificial Sequence

```
<220> FEATURE:
<223> OTHER INFORMATION: Oligonucleotide to act as a PCR primer

<400> SEQUENCE: 101
atgaacccgc tggagtacct cgag                                              24

<210> SEQ ID NO 102
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 102
cacgagcaga ttccggagtt gatc                                              24

<210> SEQ ID NO 103
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 103
atgaacccga cggagtacct cgag                                              24

<210> SEQ ID NO 104
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 104
tactacgact cctgggagcc ctac                                              24

<210> SEQ ID NO 105
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 105
gacgtggtgg ggttctccac cgcg                                              24

<210> SEQ ID NO 106
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 106
gtctactaca gctgctggga gccc                                              24

<210> SEQ ID NO 107
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 107
ttcccggcgc tgttccgggc cggc                                              24
```

```
<210> SEQ ID NO 108
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 108
gtctactacc tctgctggga gccc                                           24

<210> SEQ ID NO 109
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 109
cccgagcaca accagaagcc ggag                                           24

<210> SEQ ID NO 110
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 110
acgaaggcgg tcgcggcatg accg                                           24

<210> SEQ ID NO 111
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 111 ctgtggggc tggaagggga cccg                                            24

<210> SEQ ID NO 112
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 112
gacacgaagg aggccgcggc atga                                           24

<210> SEQ ID NO 113
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 113
ttctccacct cgagcccgaa gggc                                           24

<210> SEQ ID NO 114
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 114
```
gtctactact gttgctggga gccc                                        24

<210> SEQ ID NO 115
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 115
acggtggtcg cgcaccacgg cgcg                                        24

<210> SEQ ID NO 116
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 116
gtctactaca cctgctggga gccc                                        24

<210> SEQ ID NO 117
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 117
atctacgagg aagaggtcgg cccg                                        24

<210> SEQ ID NO 118
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 118
atcctcacct ggtcgatgat cgac                                        24

<210> SEQ ID NO 119
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 119
cacggcgcgt gcatctaccc ggac                                        24

<210> SEQ ID NO 120
<211> LENGTH: 24
<212> TYPE: DNA
<213> ORGANISM: Artificial Sequence
<220> FEATURE:
<223> OTHER INFORMATION: Oligonucleotide to act as a PCR primer

<400> SEQUENCE: 120
gccccgctga tggatcacga gcag                                        24

<210> SEQ ID NO 121
<211> LENGTH: 24
<212> TYPE: DNA
<213> ORGANISM: Artificial Sequence

```
<220> FEATURE:
<223> OTHER INFORMATION: Oligonucleotide to act as a PCR primer

<400> SEQUENCE: 121
gacacgaagg aggcgcggca tgac                                          24
```

METHOD FOR PRODUCING 3-MERCAPTOPROPIONIC ACID OR SALT THEREOF

The present application is the National Stage of International Application No. PCT/JP2010/003097, filed Apr. 30, 2010, and claims foreign priority to Japanese Application No. 2009-111257, filed Apr. 30, 2009, the entire contents of each of which are incorporated by reference herein.

TECHNICAL FIELD

The present invention relates to a method for producing a 3-mercaptopropionic acid or a salt thereof.

BACKGROUND ART

The 3-mercaptopropionic acid is a useful compound as a raw material of an organic synthetic product including an agricultural chemical and a medicine, a stabilizer of polyvinyl chloride, a crosslinking agent of an epoxy resin or an acrylic acid ester polymer, or a raw material of a plastic lens monomer.

A method for producing a 3-mercaptopropionic acid by hydrolysis of 3-mercaptopropionitrile is known, and a method of chemical hydrolysis of 3-mercaptopropionitrile has been carried out with the addition of an acid or a base (for example, Patent Documents 1 and 2). In addition, Patent Documents 6 and 7 disclose a method for chemically synthesizing a 3-mercaptopropionic acid from acrylonitrile.

Also, a method of hydrolysis of a nitrile compound or an amide compound under mild conditions using a microorganism has been reported in many cases (for example, Non-Patent Documents 1 to 3, and Patent Documents 3 and 4). Patent Document 5 discloses a method of hydrolysis of 3-mercaptopropionitrile using a microorganism.

RELATED DOCUMENTS

Patent Documents

Patent Document 1: Japanese Laid-open Patent Publication No. Hei 4 (1992)-305563
Patent Document 2: Japanese Laid-open Patent Publication No. 2001-187778
Patent Document 3: Japanese Laid-open Patent Publication No. 2008-022706
Patent Document 4: Japanese Laid-open Patent Publication No. 2005-176639
Patent Document 5: Japanese Laid-open Patent Publication No. Show a 58 (1983)-201992
Patent Document 6: Chinese Patent Publication No. CN1793117A
Patent Document 7: Chinese Patent Publication No. CN101125827A

Non-Patent Documents

Non-Patent Document 1: Journal of Applied Microbiology, 95, 1161-1174 (2003)
Non-Patent Document 2: Journal of Applied Microbiology, 91, 381-393 (2001)
Non-Patent Document 3: Archives of Microbiology (1984) 138, 315-320

DISCLOSURE OF THE INVENTION

In a chemical method, a high reaction yield is achieved by optimizing hydrolysis conditions, while a by-product such as a thiodipropionic acid or the like is produced. Such a compound requires a process of separating the by-product through distillation or the like. Accordingly, the chemical method is not necessarily considered excellent industrially.

An enzymatic reaction is carried out under mild conditions, so that it is an industrially excellent method. However, an enzymatic method for producing a 3-mercaptopropionic acid has not been specifically revealed. In Patent Document 5, the purity of the 3-mercaptopropionic acid to be obtained has not been revealed, and it is not known whether the method is industrially useful or not. In addition, since Patent Document 5 fails to specifically describe an enzyme involved in the reaction, it has been difficult to improve a process of producing a 3-mercaptopropionic acid.

The present invention has been accomplished in view of the above circumstances. An object of the present invention is to provide a method for producing a 3-mercaptopropionic acid industrially by an enzymatic reaction.

That is, the present invention is specified by matters described in below.

[1] A method for producing a carboxylic acid represented by the general formula (2) or a salt thereof from amide represented by the general formula (1) or a salt thereof with the use of amidase,

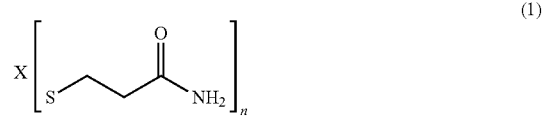

wherein, in the general formula (1), X represents any of H, S—$C_2H_4$—$CONH_2$, S—$C_2H_4$—COOH and a cation; and n represents 1 when X is H, S—$C_2H_4$—$CONH_2$, or S—$C_2H_4$—COOH, and n represents the same integer as the valence of X when X is a cation,

wherein, in the general formula (2), Y represents any of H and S—$C_2H_4$—COOH.

[2] The method according to [1], in which the amide represented by the general formula (1) or the salt thereof is produced from nitrile represented by the general formula (3) or a salt thereof with the use of nitrile hydratase, and the carboxylic acid represented by the general formula (2) or the salt thereof is produced from the amide or the salt thereof,

wherein, in the general formula (3), Z represents any of H, S—$C_2H_4$—CN, S—$C_2H_4$—$CONH_2$ and a cation; and n represents 1 when Z is H or S—$C_2H_4$—$CONH_2$, and n represents the same integer as the valence of Z when Z is a cation.

[3] The method according to [2], in which the carboxylic acid represented by the general formula (2) or the salt thereof is produced from the nitrile represented by the general formula (3) or the salt thereof in the presence of nitrile hydratase and amidase.

[4] The method according to [2] or [3], in which the nitrile hydratase is derived from a bacterium belonging to the genus *Pseudonocardia*.

[5] The method according to [4], in which the concentration of at least one of the amide represented by the general formula (1) or the salt thereof and the nitrile represented by the general formula (3) or the salt thereof in a reaction solution is equal to or more than 11 weight %.

[6] The method according to any one of [2] to [5], in which the nitrile represented by the general formula (3) or the salt thereof is obtained by reacting acrylonitrile with a compound containing a sulfur atom.

[7] The method according to [6], in which the compound containing a sulfur atom is sodium hydrogen sulfide.

[8] The method according to any one of [1] to [7], in which said amidase belongs to the amidase signature family.

[9] A method for producing pentaerythritol tetrakis(3-mercaptopropionate) including:
producing a carboxylic acid represented by the general formula (2) using the method according to any one of [1] to [8]; and
carrying out an esterification reaction of the obtained carboxylic acid and pentaerythritol.

[10] A method for producing an optical material including:
producing pentaerythritol tetrakis(3-mercaptopropionate) using the method according to [9]; and
monopolymerizing or copolymerizing the obtained pentaerythritol tetrakis(3-mercaptopropionate), and then curing it.

[11] A method for producing a 3-mercaptopropionic acid from 3-mercaptopropionitrile or a salt thereof with the use of nitrilase.

According to the present invention, the 3-mercaptopropionic acid or the salt thereof is produced from amide represented by the general formula (1) or a salt thereof with the use of amidase. Accordingly, since the by-product is also reduced by the chemical synthetic method, a purification procedure may be simplified. Accordingly, the 3-mercaptopropionic acid or the salt thereof can be efficiently produced.

According to the present invention, the 3-mercaptopropionic acid or the salt thereof can be efficiently produced on an industrially.

BRIEF DESCRIPTION OF THE DRAWINGS

The above and other objects, advantages and features of the present invention will be more apparent from the following description of certain preferred embodiments taken in conjunction with the accompanying drawings, in which:

FIG. 1 is an electropherogram of the fungal suspension of Example 7. The density of the bands represented by arrows in FIG. 1 represents the expression level of the enzyme used for the reaction. A is Psp-amidase. B is Acr-amidase, C is Ppu-amidase, and D is Pch-amidase.

DESCRIPTION OF EMBODIMENTS

A 3-mercaptopropionitrile derivative in the present invention is represented by the above general formula (3), and is a compound in which Z in the general formula (3) represents any of H, S—$C_2H_4$—CN, S—$C_2H_4$—$CONH_2$ and a cation.

A 3-mercaptopropionamide derivative in the present invention is represented by the above general formula (1), and is a compound in which X in the general formula (1) represents any of H, S—$C_2H_4$—$CONH_2$, S—$C_2H_4$—COOH and a cation.

A 3-mercaptopropionic acid derivative in the present invention is represented by the general formula (2), and is a compound in which Y in the general formula (2) represents any of H and S—$C_2H_4$—COOH.

First Embodiment

This embodiment relates to a method for producing a carboxylic acid represented by the general formula (2) or a salt thereof from the 3-mercaptopropionamide derivative represented by the general formula (1) (however, in the general formula (1), X is H, a monovalent cation, a divalent cation or a trivalent cation) with the use of amidase. In this embodiment, when n is 1 to 3, and n is 1, in the general formula (1), X is H or a monovalent cation. When, in the general formula (1), n is 2, X is a divalent cation. When n is 3, X is a trivalent cation. Specifically, as the monovalent cation, for example, alkali metal ion or ammonium ion may be used. Examples of the alkali metal ion include $Li^+$, $Na^+$, $K^+$, $Rb^+$ and $Cs^+$. Examples of the divalent cation include $Be^{2+}$, $Mg^{2+}$, or alkali earth metal ion such as $Ca^{2+}$, $Sr^{2+}$, $Ba^{2+}$ and $Ra^{2+}$. As the trivalent cation, $Al^{3+}$ is cited. In the general formula (2), Y is H, but it may form carboxylate or thiolate having a counter ion corresponding to X in the general formula (1).

One example of the reaction formula of this embodiment is represented by the following reaction formula (4). The reaction formula (4) represents an example of a method for producing a 3-mercaptopropionic acid with the use of 3-mercaptopropionamide or a salt thereof. In the reaction formula (4), as X and Y, preferably used is a monovalent cation.

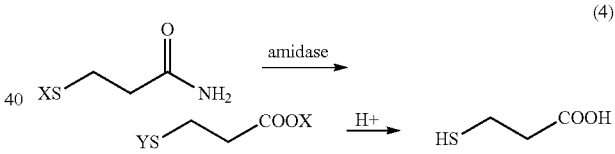

(4)

Amidase refers to an enzyme acting on an amide group in an amide compound and hydrolyzing the amide group to give a carboxyl group. As amidase, there has been known a group (for example, amidase of fatty acid amide, THE JOURNAL OF BIOLOGICAL CHEMISTRY, Vol. 275, No. 25, Issue of June 23, pp. 19177-19184, 2000, hereinafter referred to as Reference Document 1) of cysteines (for example, amidase of *Pseudomonas aeruginosa*, FEBS Lett., 1995, pp 275) called the amidase signature (AS) family having the amidase active center of lysine, serine and serine. The group called the AS family having the active center of lysine, serine and serine refers to a group of amidases in which lysine, serine and serine in the amino acid sequence with high conservation as the amino acid sequence of various amidases, as indicated in FIG. 1 of the above Reference Document 1, are essential for the activity, and the activity is completely disappeared by converting the above amino acid to other amino acids.

In this embodiment, amidase may be amidase originated from microorganisms (bacteria, yeast or the like), plants, molds, animals, insects or the like. Examples of the microorganism known to produce amidase include microorganisms belonging to *Corynebacterium* genus, *Nocardia* genus, *Pseudomonas* genus, *Bacillus* genus, *Bacteridium* genus, *Brevibacterium* genus, *Micrococcus* genus, *Rhodococcus* genus, *Aeromonas* genus, *Citrobacter* genus, *Agrobacterium* genus, *Erwinia* genus, *Enterobacter* genus, *Streptomyces* genus, *Rhizobium* genus, *Pseudonocardia* genus, *Acidphilium* genus, *Polaromonas* genus, *Sulfolobus* genus and the like.

Examples of the amidase carrying out hydrolysis more efficiently include a group of amidases called the AS family having the amidase active center of lysine, serine and serine. Examples of the bacteria producing a group of amidases called the AS family having the amidase active center of lysine, serine and serine include *Pseudomonas putida* NBRC12668, *Pseudonocardia thermophila* JCM3095, *Pseudomonas chlororaphis* B23 and *Acidiphilium crytum* JF-5. According to knowledge of the present inventors, 3-mercaptopropionamide inhibits the enzyme activity, whereas amidase belonging to the AS family may be suitably used because it is hardly affected by inhibition of the enzyme activity by 3-mercaptopropionamide. Among these, amidase belonging to the AS family of biological origin which does not belong to an extremely thermophilic bacterium and a super thermophilic bacterium is more preferably used when it is used in a host growing at normal temperature such as *Escherichia coli* or the like, because amidase is easily expressed. Particularly preferably used is amidase derived from *Pseudomonas putida* NBRC12668 or *Pseudonocardia thermophila* JCM3095. The amino acid sequence and the DNA sequence of amidase derived from *Pseudomonas putida* NBRC12668 are set forth in SEQ ID Nos: 1 and 2 in the Sequence Listing.

In this embodiment, in a group of amidases called the AS family having the amidase active center of lysine, serine and serine, amidase may be used so long as the enzyme activity is kept even though a part of the amino acid sequence is substituted, inserted or deleted. Specifically, there may also be used amidase in which a part of the amino acid sequence of amidase derived from *Pseudomonas putida* NBRC12668 is substituted.

For example, there may be used an amidase variant including substitution of at least one amino acid selected from amino acid substitution as follows and having the amidase activity; in the amino acid sequence as set forth in SEQ ID No: 1 in the Sequence Listing, 51st Ile is substituted by Thr, 146th Leu is substituted by Val, 149th Ala is substituted by Gly, 181st Ala is substituted by Ser, 186th Leu is substituted by Ile, 190th Gly is substituted by Thr, 262nd Val is substituted by Ala, 280th Ile is substituted by Val, 295th Gly is substituted by Ala, 317th Val is substituted by Ile, 356th Ala is substituted by Gly, 379th Met is substituted by Leu, 384th Phe is substituted by Tyr, 400th Ile is substituted by Leu, 442nd Ser is substituted by Ala, 447th Met is substituted by Thr, 448th Leu is substituted by Ile, 469th Val is substituted by Leu, 480th Gly is substituted by Ala, and 498th Ala is substituted by Ser.

In this specification, amino acids, peptides and proteins are indicated by abbreviations adopted by the IUPAC-IUB Commission on Biochemical Nomenclature (CBN) below. Unless otherwise particularly specified, the amino acid residue sequence of peptides and proteins is set forth left to right to be from the N-terminus to the C-terminus, or such that the N-terminus becomes the number 1.

A=Ala=alanine, C=Cys=cysteine,
D=Asp=aspartic acid, E=Glu=glutamic acid,
F=Phe=phenylalanine, G=Gly=glycine,
H=His=histidine, I=Ile=isoleucine,
K=Lys=lysine, L=Leu=leucine,
M=Met=methionine, N=Asn=asparagine,
P=Pro=proline, Q=Gln=glutamine,
R=Arg=arginine, S=Ser=serine,
T=Thr=threonine, V=Val=valine,
W=Trp=tryptophan, Y=Tyr=tyrosine.

As amidase of this embodiment, a transformant transformed so as to produce amidase may also be used. DNA encoding amidase and DNA hybridizing to this DNA can be obtained from the transformant by cloning a gene encoding amidase registered on a gene database GenBank or the like into the expression vector. As the vector used for cloning, suitably used are any vectors constructed for gene recombination from phages or plasmids capable of autonomously replicating in the host bacteria. Examples of the phage include, when *Escherichia coli* is used as the host bacteria, Lambda gt10, Lambda gt11 and the like. Examples of the plasmid include, when *Escherichia coli* is used as the host bacteria, pBTrp2, pBTac1, pBTac2 (all manufactured by Boehringer Mannheim Co.), pKK233-2 (manufactured by Pharmacia Co.), pSE280 (manufactured by Invitrogen Corporation), pGEMEX-1 (manufactured by Promega Corporation), pQE-8 (manufactured by Qiagen Corporation), pQE-30 (manufactured by Qiagen Corporation), pBluescriptII SK$^+$, pBluescriptII SK(−) (manufactured by Stratagene Co.), pET-3 (manufactured by Novagen Inc.), pUC18 (manufactured by Takara Shuzo Co., Ltd.), pSTV28 (manufactured by Takara Shuzo Co., Ltd.), pSTV29 (manufactured by Takara Shuzo Co., Ltd.), pUC118 (manufactured by Takara Shuzo Co., Ltd.) and the like. When an enzyme derived from a bacterium different from the host is introduced and expressed by gene recombination or the like, it is more preferable to use codon usage by modifying so as to match the host.

As the promoter, any promoter may be used so long as amidase is expressed in the host cell. Examples include promoters derived from *Eschenchia coli*, phages and the like, such as a trp promoter ($P_{trp}$), a lac promoter ($P_{lac}$) a $P_L$ promoter, a $P_H$ promoter, a $P_{SE}$ promoter and the like. Additionally, promoters artificially designed and modified may be used, such as a tac promoter and a lacT7 promoter. Np promoters (Japanese Patent Publication No. Hei 8 (1996)-24586) for expressing in a bacterium belonging to the genus *Bacillus* may also be used.

With regard to the ribosome binding sequence, any sequence may be used so long as amidase is expressed in the host cell. However, it is preferable to use a plasmid in which the space between the Shine-Dalgarno sequence and the initiation codon is adjusted to an appropriate distance (for example, 6 to 18 bases).

In order to carry out transcription and translation efficiently, the protein may be expressed, in which the N-terminus of the protein encoding the expression vector is fused with the protein in which the N-terminus of the protein having the protein activity or a part thereof is deleted.

The medium for culturing a transformant is not particularly limited, so long as a medium is capable of growing a transformant. As the medium, there is usually used a liquid medium containing a carbon source, a nitrogen source or other nutrients.

Examples of the carbon source of the medium include saccharides such as glucose, sucrose, starch and the like; alcohols such as sorbitol, methanol, ethanol, glycerol and the like; organic acids such as fumaric acid, citric acid, acetic acid and the like, and a salt thereof; hydrocarbons such as paraffin and the like, and a mixture thereof.

Examples of the nitrogen source of the medium include ammonium salts of inorganic acids such as ammonium sulfate, ammonium nitrate and the like; ammonium salts of organic acids such as ammonium fumarate and the like; other organic or inorganic nitrogen-containing compounds such as meat extract, yeast extract, urea, amino acid and the like, and a mixture thereof.

A nutrient source used for usual culturing, such as inorganic salts including magnesium chloride, ferric chloride and the like; a very small amount of metal salts, vitamins and the like, may be suitably added to the medium. As necessary, factors accelerating the growth of the transformant, buffer substances effective for keeping the medium pH or the like may be added.

The transformant may be cultured under the conditions suitable for growing, for example, a medium pH of 2 to 12 and preferably pH of 4 to 10, and a temperature of 5 to 50 degrees centigrade and preferably from 20 to 50 degrees centigrade. The transformant is cultured depending on the kind of the transformant and may be carried out under any of anaerobic and aerobic condition, but may be more preferably carried out under the aerobic condition. The culture time is, for example, from about 1 to 240 hours, preferably from about 5 to 120 hours, and further preferably from about 12 to 72 hours.

The cultured transformant may be used for the reaction as it is, or may be used for the reaction after various treatments. Examples of such treatments of the transformant include a disruption treatment, a freeze-drying treatment, an extraction treatment and the like. As the extraction treatment, there may be used a conventional method such as an ultrasonic method, a freezing-thawing method, a lysozyme method and the like. Amidase may be taken out from the transformant by carrying out such treatments. The obtained amidase may be used without purification or may be used after purification.

For example, the transformant separated from the culture liquid by centrifugal separation or the like is washed with water or the like, and then suspended in a buffer solution with the pH value in a stable region of the enzyme, and the transformant is disrupted by French press or ultrasonic treatment at a low temperature (3 to 18 degrees centigrade, preferably 3 to 10 degrees centigrade). The transformant fragment is separated and removed by centrifugal separation or the like, and the obtained transformant extract is fractionated with ammonium sulfate and dialyzed according to a conventional method, thus to obtain a crude extract of amidase. Amidase of high purity can be obtained, for example, by a method of subjecting the crude extract of amidase to column chromatography using Sephadex G-200 or the like.

A transformant with changing permeability of the cell membrane by a surfactant, or an organic solvent such as toluene or the like may also be used.

The transformant or amidase may be immobilized by a conventional method such as a polyacrylamide gel method or the like.

As the reaction condition for producing a 3-mercaptopropionic acid from 3-mercaptopropionamide or a salt thereof, the temperature is preferably from 0 to 50 degrees centigrade, more preferably from 0 to 40 degrees centigrade, and further preferably from 5 to 35 degrees centigrade. The reaction pH is from 3.0 to 10.0, and preferably from 6.0 to 8.0. As the acid used for adjusting the pH, there may be used mineral acids such as hydrochloric acid, sulfuric acid, phosphoric acid and the like; and organic acids such as acetic acid and the like. As the reaction solvent, there may be used water; alcohols such as methanol, ethanol and the like; fatty acid esters such as ethyl acetate, butyl acetate and the like; and aromatic compounds such as toluene, xylene and the like, but particularly preferably used is water. The concentration of 3-mercaptopropionamide in the reaction solution is preferably equal to or more than 1 weight %, industrially favorably equal to or more than 11 weight %, and further preferably equal to or more than 13 weight %. The concentration of 3-mercaptopropionamide in the reaction solution is equal to or less than 50 weight %, and more preferably equal to or less than 17 weight %. The reaction solution mentioned in this paragraph contains any of 3-mercaptopropionamide as a reaction substrate dissolved in a reaction solvent, 3-mercaptopropionamide dispersed in a reaction solvent, and 3-mercaptopropionamide phase-separated from a reaction solvent. The concentration mentioned herein refers to a concentration when 3-mercaptopropionamide is all dissolved in a reaction solvent, and 3-mercaptopropionamide may be actually fully dissolved in a reaction solvent, or may not be dissolved. The reaction time is usually from about 10 to 80 hours. It is desirable that the reaction solution in the reaction is replaced with inert gas such as nitrogen or the like, and the gas phase is replaced with inert gas as well.

The 3-mercaptopropionic acid to be obtained may be separated by solvent extraction. A preferable solvent is a suitable polar organic solvent which dissolves a carboxyl group of a product and is not mixed with water. Examples of such a solvent include butyl acetate, ethyl acetate, methyl isobutyl ketone, methylene chloride, methyl ethyl ketone, methyl isobutyl ketone and the like. Furthermore, the 3-mercaptopropionic acid may be isolated using a general method by distillation or the like. In this embodiment, since the purity of the 3-mercaptopropionic acid to be obtained is high, the 3-mercaptopropionic acid may be isolated without through a complicated purification procedure. For example, since the 3-mercaptopropionic acid and water are separated by the addition of the acid to the reaction solution, the 3-mercaptopropionic acid can also be obtained only by recovering the 3-mercaptopropionic acid phase. When the fluid volume of the 3-mercaptopropionic acid phase is small, the 3-mercaptopropionic acid phase may be separated by solvent extraction using the aforementioned polar organic solvent. In this case, as the acid, there may be suitably used mineral acids such as hydrochloric acid, sulfuric acid, phosphoric acid and the like. The 3-mercaptopropionic acid may also be purified by carrying out distillation at atmospheric pressure or under reduced pressure.

Subsequently, the operational effects of this embodiment will be described. According to the invention, the 3-mercaptopropionic acid is produced from the 3-mercaptopropionamide or the salt thereof with the use of amidase. Accordingly, the by-product may be reduced, and the purification procedure may be simplified. Accordingly, the 3-mercaptopropionic acid can be efficiently produced industrially.

As the by-product, there has been known a compound of the chemical formula (5). The chemical formula (5) is a thiodipropionic acid. According to the chemical method, the by-product may not be reduced. Thus, the purification procedure of the 3-mercaptopropionic acid became complicated. On the other hand, as shown in this embodiment, the yield of such a by-product may be equal to or less than 10 mole % by producing the 3-mercaptopropionic acid with the use of amidase. The yield may be equal to or less than 5 mole % and more preferably equal to or less than 1 mole % by suitably selecting the kind of amidase. Accordingly, the 3-mercaptopropionic acid can be obtained with high purity without through the complicated purification procedure such as distillation or the like. The yield of the aforementioned by-product is determined from the following numerical equation (7).

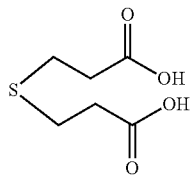

(5)

Yield of by-product(%)=[(substance amount (mole) of thiodipropionic acid/substance amount (mole) of 3-mercaptopropionamide introduced]×100     (7)

Second Embodiment

This embodiment relates to a method for producing a 3-mercaptopropionic acid from a 3-mercaptopropionamide derivative represented by the general formula (1), which is produced from the 3-mercaptopropionitrile derivative represented by the general formula (3) (however, in the general formula (3), Z is H, a monovalent cation, a divalent cation or a trivalent cation) with the use of nitrile hydratase. In this embodiment, when n is 1 to 3, and n is 1, in the general formula (3), Z is hydrogen or a monovalent cation. When, in the general formula (3), n is 2, Z is a divalent cation. When n is 3, Z is a trivalent cation. Specifically, as the monovalent cation, for example, alkali metal ion or ammonium ion may be used. Examples of the alkali metal ion include $Li^+$, $Na^+$, $K^+$, $Rb^+$ and $Cs^+$. Examples of the divalent cation include $Be^{2+}$, $Mg^{2+}$, or alkali earth metal ion such as $Ca^{2+}$, $Sr^{2+}$, $Ba^{2+}$ and $Ra^{2+}$. As the trivalent cation, $Al^{3+}$ is cited. In the general formula (1), X is hydrogen or a cation corresponding to Z in the general formula (3). In the general formula (2), Y is hydrogen, but it may form carboxylate or thiolate having a counter ion corresponding to Z in the general formula (3).

One example of the reaction formula of this embodiment is represented by the following reaction formula (8). The reaction formula (8) represents an example of a method for producing a 3-mercaptopropionic acid with the use of 3-mercaptopropionic acid nitrile or a salt thereof. In the reaction formula (8), as X, more preferably used is a monovalent cation.

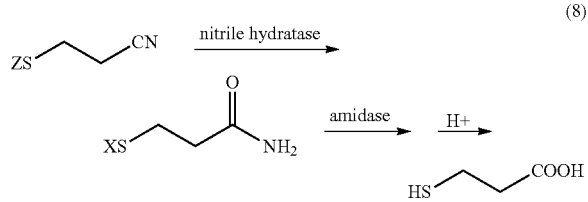

(8)

The nitrile hydratase refers to an enzyme acting on a nitrile group in a nitrile compound, and hydrolyzing the nitrile group to give an amide group. The nitrile hydratase used in this embodiment may be any of nitrile hydratases originated from microorganisms, plants, molds, animals, insects and the like so long as 3-mercaptopropionitrile is efficiently hydrolyzed.

Examples of the microorganism known to produce nitrile hydratase include microorganisms belonging to *Corynebacterium* genus, *Nocardia* genus, *Pseudomonas* genus, *Bacillus* genus, *Bacteridium* genus, *Brevibacterium* genus, *Micrococcus* genus, *Rhodococcus* genus, *Aeromonas* genus, *Citrobacter* genus, *Agrobacterium* genus, *Erwinia* genus, *Enterobacter* genus, *Streptomyces* genus, *Rhizobium* genus, *Pseudonocardia* genus and the like.

As nitrile hydratase carrying out hydrolysis more efficiently, preferably used is nitrile hydratase derived from *Pseudonocardia thermophila* JCM3095. The amino acid sequence and the DNA sequence of the α-subunit of the nitrile hydratase derived from *Pseudonocardia thermophila* JCM3095 are set forth in SEQ ID Nos: 3 and 5 in the Sequence Listing, while the amino acid sequence and the DNA sequence of the β-subunit are set forth in SEQ ID Nos: 4 and 6 in the Sequence Listing.

Nitrile hydratases in which a part of the amino acid sequence of the aforementioned nitrile hydratase is substituted, inserted or deleted may be used so long as the enzyme activity as nitrile hydratase is preserved. For example, as the nitrile hydratase composed of the α-subunit as set forth in SEQ ID No: 3 in the Sequence Listing and the β-subunit as set forth in SEQ ID No: 4 in the Sequence Listing, a nitrile hydratase variant having the nitrile hydratase activity may be used.

Specifically, (aa) 36th Thr in the α-subunit is substituted by Met, and 126th Phe in the α-subunit is substituted by Tyr;

(ab) 148th Gly in the α-subunit is substituted by Asp, and 204th Val in the α-subunit is substituted by Arg;

(ac) 51st Phe in the β-subunit is substituted by Val, and 108th Glu in the β-subunit is substituted by Asp;

(ad) 118th Phe in the β-subunit is substituted by Val, and 200th Ala in the β-subunit is substituted by Glu;

(ae) 160th Arg in the β-subunit is substituted by Trp, and 186th Leu in the β-subunit is substituted by Arg;

(af) 6th Leu in the α-subunit is substituted by Thr, 36th Thr in the α-subunit is substituted by Met, and 126th Phe in the α-subunit is substituted by Tyr;

(ag) 19th Ala in the α-subunit is substituted by Val, 71st Arg in the α-subunit is substituted by His, and 126th Phe in the α-subunit is substituted by Tyr;

(ah) 36th Thr in the α-subunit is substituted by Met, 148th Gly in the α-subunit is substituted by Asp, and 204th Val in the α-subunit is substituted by Arg;

(ai) 10th Thr in the β-subunit is substituted by Asp, 118th Phe in the β-subunit is substituted by Val, and 200th Ala in the β-subunit is substituted by Glu;

(aj) 37th Phe in the β-subunit is substituted by Leu, 108th Glu in the β-subunit is substituted by Asp, and 200th Ala in the β-subunit is substituted by Glu;

(ak) 37th Phe in the β-subunit is substituted by Val, 108th Glu in the β-subunit is substituted by Asp, and 200th Ala in the β-subunit is substituted by Glu;

(al) 41st Phe in the β-subunit is substituted by Ile, 51st Phe in the β-subunit is substituted by Val, and 108th Glu in the β-subunit is substituted by Asp;

(am) 46th Met in the β-subunit is substituted by Lys, 108th Glu in the β-subunit is substituted by Arg, and 212th Ser in the β-subunit is substituted by Tyr;

(an) 48th Leu in the β-subunit is substituted by Val, 108th Glu in the β-subunit is substituted by Arg, and 212th Ser in the β-subunit is substituted by Tyr;

(ao) 127th Leu in the β-subunit is substituted by Ser, 160th Arg in the β-subunit is substituted by Trp, and 186th Leu in the β-subunit is substituted by Arg;

(ap) 6th Leu in the α-subunit is substituted by Thr, 19th Ala in the α-subunit is substituted by Val, 126th Phe in the α-subunit is substituted by Tyr, 46th Met in the β-subunit is substituted by Lys, 108th Glu in the β-subunit is substituted by Arg, and 212th Ser in the β-subunit is substituted by Tyr;

(aq) 6th Leu in the α-subunit is substituted by Thr, 19th Ala in the α-subunit is substituted by Val, 126th Phe in the α-subunit is substituted by Tyr, 48th Leu in the β-subunit is substituted by Val, 108th Glu in the β-subunit is substituted by Arg, and 212th Ser in the β-subunit is substituted by Tyr;

(ar) 6th Leu in the α-subunit is substituted by Ala, 19th Ala in the α-subunit is substituted by Val, 126th Phe in the α-subunit is substituted by Tyr, 127th Leu in the (1-subunit is substituted by Ser, 160th Arg in the β-subunit is substituted by Trp, and 186th Leu in the β-subunit is substituted by Arg;

(as) 6th Leu in the α-subunit is substituted by Thr, 36th Thr in the α-subunit is substituted by Met, 126th Phe in the α-subunit is substituted by Tyr, 10th Thr in the β-subunit is substituted by Asp, 118th Phe in the β-subunit is substituted by Val, and 200th Ala in the β-subunit is substituted by Glu;

(at) 19th Ala in the α-subunit is substituted by Val, 71st Arg in the α-subunit is substituted by His, 126th Phe in the α-subunit is substituted by Tyr, 37th Phe in the β-subunit is substituted by Leu, 108th Glu in the β-subunit is substituted by Asp, and 200th Ala in the β-subunit is substituted by Glu;

(au) 19th Ala in the α-subunit is substituted by Val, 71st Arg in the α-subunit is substituted by His, 126th Phe in the α-subunit is substituted by Tyr, 37th Phe in the β-subunit is substituted by Val, 108th Glu in the β-subunit is substituted by Asp, and 200th Ala in the β-subunit is substituted by Glu;

(av) 36th Thr in the α-subunit is substituted by Met, 148th Gly in the α-subunit is substituted by Asp, 204th Val in the α-subunit is substituted by Arg, 41st Phe in the β-subunit is substituted by Ile, 51st Phe in the β-subunit is substituted by Val, and 108th Glu in the β-subunit is substituted by Asp;

(aw) 148th Gly in the α-subunit is substituted by Asp, 204th Val in the α-subunit is substituted by Arg, 108th Glu in the β-subunit is substituted by Asp, and 200th Ala in the β-subunit is substituted by Glu;

(ax) 36th Thr in the α-subunit is substituted by Gly, and 188th Thr in the α-subunit is substituted by Gly;

(ay) 36th Thr in the α-subunit is substituted by Ala, and 48th Asn in the α-subunit is substituted by Gln;

(az) 48th Asn in the α-subunit is substituted by Glu, and 146th Arg in the β-subunit is substituted by Gly;

(ba) 36th Thr in the α-subunit is substituted by Trp, and 176th Tyr in the β-subunit is substituted by Cys;

(bb) 176th Tyr in the β-subunit is substituted by Met, and 217th Asp in the β-subunit is substituted by Gly;

(bc) 36th Thr in the α-subunit is substituted by Ser, and 33rd Ala in the β-subunit is substituted by Val;

(bd) 176th Tyr in the β-subunit is substituted by Ala, and 217th Asp in the β-subunit is substituted by Val;

(be) 40th Thr in the β-subunit is substituted by Val, and 218th Cys in the β-subunit is substituted by Met;

(bf) 33rd Ala in the β-subunit is substituted by Met, and 176th Tyr in the β-subunit is substituted by Thr;

(bg) 40th Thr in the β-subunit is substituted by Leu, and 217th Asp in the β-subunit is substituted by Leu;

(bh) 40th Thr in the β-subunit is substituted by Ile, and 61st Ala in the β-subunit is substituted by Val;

(bi) 61st Ala in the β-subunit is substituted by Thr, and 218th Cys in the β-subunit is substituted by Ser;

(bj) 112th Lys in the β-subunit is substituted by Val, and 217th Asp in the β-subunit is substituted by Met;

(bk) 61st Ala in the β-subunit is substituted by Trp, and 217th Asp in the β-subunit is substituted by His;

(bl) 61st Ala in the β-subunit is substituted by Leu, and 112th Lys in the β-subunit is substituted by Ile;

(bm) 146th Arg in the β-subunit is substituted by Gly, and 217th Asp in the β-subunit is substituted by Ser;

(bn) 171st Lys in the β-subunit is substituted by Ala, and 217th Asp in the β-subunit is substituted by Thr;

(bo) 150th Ala in the β-subunit is substituted by Ser, and 217th Asp in the β-subunit is substituted by Cys;

(bp) 61st Ala in the β-subunit is substituted by Gly, and 150th Ala in the β-subunit is substituted by Asn;

(bq) 61st Ala in the β-subunit is substituted by Ser, and 160th Arg in the β-subunit is substituted by Met; and (br) 160th Arg in the β-subunit is substituted by Cys, and 168th Thr in the β-subunit is substituted by Glu.

A nitrile hydratase variant including substitution of at least one amino acid selected from the above amino acid substitutions, and having the nitrile hydratase activity may be used.

As the nitrile hydratase of this embodiment, a transformant transformed so as to produce nitrile hydratase may be used. The transformant can be produced by cloning a gene encoding a nitrile hydratase registered on a gene database GenBank or the like into the expression vector. The transformant producing the nitrile hydratase can be prepared in the same manner as in the transformant producing amidase described in the first embodiment.

In this embodiment, a reaction for converting 3-mercaptopropionitrile or a salt thereof to 3-mercaptopropionamide or a salt thereof (hereinafter referred to as the first reaction) and a method for converting 3-mercaptopropionamide to a 3-mercaptopropionic acid (hereinafter referred to as the second reaction) can be separately carried out, can be carried out at the same time, or the second reaction can be carried out by isolating and purifying 3-mercaptopropionamide after completion of the first reaction.

In this method, the first reaction and the second reaction may be separately carried out, or a 3-mercaptopropionic acid may be produced in one pot by adding both nitrile hydratase and amidase to 3-mercaptopropionitrile. One pot mentioned herein indicates that several reactions are carried out in the same reaction vessel, and specifically refers to the first reaction and the second reaction represented by the reaction formula (8).

3-mercaptopropionitrile becomes a catalyst poison because of the enzyme in some cases. For example, Patent Document 5 discloses that β-substituted propylnitrile is generally a biologically toxic compound, 0.5 to 10 weight % of β-substituted propionitrile is used in the enzymatic method, and it is preferable to control the concentration of a substrate because of toxicity of the substrate. Thus, the use of an enzyme highly stable relative to 3-mercaptopropionitrile is favorable in order to produce the product industrially, because the reaction yield is improved and the amount of the enzyme in use is reduced. With the use of a nitrile hydratase and amidase highly stable relative to 3-mercaptopropionitrile, the first reaction and the second reaction may be carried out the same time. Examples of the nitrile hydratase and amidase highly stable relative to 3-mercaptopropionitrile include nitrile hydratases derived from a bacterium belonging to the genus *Pseudonocardia* and a group of amidases called the AS family.

The second reaction can be carried out after the first reaction is completed for the purpose of avoiding the catalyst poison of 3-mercaptopropionitrile. Examples of the nitrile hydratase highly stable relative to 3-mercaptopropionitrile include nitrile hydratases derived from a bacterium belonging to the genus *Pseudonocardia*. Addition of amidase may be performed after fully completion of the first reaction or after decrease of 3-mercaptopropionitrile in the first reaction to the extent that the second reaction is not hindered.

As the amidase used in the second reaction, there may be used a group of amidases called the AS family having the amidase active center of lysine, serine and serine. More specifically, there are cited amidases derived from *Pseudomonas*

*putida* NBRC12668, *Pseudonocardia thermophila* JCM3095, *Pseudomonas chlororaphis* B23 and *Acidiphilium crytum* JF-5. More preferably used are amidases derived from *Pseudomonas putida* NBRC12668 and *Pseudonocardia thermophila* JCM3095. The by-product generated in the production reaction of 3-mercaptopropionitrile causes a decrease of the amidase activity in some cases. However, amidase derived from *Pseudomonas putida* NBRC12668 is less susceptible to a decrease of the activity in the reaction system represented by the reaction formula (8). Accordingly, the reaction represented by the reaction formula (8) may be carried out while the purification procedure of 3-mercaptopropionitrile is simplified or is not carried out. Incidentally, the amino acid sequence and the DNA sequence of amidase derived from *Pseudomonas putida* NBRC12668 are respectively set forth in SEQ ID Nos: 1 and 2 in the Sequence Listing.

As the condition in the first reaction, the temperature is preferably from 0 to 50 degrees centigrade and more preferably from 0 to 40 degrees centigrade. The reaction pH is from 3.0 to 10.0 and preferably from 6.0 to 8.0. As the acid used for adjusting the pH, there may be used mineral acids such as hydrochloric acid, sulfuric acid, phosphoric acid and the like; and organic acids such as acetic acid and the like. As the reaction solvent, there may be used water; alcohols such as methanol, ethanol and the like; fatty acid esters such as ethyl acetate, butyl acetate and the like; and aromatic compounds such as toluene, xylene and the like, but particularly preferably used is water. The concentration of 3-mercaptopropionitrile in the reaction solution is preferably equal to or more than 1 weight %, industrially favorably equal to or more than 11 weight %, and further preferably equal to or more than 13 weight %. The concentration of 3-mercaptopropionitrile in the reaction solution is equal to or less than 50 weight %, and more preferably equal to or less than 17 weight %. The reaction solution mentioned in this paragraph refers to any of 3-mercaptopropionitrile as a reaction substrate dissolved in a reaction solvent, 3-mercaptopropionitrile dispersed in a reaction solvent, and 3-mercaptopropionitrile phase-separated from a reaction solvent. The concentration mentioned herein refers to a concentration when 3-mercaptopropionitrile is all dissolved in a reaction solvent, and actually 3-mercaptopropionitrile may be fully dissolved in a reaction solvent, or may not be dissolved. The reaction time is usually about 1 to 80 hours.

As the reaction condition when the first reaction and the second reaction are carried out at the same time in one pot, the temperature is preferably from 0 to 50 degrees centigrade, more preferably from 0 to 40 degrees centigrade, and further preferably from 15 to 30 degrees centigrade. The reaction pH is from 3.0 to 10.0 and preferably from 6.0 to 8.0. As the acid used for adjusting the pH, there may be used mineral acids such as hydrochloric acid, sulfuric acid, phosphoric acid and the like; and organic acids such as acetic acid and the like. As the reaction solvent, there may be used water; alcohols such as methanol, ethanol and the like; fatty acid esters such as ethyl acetate, butyl acetate and the like; and aromatic compounds such as toluene, xylene and the like, but particularly preferably used is water. The concentration of 3-mercaptopropionitrile in the reaction solution is preferably equal to or more than 1 weight %, industrially favorably equal to or more than 11 weight %, and further preferably equal to or more than 13 weight %. The concentration of 3-mercaptopropionitrile in the reaction solution is equal to or less than 50 weight %, and more preferably equal to or less than 17 weight %. The reaction solution mentioned in this paragraph refers to any of 3-mercaptopropionitrile as a reaction substrate and 3-mercaptopropionamide as a reaction intermediate dissolved in a reaction solvent, 3-mercaptopropionitrile and 3-mercaptopropionamide dispersed in a reaction solvent, and 3-mercaptopropionitrile and 3-mercaptopropionamide phase-separated from a reaction solvent. The concentration mentioned herein refers to a concentration when 3-mercaptopropionitrile is all dissolved in a reaction solvent, and 3-mercaptopropionitrile may be actually fully dissolved in a reaction solvent, or may not be dissolved. The reaction time is usually from about 1 to 80 hours.

The amidase used in this embodiment may be the same as amidase described in the first embodiment. Furthermore, the reaction conditions of the 3-mercaptopropionamide and the isolation method of 3-mercaptopropionic acid may be the same as those described in the first embodiment.

The method of this embodiment has, in addition to operational effects described in the first embodiment, the following operational effects. That is, a 3-mercaptopropionic acid can be produced from 3-mercaptopropionitrile through the two-stage enzymatic reaction. Accordingly, the 3-mercaptopropionic acid can be produced under mild conditions, and burden on the environment can be further reduced.

Also, in this embodiment, the 3-mercaptopropionic acid to be obtained can be separated by the solvent extraction. A preferable solvent is a suitable polar organic solvent which dissolves a carboxyl group of a product and is not mixed with water. Preferable examples of such a solvent include methyl acetate, butyl acetate, methyl isobutyl ketone, methylene chloride, methyl ethyl ketone, methyl isobutyl ketone and the like. Furthermore, the 3-mercaptopropionic acid may be isolated using a general method by distillation or the like. In this embodiment, since the purity of the 3-mercaptopropionic acid to be obtained is high, the 3-mercaptopropionic acid may be isolated without through the complicated purification procedure such as distillation or the like. For example, since the 3-mercaptopropionic acid and water are separated by the addition of an acid to the reaction solution, the 3-mercaptopropionic acid can be obtained only by recovering the 3-mercaptopropionic acid phase. In this case, as the acid, suitably used are mineral acids such as hydrochloric acid, sulfuric acid, phosphoric acid and the like.

Third Embodiment

In this embodiment, 3-mercaptopropionitrile or a salt thereof, and 3-mercaptopropionamide or a salt thereof are produced by reacting acrylonitrile with a compound containing a sulfur atom, and a 3-mercaptopropionic acid is produced in the coexistence of amidase and nitrilase with the use of the obtained 3-mercaptopropionitrile and 3-mercaptopropionamide or a salt thereof. This reaction formula is represented by the following reaction formula (9),

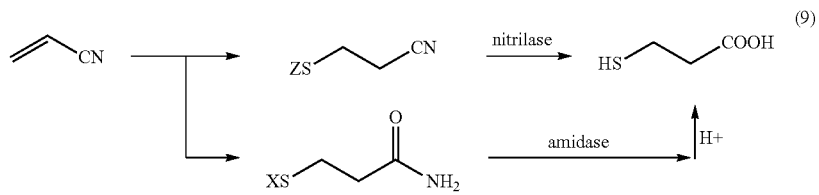

In this embodiment, 3-mercaptopropionitrile or a salt thereof is the same as the 3-mercaptopropionitrile derivative represented by the general formula (3) used in the second embodiment. The 3-mercaptopropionamide salt may be the same as the 3-mercaptopropionamide derivative represented by the general formula (1) used in the second embodiment. The 3-mercaptopropionic acid can be obtained as carboxylate or thiolate having a counter ion corresponding to the 3-mercaptopropionitrile salt.

The compound containing a sulfur atom can be selected from sulfide, hydrosulfide, thiosulfuric acid, aliphatic thiocarboxylic acid having 1 to 12 carbon atoms (for example, thioacetic acid), thioxanthogen and an alkali metal salt, an alkali earth metal salt, a magnesium salt or an ammonium salt thereof, and thiourea. As the alkali metal salt, particularly preferably used are sodium salts and potassium salts. As the alkali earth metal salt, particularly preferably used are calcium salts and barium salts. As the compound containing a sulfur atom, particularly preferably used is sodium hydrogen sulfide. As a method for producing an alkali metal salt of 3-mercaptopropionitrile by reacting acrylonitrile with a compound containing a sulfur atom, there may be used a known method.

As the 3-mercaptopropionitrile salt, more preferably used is a monovalent cation. It is preferable to reduce hydrogen sulfide which is present in the produced reaction solution before supplying the 3-mercaptopropionitrile thus prepared to the enzymatic reaction. As a method of removing hydrogen sulfide, hydrogen sulfide may be reduced by a method of reducing the pressure after neutralization, a method of bubbling with nitrogen or the like, or a method in combination thereof. The concentration of hydrogen sulfide is preferably equal to or less than 50 ppm, more preferably equal to or less than 20 ppm, and further preferably equal to or less than 15 ppm. Incidentally, the concentration of hydrogen sulfide may be measured by known head-space gas chromatography.

Nitrilase refers to an enzyme acting on a nitrile group in a nitrile compound, and hydrolyzing the nitrile group to give a carboxyl group. The nitrilase used in this embodiment may be any of nitrilases originated from microorganisms, plants, molds, animals, insects and the like so long as 3-mercaptopropionitrile is efficiently hydrolyzed.

Examples of the microorganism known to produce nitrilase include microorganisms belonging to *Corynebacterium* genus, *Nocardia* genus, *Pseudomonas* genus, *Bacillus* genus, *Bacteridium* genus, *Brevibacterium* genus, *Micrococcus* genus, *Rhodococcus* genus, *Aeromonas* genus, *Citrobacter* genus, *Agrobacterium* genus, *Erwinia* genus, *Enterobacter* genus, *Streptomyces* genus, *Rhizobium* genus, *Pseudonocardia* genus and the like.

The nitrilase is commercially available as a reagent, and nitrilase capable of efficiently hydrolyzing 3-mercaptopropionitrile among such products may also be used. For example, 12 kinds of nitrilases (Catalog No. NIT-12000) having different origins may be used, which are commercially available from BioCatalytics Inc.

As the nitrilase of this embodiment, a transformant transformed so as to produce nitrilase may be used. The transformant can be produced by cloning a gene encoding a nitrilase registered on a gene database GenBank or the like into the expression vector. The transformant producing the nitrilase can be produced in the same manner as in the transformant producing amidase described in the first embodiment.

The reaction conditions of 3-mercaptopropionitrile may be the same as those described in the second embodiment. The reaction conditions of 3-mercaptopropionamide may be the same as those described in the first embodiment.

3-mercaptopropionitrile and 3-mercaptopropionamide obtained from acrylonitrile and a compound containing a sulfur atom may be isolated, and respectively reacted in a separate reaction vessel.

3-mercaptopropionitrile and 3-mercaptopropionamide obtained from acrylonitrile and a compound containing a sulfur atom may be used in a mixed state without isolating, and reacted with the addition of nitrilase and amidase.

When 3-mercaptopropionitrile and 3-mercaptopropionamide obtained from acrylonitrile and a compound containing a sulfur atom are used in a mixed state without isolating, and reacted with the addition of nitrilase and amidase, nitrile hydratase used in the second embodiment may be added together with nitrilase and amidase. As the reaction condition in this case, the temperature is preferably from 0 to 50 degrees centigrade and more preferably from 0 to 40 degrees centigrade. The reaction pH is 3.0 to 10.0 and preferably 6.0 to 8.0. As the acid used for adjusting the pH, there may be used mineral acids such as hydrochloric acid, sulfuric acid, phosphoric acid and the like; and organic acids such as acetic acid and the like. As the reaction solvent, there may be used water; alcohols such as methanol, ethanol and the like; fatty acid esters such as ethyl acetate, butyl acetate and the like; and aromatic compounds such as toluene, xylene and the like, but particularly preferably used is water. The concentration of 3-mercaptopropionitrile is preferably equal to or more than 1 weight %, industrially favorably equal to or more than 11 weight %, and further preferably equal to or more than 13 weight %. The concentration of 3-mercaptopropionitrile is equal to or less than 50 weight %, and more preferably equal to or less than 17 weight %. The concentration mentioned herein refers to a concentration when 3-mercaptopropionitrile is all dissolved in a reaction solvent, and 3-mercaptopropionitrile may be actually fully dissolved in a reaction solvent, or may not be dissolved. The reaction time is usually about 1 to 80 hours.

In the production of 3-mercaptopropionitrile and 3-mercaptopropionamide obtained from acrylonitrile and a compound containing a sulfur atom, 3,3'-dithiodipropiononitrile and 3,3'-dithiodipropionamide are partly produced. These disulfide compounds are subjected to hydrolysis by nitrilase and amidase to produce a 3,3'-dithiodipropionic acid. The produced 3,3'-dithiodipropionic acid can be converted to a 3-mercaptopropionic acid by a usually known reduction method such as addition of metal powder of zinc, iron or the like under acidic conditions.

A method of isolating the 3-mercaptopropionic acid in use may be the same as the method described in the first embodiment.

The method of this embodiment has, in addition to operational effects described in the first embodiment, the following operational effects. That is, in the reaction of acrylonitrile with a compound containing a sulfur atom, 3-mercaptopropionitrile is obtained as a main product (about 80%), while 3-mercaptopropionamide (about 15%) and 3-mercaptopropionic acid are obtained as the by-products. In this embodiment, nitrilase and amidase act on the reaction product of acrylonitrile and a compound containing a sulfur atom. Thus, the 3-mercaptopropionic acid can be obtained from acrylonitrile with a good yield.

As shown in this embodiment, even when nitrilase is used along with amidase, the yield of the by-product composed of a thiodipropionic acid may be equal to or less than 10 mole %. By properly selecting the kind of amidase, it may be equal to or less than 5 mole % and more preferably equal to or less than 1 mole %. Accordingly, the 3-mercaptopropionic acid can be obtained with high purity without through the complicated purification procedure such as distillation or the like. Incidentally, the yield of the above by-product in this embodiment is determined from the following numerical equation (10), Yield of by-product(%)=[substance amount (mole) of thiodipropionic acid/substance amount (mole) of acrylonitrile]×100 (10)

In this embodiment, in addition to amidase and nitrilase, a nitrile hydratase may be further used. In this case, the amount of amidase added is preferably adjusted in consideration of the amount of reacting to 3-mercaptopropionamide produced by the reaction of acrylonitrile with a compound containing a sulfur atom, and the amount of reacting to 3-mercaptopropionamide produced by the action of nitrile hydratase. The nitrile hydratase is resistant against the by-product produced by the production reaction of 3-mercaptopropionitrile. Thus, the reaction may efficiently proceed with a smaller amount of the enzyme as compared to nitrilase.

Fourth Embodiment

In this embodiment, as described in the third embodiment, 3-mercaptopropionitrile or a salt thereof, and 3-mercaptopropionamide or a salt thereof, shown in the second embodiment, are produced by reacting acrylonitrile with a compound containing a sulfur atom. A nitrile group of the obtained 3-mercaptopropionitrile or a salt thereof is hydrolyzed by nitrile hydratase to give 3-mercaptopropionamide or a salt thereof, and the 3-mercaptopropionic acid is obtained from the 3-mercaptopropionamide or the salt thereof by amidase. The reaction of this embodiment is represented by the reaction formula (11), taining a sulfur atom may be isolated, and respectively reacted in a separate reaction vessel.

3-mercaptopropionitrile and 3-mercaptopropionamide obtained from acrylonitrile and a compound containing a sulfur atom may be used in a mixed state without isolating, and reacted with the addition of nitrile hydratase and amidase.

It is preferable to reduce hydrogen sulfide which is present in the produced reaction solution before supplying 3-mercaptopropionitrile to the enzymatic reaction. As a method of removing hydrogen sulfide, the concentration of hydrogen sulfide may be reduced by a method of reducing the pressure after neutralization, a method of bubbling with nitrogen or the like, or a method in combination thereof. The concentration of hydrogen sulfide is preferably equal to or less than 50 ppm, more preferably equal to or less than 20 ppm, and further preferably equal to or less than 15 ppm. Incidentally, the concentration of hydrogen sulfide may be measured by known head-space gas chromatography.

The nitrile hydratase in use may be the same as nitrile hydratase used in the second embodiment.

The amidase in use may be the same as amidase used in the first embodiment, but preferably used are a group of amidases called the AS family having the amidase active center of lysine, serine and serine. More specifically, there are cited amidases derived from *Pseudomonas putida* NBRC12668, *Pseudonocardia thermophila* JCM3095, *Pseudomonas chlororaphis* B23 and *Acidiphilium crytum* JF-5. More preferably used are amidases derived from *Pseudomonas putida* NBRC12668 and *Pseudonocardia thermophila* JCM3095.

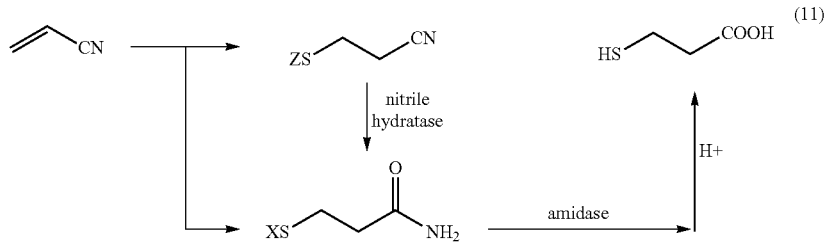

Also, in this embodiment, 3-mercaptopropionitrile or a salt thereof, and 3-mercaptopropionamide salt in use may be the same as those in the third embodiment. The 3-mercaptopropionic acid can be obtained as a carboxylic acid salt or thiolate corresponding to the 3-mercaptopropionitrile salt.

The reaction represented by the reaction formula (11) may be carried out in one pot. One pot mentioned herein indicates that several reactions are carried out in the same reaction vessel, and specifically indicates that a reaction of producing 3-mercaptopropionitrile as a main product from acrylonitrile and a compound containing a sulfur atom, and producing 3-mercaptopropionamide as a by-product, an amidation reaction of 3-mercaptopropionitrile, and a hydrolysis reaction of 3-mercaptopropionamide are continuously carried out. In this case, the compound containing a sulfur atom in use may be the same as that described in the third embodiment.

Specifically, 3-mercaptopropionitrile and 3-mercaptopropionamide obtained from acrylonitrile and a compound con- Fifth Embodiment In this embodiment, 3-mercaptopropionitrile represented by the above general formula (3) or a salt thereof is produced by reacting acrylonitrile with a compound containing a sulfur atom, and a 3-mercaptopropionic acid represented by the above general formula (2) is produced in the coexistence of nitrile hydratase and amidase with the use of the obtained 3-mercaptopropionitrile or the salt thereof. One example of the reaction formula is represented by the following reaction formula (12). In the reaction formula (12), a thiol group may be thiolate, while a carboxyl group may be carboxylate. Examples of the counter cation include monovalent cations such as alkali metal ion and ammonium ion. Examples of the alkali metal ion include $Li^+$, $Na^+$, $K^+$, $Rb^+$ and $Cs^+$. Examples of the divalent cation include $Be^{2+}$, $Mg^{2+}$, or alkali earth metal ion such as $Ca^{2+}$, $Sr^{2+}$, $Ba^{2+}$ and $Ra^{2+}$. As the trivalent cation, $Al^{3+}$ is cited.

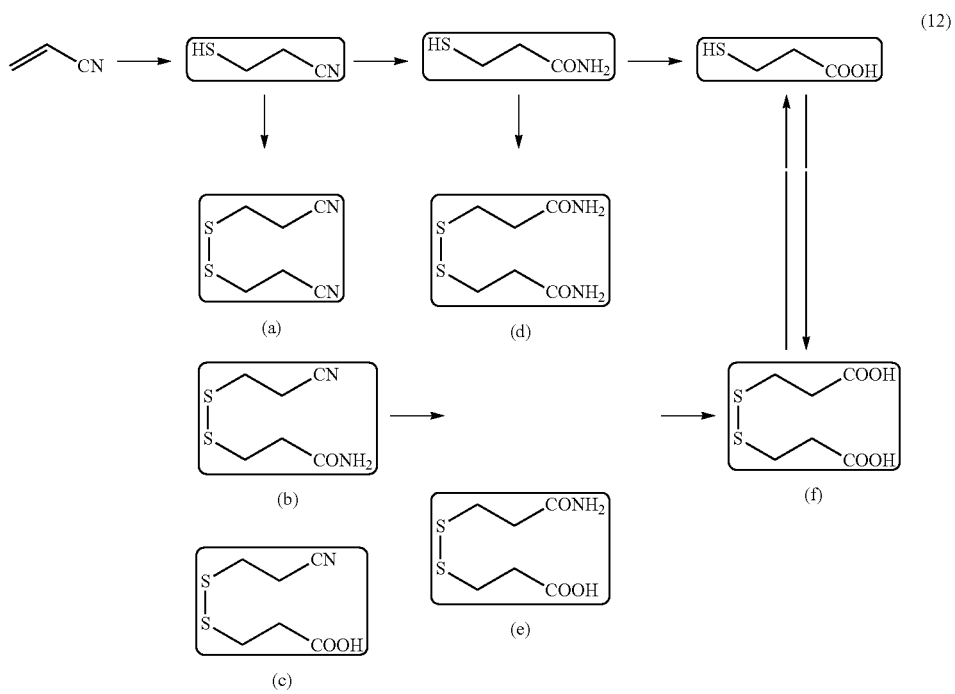

(12)

Specifically, in this embodiment, the 3-mercaptopropionitrile or the salt thereof may be the same as the 3-mercaptopropionitrile derivative represented by general formula (3) used in the second embodiment. The 3-mercaptopropionitrile or the salt thereof may be converted to the 3-mercaptopropionamide derivative represented by the general formula (1) described in the second embodiment by nitrile hydratase.

As described in the third embodiment, 3-mercaptopropionitrile or a salt thereof, and 3-mercaptopropionamide or a salt thereof can be produced by reacting acrylonitrile with a compound containing a sulfur atom. Thiol forms a disulfide bond by an oxidative coupling reaction between molecules. Accordingly, 2 molecules of 3-mercaptopropionitrile form a disulfide bond to give 3,3'-dithiodipropiononitrile (compound (a)), 2 molecules of 3-mercaptopropionamide form a disulfide bond to give 3,3'-dithiodipropionamide (compound (d)), and 1 molecule of 3-mercaptopropionitrile and 1 molecule of 3-mercaptopropionamide form a disulfide bond to give 3-(2-cyanoethyl)disulfanylpropanamide (compound (b)).

The compound (a) is converted to the compounds (b) and (d) by hydrolyzing a nitrile group to an amide group by nitrile hydratase. The 3-mercaptopropionitrile is converted, as described in the second embodiment, to 3-mercaptopropionamide by nitrile hydratase to give the compound (d) by an oxidative coupling reaction between molecules as described above.

The compounds (b) and (d) form cyanopropiodisulfanylpropiocarboxylic acid (compound (c)), an aminocarbonylpropiosulfanylpropiocarboxylic acid (compound (e)), and a 3,3'-dithiodipropionic acid (compound (f)) by hydrolyzing an amide group by amidase.

It is possible that the 3-mercaptopropionitrile and 3-mercaptopropionic acid form a disulfide bond to give the compound (c), and the 3-mercaptopropionamide and 3-mercaptopropionic acid form a disulfide bond to give the compound (e).

The compound (c) is converted to the compound (e) by nitrile hydratase, while the compound (e) is converted to the compound (f) by amidase. Accordingly, in addition to the desired 3-mercaptopropionic acid, the compound (f) is obtained by completely reacting 3-mercaptopropionitrile in the coexistence of nitrile hydratase and amidase. The produced 3,3'-dithiodipropionic acid can be converted to a 3-mercaptopropionic acid by reducing according to a known method. Thus, in this embodiment, the 3-mercaptopropionic acid can be efficiently produced by skipping purification in the middle of each step represented by the above reaction formula (12).

3,3'-dithiodipropiononitrile and 3,3'-dithiodipropionamide can be produced by oxidizing a reactant of acrylonitrile and a compound containing a sulfur atom described in the third embodiment according to a known method.

The nitrile hydratase used in this embodiment may be the nitrile hydratase described in the third embodiment. The amidase used in this embodiment may be the amidase described in the third embodiment.

The reaction conditions of 3,3'-dithiodipropiononitrile may be the same as those described in the second embodiment. The reaction conditions of 3,3'-dithiodipropionamide may be those described in the first embodiment.

3,3'-dithiodipropiononitrile and 3,3'-dithiodipropionamide may be used in a mixed state without isolating, and reacted with the addition of nitrile hydratase and amidase.

It is preferable to reduce the concentration of hydrogen sulfide which is present in the produced reaction solution before supplying 3,3'-dithiodipropiononitrile and 3,3'-dithiodipropionamide to the enzymatic reaction. As a method of removing hydrogen sulfide, the concentration of hydrogen sulfide may be reduced by a method of reducing the pressure after neutralization, a method of bubbling with nitrogen or the like, or a method in combination thereof. The concentration of hydrogen sulfide is preferably equal to or less than 50 ppm, more preferably equal to or less than 20 ppm, and further preferably equal to or less than 15 ppm. Incidentally, the concentration of hydrogen sulfide may be measured by known head-space gas chromatography.

As the reaction condition, the temperature is preferably 0 to degrees centigrade and more preferably 0 to 40 degrees centigrade. The reaction pH is 3.0 to 10.0 and preferably 6.0 to 8.0. As the acid used for adjusting the pH, there may be used mineral acids such as hydrochloric acid, sulfuric acid, phosphoric acid and the like; and organic acids such as acetic acid and the like. As the reaction solvent, there may be used water; alcohols such as methanol, ethanol and the like; fatty acid esters such as ethyl acetate, butyl acetate and the like; and aromatic compounds such as toluene, xylene and the like, but particularly preferably used is water. The concentration of 3,3'-dithiodipropiononitrile and 3,3'-dithiodipropionamide in the reaction solution is preferably equal to or more than 1 weight %, industrially favorably equal to or more than 11 weight %, and further preferably equal to or more than 13 weight %. The reaction solution mentioned in this paragraph refers to any of 3,3'-dithiodipropiononitrile or 3,3'-dithiodipropionamide as a reaction substrate dissolved in a reaction solvent, 3,3'-dithiodipropiononitrile or 3,3'-dithiodipropionamide dispersed in a reaction solvent, and 3,3'-dithiodipropiononitrile or 3,3'-dithiodipropionamide phase-separated from a reaction solvent. The concentration mentioned herein refers to a concentration when 3,3'-dithiodipropiononitrile and 3,3'-dithiodipropionamide are all dissolved in a reaction solvent, and 3,3'-dithiodipropiononitrile and 3,3'-dithiodipropionamide may be actually fully dissolved in a reaction solvent, or may not be dissolved. The reaction time is usually about 1 to 80 hours.

The produced 3,3'-dithiodipropionic acid can be converted to a 3-mercaptopropionic acid by a usually known reduction method such as addition of metal powder of zinc, iron or the like under acidic conditions.

A method of isolating the 3-mercaptopropionic acid in use may be the same as the method described in the first embodiment.

As described above, the embodiments of the present invention have been described, but the embodiments are examples of the present invention and other various constructions can also be adopted.

For example, the 3-mercaptopropionic acid obtained according to the method of the embodiment and pentaerythritol may be subjected to an esterification reaction to produce pentaerythritol tetrakis(3-mercaptopropionate). A known method may be used for this esterification reaction. The pentaerythritol tetrakis(3-mercaptopropionate) thus obtained may be monopolymerized or copolymerized, followed by curing, and may be used as an optical material of a plastic lens or the like. In the present invention, the 3-mercaptopropionic acid and 3-mercaptopropionic acid are the same compound, while the dithiodipropionic acid, β,β-dithiodipropionic acid and 3,3'-dithiodipropionic acid are the same compound.

EXAMPLES

1. Construction of Amidase-Producing Bacteria
(1) Amidase-Producing Bacteria of *Pseudomonas putida* NBRC12668

The base sequence of plasmid pBAN-7 disclosed in Japanese Laid-open Patent Publication No. Hei 8 (1996)-266277 was analyzed. Based on the base sequence of the plasmid, primers having the sequence as set forth in SEQ ID Nos: 7 and 8 in the Sequence Listing were designed. Using a chromosomal DNA of *Pseudomonas putida* NBRC12668 as the template, PCR was carried out to amplify an amidase gene. The amplified gene was digested with EcoRI and HindIII. In the same manner, pUC18 (manufactured by Takara Shuzo Co., Ltd.) digested with restriction enzymes was ligated using Ligation High (manufactured by Toyobo Co., Ltd.), and introduced into Competent High DH5α (manufactured by Toyobo Co., Ltd.) to produce an amidase-producing bacteria of *Pseudomonas* putidaNBRC12668. This bacteria is referred to as "Ppu-amidase-producing bacteria".

(2) Amidase-Producing Bacteria of *Pseudonocardia thermophila* JCM3095

The base sequence of plasmid pPT-B1 disclosed in Japanese Laid-open Patent Publication No. Hei 9 (1997)-275978 was analyzed. Based on the base sequence of the plasmid, primers having the sequence as set forth in SEQ ID Nos: 9 and 10 in the Sequence Listing were designed. Using a chromosomal DNA of *Pseudonocardia thermophila* JCM3095 as the template, PCR was carried out to amplify an amidase gene. The amplified gene was digested with EcoRI and HindIII. In the same manner, pUC18 (manufactured by Takara Shuzo Co., Ltd.) digested with restriction enzymes was ligated using Ligation High (manufactured by Toyobo Co., Ltd.), and introduced into Competent High DH5α (manufactured by Toyobo Co., Ltd.) to produce an amidase-producing bacteria of *Pseudonocardia thermophila* JCM3095. This bacteria is referred to as "Pth-amidase-producing bacteria".

(3) Amidase-Producing Bacteria of *Pseudomonas chlororaphis* B23

DNA was synthesized on the basis of amidase gene information of *Pseudomonas chlororaphis* B23 registered with National Center for Biotechnology Information (NCIBM). Synthesis of DNA was carried out according to a method of Nucleic Acids Res. 2004 Jul. 1; 32 (Web Server issue): W176-80. Using the synthesized DNA as the template and the primers having the sequence as set forth in SEQ ID Nos: 11 and 12 in the Sequence Listing, DNA with the SD sequence added to the amidase gene was amplified, and the amplified DNA was digested with restriction enzymes EcoRI and HindIII. In the same manner, pUC18 (manufactured by Takara Shuzo Co., Ltd.) digested with restriction enzymes was ligated using Ligation High (manufactured by Toyobo Co., Ltd.), and introduced into Competent High DH5α (manufactured by Toyobo Co., Ltd.) to produce an amidase-producing bacteria of *Pseudomonas chlororaphis* B23. This bacteria is referred to as "Pch-amidase-producing bacteria".

(4) Amidase-Producing Bacteria of *Polaromonas* sp.JS666

ATCC-BAA-500D-5, a chromosomal DNA of *Polaromonas* sp. JS666, was purchased from American Type Culture Collection (ATCC). On the basis of amidase gene information of *Polaromonas* sp.JS666 GeneID: 4010994) registered with National Center for Biotechnology Information (NCIBM), using SEQ ID Nos: 13 and 14 in the Sequence Listing as the primer and ATCC-BAA-500D-5 as the template, an amidase gene was amplified. The amplified amidase gene was digested with EcoRI and HindIII. In the same manner, pUC18 (manufactured by Takara Shuzo Co., Ltd.) digested with restriction enzymes was ligated using Ligation High (manufactured by Toyobo Co., Ltd.), and introduced into Competent High DH5α (manufactured by Toyobo Co., Ltd.) to produce an amidase-producing bacteria. This bacteria is referred to as "Psp-amidase-producing bacteria".

(6) Amidase-Producing Bacteria of *Acidphilium cryptum* JF-5

NBRC-14242 was purchased from Biological Resource Center, Department of Biotechnology, National Institute of Technology and Evaluation (NBRC). NBRC-14242 was cultured in a NBRC medium No. 234 to obtain a chromosomal DNA using a DNeasy Blood & Tissue Kit (manufactured by Qiagen Inc.). On the basis of amidase gene information GI: 148259263) registered with National Center for Biotechnology Information (NCIBM), using SEQ ID Nos: 15 and 16 in the Sequence Listing as the primer and the chromosomal DNA obtained by culturing NBRC-14242 as the template, an amidase gene was amplified. The amplified amidase gene was digested with EcoRI and HindIII. In the same manner, pUC18 (manufactured by Takara Shuzo Co., Ltd.) digested with restriction enzymes was ligated using Ligation High (manufactured by Toyobo Co., Ltd.), and introduced into Competent High DH5α (manufactured by Toyobo Co., Ltd.) to produce an amidase-producing bacteria. This bacteria is referred to as "Acr-amidase-producing bacteria".

2. Culture of Amidase-Producing Bacteria

In a 500 ml Erlenmeyer flask with baffles, 100 ml of a liquid LB medium was prepared, and sterilized by autoclaving at 121 degrees centigrade for 20 minutes. Ampicillin was added to this medium to have a final concentration of 100 μg/ml. Subsequently, one platinum loop of the prepared amidase-producing bacteria were inoculated, and cultured at 30 degrees centigrade and 130 rpm for about 20 hours. Only the fungus body was separated from the culture liquid by centrifugal separation (5,000 G for 15 minutes), and then the separated fungus body was again suspended in 5 ml of physiological saline, whereby a fungal suspension was obtained. The fungal suspension was frozen in a freezer, and left to thaw prior to use.

3-1. Construction and Culture of Nitrile Hydratase-Producing Bacteria of *Pseudonocardia thermophila* JCM3095

In a 500 ml Erlenmeyer flask with baffles, 100 ml of a liquid LB medium containing 40 μg/ml of ferric sulfate/heptahydrate and 10 μg/ml of cobalt chloride/dihydrate was prepared, and sterilized by autoclaving at 121 degrees centigrade for 20 minutes. Ampicillin was added to this medium to have a final concentration of 100 μg/ml. Subsequently, one platinum loop of the deposited microorganisms (FERN BP-5785, deposited with the International Patent Organism Depositary at the National Institute of Advanced Industrial Science and Technology, 1-1-1 Higashi, Tsukuba-shi, Ibaraki-ken, Japan, under the deposit number FERN BP-5785, as of February 7, Heisei 8 (1996)) were inoculated, and cultured at 37 degrees centigrade and 130 rpm for about 20 hours. Only the fungus body was separated from the culture liquid by centrifugal separation (5,000 G for 15 minutes), and then the separated fungus body was again suspended in 5 ml of physiological saline, whereby a fungal suspension was obtained. The fungal suspension was frozen in a freezer, and left to thaw prior to use. This bacteria is referred to as "Pth-nitrile hydratase-producing bacteria".

3-2. Construction and Culture of Nitrile Hydratase-Producing Bacteria of *Pseudomonas putida* NBRC12668

Using the chromosomal DNA used in the above 1. Construction of Amidase-Producing Bacteria (1) Amidase-Producing Bacteria of *Pseudomonas putida* NBRC12668 as the template, and SEQ ID Nos: 17 (GTGAATTCACAAAAAG-GATAAAACAATGACGGCAACTTCAACCCC) in the Sequence Listing and SEQ ID No: 18 (TCGAAGCTTTTA-GAAAATGGCATCAGCCG) in the Sequence Listing as the primer, PCR was carried out to amplify a nitrile hydratase gene. The amplified nitrile hydratase gene was digested with EcoRI and HindIII. In the same manner, pUC18 (manufactured by Takara Shuzo Co., Ltd.) digested with restriction enzymes was ligated using Ligation High (manufactured by Toyobo Co., Ltd.), and introduced into Competent High DH5α (manufactured by Toyobo Co., Ltd.) to produce a nitrile hydratase-producing bacteria of *Pseudomonas putida* NBRC12668. This bacteria is referred to as "Ppu-nitrile hydratase-producing bacteria".

In a 500 ml Erlenmeyer flask with baffles, 100 ml of a liquid LB medium containing 40 μg/ml of ferric sulfate/heptahydrate was prepared, and sterilized by autoclaving at 121 degrees centigrade for 20 minutes. Ampicillin was added to this medium to have a final concentration of 100 μg/ml. Subsequently, one platinum loop of the Ppu-nitrile hydratase-producing bacteria were inoculated, and cultured at 37 degrees centigrade and 130 rpm for about 20 hours. Only the fungus body was separated from the culture liquid by centrifugal separation (5,000 G for 15 minutes), and then the separated fungus body was again suspended in 5 ml of physiological saline, whereby a fungal suspension was obtained. The fungal suspension was frozen in a freezer, and left to thaw prior to use.

4. Synthesis of Mercaptopropionitrile 3-mercaptopropionitrile used in each of Examples 1 to 4, 7 to 27, 32, and Comparative Example was synthesized in the following manner. 43.5 g of water was added to 48.1 g (0.6 mole) of 70% sodium hydrogen sulfide and dissolved, and then 26.5 g (0.5 mole) of acrylonitrile was added dropwise thereto for 30 to 60 minutes while keeping the temperature at 40 degrees centigrade. Subsequently, while keeping at 40 degrees centigrade, the mixture was further stirred for 10 hours. Subsequently, about 70 g of 47% aqueous sulfuric acid was added to the obtained reaction mass, the reaction solution pH of equal to or less than 2.0 was confirmed, and then the mixture was extracted with 50 g of chloroform two times. The organic layer was combined and concentrated under reduced pressure, and the residual liquid was distilled under reduced pressure at to 48 degrees centigrade/3 Torr. Thus, 40.3 g of 3-mercaptopropionitrile with a purity of 99.8% was obtained.

5. Analytical Method (1)

With respect to Examples 1 to 29 and Comparative Example, 3-mercaptopropionic acid, 3-mercaptopropionamide, thiodipropionic acid and dithiodipropionic acid were quantitatively analyzed by high performance liquid chromatography (HPLC). The yield of the 3-mercaptopropionic acid was calculated by the numerical equation (13).

Column: Mightysil RP-18 GP 250-6.0 (5 μm) (manufactured by Kanto Chemical Co.; Ltd.)
Column temperature: 40 degrees centigrade
Pump flow rate: 1.0 ml/minute
Detection: UV225 nm
Eluent: 0.01M aqueous $KH_2PO_4$:acetonitrile (AN)=1600:400 (V/V) (phosphoric acid pH: 3.0)

$$\text{Yield of 3-mercaptopropionic acid}(\%) = (\text{substance amount (mole) of 3-mercaptopropionic acid/substance amount (mole) of 3-mercaptopropionamide introduced}) \times 100 \quad (13)$$

6. Synthesis of 3,3'-dithiodipropiononitrile 3,3'-dithiodipropiononitrile used in each of Examples 36 to 38 was synthesized in the following manner. 23.00 g of water was added to 18.39 g (0.21 mole) of 3-mercaptopropionitrile, and cooled down to 5 degrees centigrade. While the temperature of the reaction solution was maintained at 5 to 25 degrees centigrade, 225.4 ml (0.11 mole) of a 0.5 mol/L iodine solution was added dropwise thereto over 1 hour, and then the mixture was aged at 25 degrees centigrade for 2 hours. The solid in the reaction mixture was filtered, and then the filtered solid was washed with 1,800 ml of water, whereby crude 3,3'-dithiodipropiononitrile (a wet product) was obtained. The product was dried overnight at room temperature. Subsequently, the crude 3,3'-dithiodipropiononitrile was sludged with 300 ml of a mixture of n-hexane (300 ml) and n-hexane/toluene (volume ratio: 2/1) one time each for 1 hour, and then was filtered and washed with 500 ml of hexane, to obtain 3,3'-dithiodipropiononitrile (a wet product). Next, the product was dissolved in 650 ml of toluene, and column-filtered (silica gel C-300, 100 ml) to obtain a toluene solution of 3,3'-dithiodipropiononitrile. Toluene was removed under reduced pressure with an evaporator, and the concentrate was added dropwise to 500 ml of hexane and re-precipitated. The crystal was filtered and the filtered crystal was washed with 250 ml of hexane to obtain 10.2 g of 3,3'-dithiodipropiononitrile (a wet product). The product was dissolved again in 650 ml of toluene, and column-filtered (silica gel C-300, 100 ml). Toluene was removed under reduced pressure with an evaporator, and the concentrate was added dropwise to 500 ml of hexane and re-precipitated. The crystal was filtered, and the filtered crystal was washed with 250 ml of hexane and vacuum-dried at room temperature in a desiccator, to obtain 9.0 g of 3,3'-dithiodipropiononitrile.

7. Analytical Method (2)

In each of Examples 30 to 40, 3-mercaptopropionitrile, 3-mercaptopropionamide, 3-mercaptopropionic acid, 3,3'-dithiodipropiononitrile, 3,3'-dithiodipropionamide and 3,3'-dithiodipropionic acid were quantitatively analyzed by HPLC. The sample was dissolved in a mixture of water/acetonitrile (8/2), and benzyl alcohol was used as the internal standard substance for the measurement by high performance liquid chromatography.

I. Device: DGU-14A, LC-10A, SPD-10A, CTO-10A, SCL-10A

Liquid-feeding unit: SCL-10A, manufactured by Shimadzu Corporation

Detector: SPD-10A, manufactured by Shimadzu Corporation

Column oven: CTO-10AxL, manufactured by Shimadzu Corporation

Auto-injector: SIL-10A, manufactured by Shimadzu Corporation

Data processor: Chromatopac C-R5A, manufactured by Shimadzu Corporation

II. Measurement Conditions

Column: Mightysil RP-18 GP 250-6.0 (5 μm) 30 cm

Detector: UV 225 nm

Eluent: 0.01M aqueous $KH_2PO_4$:acetonitrile=1600:400 (V/V) (phosphoric acid pH: 3.0)

Eluent flow rate: 1.0 ml/min

Column oven temperature: 40 degrees centigrade

Sample injection rate: 2 μL

Detection limit: 0.5 weight % (3-mercaptopropionamide, 3-mercaptopropionic acid)

III. Analytical Procedure

About 70 mg of the sample and about 100 mg of benzyl alcohol as the internal standard substance were accurately weighed in a 20 mL sample bottle. 10 mL of a mixture of water and acetonitrile (8:2) was added thereto, mixed and dissolved to give a sample solution. 2 μL of this sample solution was introduced under the aforementioned measurement conditions, and the component peak area was determined from the obtained chromatogram to calculate the purity (%) of the sample.

Example 1

1 g of 3-mercaptopropionitrile was dissolved in 100 mL of a 100 mM potassium phosphate buffer solution (pH 7.5) and the temperature was kept at 4 degrees centigrade. 1 g of the fungal suspension of Pth-nitrile hydratase-producing bacteria was added thereto, and the mixture was stirred for 24 hours. The obtained mixture was analyzed by HPLC and as a result, 99% of 3-mercaptopropionitrile was converted to 3-mercaptopropionamide. Next, the reaction of the reaction formula (4) was carried out. Respective 1 g of the prepared fungal suspensions of the amidase-producing bacteria were added thereto and reacted at 35 degrees centigrade. The yields of the 3-mercaptopropionic acid after a predetermined time were shown in Table 1. In all reactions, the yields of the thiodipropionic acid and dithiodipropionic acid were equal to or less than 5%.

TABLE 1

| | Reaction time/Yield of 3-mercaptopropionionic acid (%) | |
|---|---|---|
| | 2 hours | 24 hours |
| Pth-amidase | >99 | >99 |
| Ppu-amidase | 19 | >99 |
| Acr-amidase | 82 | >99 |
| Pch-amidase | >99 | >99 |
| Psp-amidase | 6 | 78 |

Example 2

The reaction of the reaction formula (8) was carried out. 1.5 g of 3-mercaptopropionitrile was added to 1 g of a 1M phosphate buffer solution (pH 7.5) and distilled water was added thereto to give 9 g. Next, 1 g of the suspension of Pth-nitrile hydratase-producing bacteria and 1 g of the suspension of Pth-amidase-producing bacteria were added thereto, and the mixture was stirred at 25 degrees centigrade for 20 hours. The yield of the 3-mercaptopropionic acid was 99%, while the yield of the dithiodipropionic acid was 0.5%.

Example 3

The reaction of the reaction formula (8) was carried out. 1 g of a 1M phosphate buffer solution (pH 7.5) was added to 4.4 g of 3-mercaptopropionitrile. Distilled water was added to have a final concentration of 3-mercaptopropionitrile of 13 weight %, 15 weight % and 17 weight %, and 1 g of the prepared suspension of Pth-nitrile hydratase-producing bacteria and 1 g of the suspension of Ppu-amidase-producing bacteria were added thereto, and the mixture was stirred at 20 degrees centigrade for 20 hours. The resulting yields of the 3-mercaptopropionic acid were shown in Table 2.

TABLE 2

| Concentration of 3-mercaptopropionitrile (weight %) | Yield (%) |
|---|---|
| 13 | 98 |
| 15 | 97 |
| 17 | 96 |

Example 4

0.1 g of 3-mercaptopropionitrile was added to 1 g of a 1M phosphate buffer solution (pH 7.5), and 9 g of distilled water was added thereto. Next, respective 0.1 g of nitrilase reagents (Catalog Nos. NIT-12000, NIT-1, 2, 3, 4, 5, 7, 8, 9, 10, 11, BioCatalytics Inc.) were added, and the mixture was stirred at 25 degrees centigrade for 20 hours. The reaction solution was analyzed, and the resulting yields of the 3-mercaptopropionic acid were shown in Table 3. In all reactions, the yields of the thiodipropionic acid and dithiodipropionic acid were equal to or less than 5%.

TABLE 3

| Nitrilase | Yield (%) |
|---|---|
| NIT-1 | >99 |
| NIT-2 | >99 |
| NIT-3 | >99 |
| NIT-4 | >99 |
| NIT-5 | >99 |
| NIT-7 | >99 |
| NIT-8 | >99 |
| NIT-9 | >99 |
| NIT-10 | >99 |
| NIT-11 | >99 |

Comparative Example

With respect to the reaction of the reaction formula (11), an amidation reaction of 3-mercaptopropionitrile and a hydrolysis reaction of 3-mercaptopropionamide were chemically carried out without the use of nitrile hydratase and amidase. 174.2 g of distilled water was added to 187.1 g of sodium hydrogen sulfide and heated at 35 degrees centigrade. 106.1 g of acrylonitrile was added, and 3-mercaptopropionitrile was synthesized over 10 hours. 257.3 g of a 46.64 weight % sodium hydroxide solution was added to 472.6 g of the reaction solution to carry out the hydrolysis reaction at 60 degrees centigrade for 10 hours. Next, the temperature was cooled down to room temperature, and sulfuric acid was added to have the pH of 1.8, and the mixture was extracted with chloroform. The composition of the extract was shown in Table 4. Incidentally, the product amount indicates a percentage of the substance amount (mole) of each product relative to the substance amount (mole) of acrylonitrile.

TABLE 4

| Product | Product amount (mole %) |
|---|---|
| 3-mercaptopropionitrile | <0 |
| 3-mercaptopropionic acid | 68 |
| 3-mercaptopropionamide | <0 |
| Thiodipropionic acid | 15 |
| Dithiodipropionic acid | 5 |

Example 5

The reaction of the reaction formula (11) was carried out. 43.5 g of water was added to 48.1 g (0.6 mole) of 70 w/w % sodium hydrogen sulfide (manufactured by Wako Pure Chemical Industries, Ltd.) and dissolved therein, and then 26.5 g (0.5 mole) of acrylonitrile was added dropwise for 30 to 60 minutes while keeping the temperature at 40 degrees centigrade. Subsequently, the mixture was further continuously stirred for 10 hours while keeping the temperature at 40 degrees centigrade. Subsequently, while 47 w/v % aqueous sulfuric acid was added to the obtained reaction mass, the pH of the reaction solution was adjusted to 6.5 to 7.5, whereby a mixture of 3-mercaptopropionitrile, 3-mercaptopropionamide and 3-mercaptopropionic acid was obtained. The composition of the obtained mixture was shown in Table 5. Incidentally, mole % of respective components relative to introduced acrylonitrile were shown in Table 5. Distilled water was added to this mixture, and the pH was adjusted to 7.0 with the use of sulfuric acid and sodium hydroxide. Distilled water was added to have a concentration of 3-mercaptopropionitrile of 13 weight % and 1 g of the suspension of Pth-nitrile hydratase-producing bacteria was added thereto, and the mixture was stirred at 4 degrees centigrade for 24 hours. Next, the reaction solution was heated to 35 degrees centigrade and 1 g of the suspension of Ppu-amidase-producing bacteria was added thereto, and the mixture was stirred for 24 hours. As a result, the yield of the 3-mercaptopropionic acid from the total amount of 3-mercaptopropionitrile and 3-mercaptopropionamide shown in Table 5 was 98%.

TABLE 5

| Component | Composition (mole %/acrylonitrile) |
|---|---|
| 3-mercaptopropionitrile | 88 |
| 3-mercaptopropionic acid | 2 |
| 3-mercaptopropionamide | 6 |
| Thiodipropionic acid | 3 |
| Dithiopropionic acid | <0 |

Example 6

An operation was carried out in the same manner as in Example 5 with the use of the suspension of Pch-amidase-producing bacteria instead of the suspension of Ppu-amidase-producing bacteria. As a result, a 3-mercaptopropionic acid was obtained at a yield of 10%.

Example 7

Production of Highly Concentrated 3-mercaptopropionamide

The reaction of the reaction formula (8) was carried out. 1 g of a 1M phosphate buffer solution (pH 7.5) was added to 4.4 g of 3-mercaptopropionitrile. Distilled water was added to have a final concentration of 3-mercaptopropionitrile of 15 weight %, and 1 g of the prepared suspension of Pth-nitrile hydratase-producing bacteria was added thereto, and reacted at 30 degrees centigrade for 20 hours. Equal to or more than 99% of 3-mercaptopropionitrile was converted to 3-mercaptopropionamide. Next, 1 g of the suspension of amidase-producing bacteria was added thereto, and the mixture was stirred for 20 hours. The resulting yields of the 3-mercaptopropionic acid were shown in Table 6. An electropherogram of the fungal suspension in use is shown in FIG. 1. The density of the bands represented by arrows in FIG. 1 represents the expression level of the enzyme used for the reaction. A is Psp-amidase. B is Acr-amidase, C is Ppu-amidase, and D is Pch-amidase.

TABLE 6

| | Reaction yield (%) |
|---|---|
| Acr-amidase | >99 |
| Ppu-amidase | >99 |
| Pch-amidase | >99 |
| Psp-amidase | 52 |

Example 8

Reaction (1) by Variant Amidase

Using pUC18 containing a gene encoding SEQ ID No: 2 in the Sequence Listing as the template, and primers having the sequence as set forth in SEQ ID Nos: 19 and 20 in the Sequence Listing, a gene encoding a variant with 51st Ile substituted by Thr in the amino acid sequence of SEQ ID No: 1 in the Sequence Listing was prepared by a quick change method. The quick change method was performed according to the protocol manufactured by Stratagene Co. The *Escherichia coli* DH5α cell was transformed with the use of the plasmid prepared by the aforementioned procedure. A variant amidase-producing bacteria was obtained in the same manner as Culture of Amidase-producing Bacteria used in Example 1. The reaction of Example 7 was carried out with the use of a variant amidase. The yield of the obtained 3-mercaptopropionic acid was 99%, while the yield of the dithiodipropionic acid was 0.5%.

Examples 9 to 27

Reaction (2) by Variant Amidase

Using pUC18 containing a gene encoding SEQ ID No: 2 in the Sequence Listing as the template, and primers having the sequence as set forth in SEQ ID Nos: shown in Table 7, a gene encoding a variant with the amino acid substituted as shown in Table 7 in the amino acid sequence of SEQ ID No: 1 in the Sequence Listing was prepared by a quick change method. Other operation was carried out in the same manner as in Example 8. In all variant amidases, the yield of the 3-mercaptopropionic acid was 99%, while the yield of the dithiodipropionic acid was 0.5%.

TABLE 7

| Example | Primer (sequence number) | Amino acid site | Wild | Variant |
|---|---|---|---|---|
| 8 | 19, 20 | 51 | I | T |
| 9 | 21, 22 | 146 | L | V |
| 10 | 23, 24 | 149 | A | G |
| 11 | 25, 26 | 181 | A | S |
| 12 | 27, 28 | 186 | L | I |
| 13 | 29, 30 | 190 | G | T |
| 14 | 31, 32 | 262 | V | A |
| 15 | 33, 34 | 280 | I | V |
| 16 | 35, 36 | 295 | G | A |
| 17 | 37, 38 | 317 | V | I |
| 18 | 39, 40 | 356 | A | G |
| 19 | 41, 42 | 379 | M | L |
| 20 | 43, 44 | 384 | F | Y |
| 21 | 45, 46 | 400 | I | L |
| 22 | 47, 48 | 442 | S | A |
| 23 | 49, 50 | 447 | M | T |
| 24 | 51, 52 | 448 | L | I |
| 25 | 53, 54 | 469 | V | L |
| 26 | 55, 56 | 480 | G | A |
| 27 | 57, 58 | 498 | A | S |

Example 28

Distilled water was added to the mixture of 3-mercaptopropionitrile, 3-mercaptopropionamide and 3-mercaptopropionic acid obtained in Example 5, and the pH was adjusted to 7.0 with the use of sulfuric acid and sodium hydroxide. 0.1 g of the suspension of Pth-nitrile hydratase-producing bacteria or the suspension of Ppu-nitrile hydratase-producing bacteria was added to 5 g of the reaction solution with addition of distilled water to have a concentration of 3-mercaptopropionitrile of 1.0 weight %, and the mixture was stirred at 30 degrees centigrade for 2 hours. In all reactions, equal to or more than 99% of 3-mercaptopropionitrile was hydrolyzed to 3-mercaptopropionamide.

Example 29

36.12 g of water was added to 144.92 g (1.2 mole) of a 46.42 w/v % sodium hydrogen sulfide solution, and 53.06 g (1.0 mole) of acrylonitrile was added dropwise thereto over 1 hour while keeping the temperature at 40 degrees centigrade. Then, the reaction mixture was aged at 40 degrees centigrade for 10 hours. Subsequently, while the temperature of the reaction mixture was maintained at 25 to 30 degrees centigrade, 125.3 g (0.3 mole) of 47 w/v % sulfuric acid was added dropwise thereto over 2 hours (pH: 14→6.5 to 7), and the mixture was aged at from 25 to 30 degrees centigrade for 1 hour. The concentration of hydrogen sulfide in the reaction mixture was analyzed by the head-space gas chromatography method. The concentration of hydrogen sulfide in the aged reaction mixture was 8,000 ppm. Hydrogen sulfide in the reaction mixture was removed under reduced pressure (25 to 30 degrees centigrade, 6.7 kPa (50 torr), 3 hours) until the concentration of hydrogen sulfide in the reaction mixture became 15 ppm. During dropwise addition of sulfuric acid, during aging, during vacuum degassing, hydrogen sulfide gas discharged out of the reaction system was collected using a caustic trap. Next, 75.6 g of the upper crude 3-mercaptopropionitrile and 270.0 g of the lower aqueous layer were acquired from the 2-layer separated reaction mixture by decantation. The acquired crude 3-mercaptopropionitrile and aqueous layer were used at a weight ratio of 75.6:270. Distilled water was added to the obtained mixture of 3-mercaptopropionitrile, 3-mercaptopropionamide and 3-mercaptopropionic acid, and the pH was adjusted to 7.0 with the use of sulfuric acid and sodium hydroxide. 1 g or 2 g of the suspension of Pth-nitrile hydratase-producing bacteria was added to 5 g of the reaction solution, the concentration of 3-mercaptopropionitrile was adjusted to 13 weight %, and the mixture was stirred at from 10 to 30 degrees centigrade for 24 hours. The suspension of Ppu-nitrile hydratase-producing bacteria was added and reacted in the same manner. The results are shown in Table 8.

TABLE 8

| | Amount of fungus body used (g) | Reaction temperature (° C.) | Residual rate (%) of 3-mercaptopropionitrile |
|---|---|---|---|
| Pth-nitrile hydratase | 1.00 | 10 | 0 |
| | 2.00 | 30 | 0 |
| Ppu-nitrile hydratase | 1.00 | 10 | 67 |
| | 2.00 | 30 | 73 |

Example 30

Reaction by Variant Nitrile Hydratase

Example 30-(1)

Construction (1) of Plasmid Expressing Nitrile Hydratase with Modified Ribosome Binding Sequence A gene fragment of about 0.7 Kbp was obtained by the PCR reaction using the plasmid pPT-DB1 described in Example 3 of Japanese Laid-open Patent Publication No. Hei 9 (1997)-275978 as the template and the primers having the sequence as set forth in SEQ ID Nos: 59 and 60 in the Sequence Listing. The above-mentioned PCR fragment was cleaved by means of restriction enzymes EcoRI and NotI, and this mixture treated with restriction enzymes was then subjected to phenol/chloroform extraction and ethanol precipitation to purify the DNA fragment. In the same manner, pPT-DB1 was cleaved by means of EcoRI and NotI, and then subjected to agarose gel electrophoresis, through which only the DNA fragment of about 3.9 Kbp was cut out of the agarose gel. The thus obtained DNA fragments of about 0.7 kbp and about 3.9 Kbp were subjected to DNA ligation using a DNA ligation kit (manufactured by Takara Shuzo Co., Ltd.) to prepare a plasmid (1) expressing the above-mentioned nitrile hydratase with the modified ribosome binding sequence. A competent cell of *Escherichia coli* HB101 (manufactured by Toyobo Co., Ltd.) was transformed with the plasmid to obtain a transformant (1). Moreover, the plasmid was prepared from the above fungus body by alkaline SDS extraction, and the base sequence of the nitrile hydratase gene was determined using a DNA sequencer. Then, it was confirmed that the transformant (1) had the modified ribosome binding sequence shown in Table 9 in pPT-DB1.

TABLE 9

| Transformant No. | Mutation site | Change in base sequence | |
|---|---|---|---|
| | | Before substitution | After substitution |
| 1 | Ribosome binding sequence | TGAGAGGAG | TAAGGAGGT |

Example 30-(2)

Construction (2) of Substituted Amino Acid Having Nitrile Hydratase Activity

In order to obtain a transformant (2) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 10, the plasmid described in Example 79 of Japanese Laid-open Patent Publication No. 2004-194588 was used as the template, and the ribosome binding sequence was modified by the method described in Example 30-(1) to prepare a plasmid (2) encoding the above-mentioned nitrile hydratase variant. A competent cell of *Escherichia coli* HB101 (manufactured by Toyobo Co., Ltd.) was transformed with the plasmid to obtain a transformant (2).

Example 30-(3)

Construction (3) of Substituted Amino Acid Having Nitrile Hydratase Activity

In order to obtain a transformant (3) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 10, introduction of site-specific mutation was performed using a "LA PCR in vitro mutagenesis Kit" manufactured by Takara Shuzo Co., Ltd. (hereinafter referred to as the mutagenesis kit). The plasmid (1) expressing nitrile hydratase with the modified ribosome binding sequence described in Example 30-(1) was used as the template to carry out the PCR reaction.

For the PCR reaction No. 1, a reaction system of 50 μL in total containing 50 pmoles of the primer having the sequence as set forth in SEQ ID No: 61 in the Sequence Listing and 50 pmoles of an M13 primer M4 (having the sequence as set forth in SEQ ID No: 62 in the Sequence Listing) (for the composition of the system, the instructions described in the mutagenesis kit were followed) was used, and the reaction consisted of 25 PCR cycles, in which one PCR cycle included thermal denaturation (98 degrees centigrade) for 15 seconds, annealing (55 degrees centigrade) for 30 seconds and chain extension (72 degrees centigrade) for 120 seconds.

For the PCR reaction No. 2, a reaction system of 50 μL in total containing 50 pmoles of an MUT4 primer (having the sequence as set forth in SEQ ID No: 63 in the Sequence Listing) and 50 pmoles of an M13 primer RV (having the sequence as set forth in SEQ ID No: 64 in the Sequence Listing) (for the composition of the system, the instructions described in the mutagenesis kit were followed) was used, and the reaction was carried out in the same procedure as in the PCR reaction No. 1.

After completion of the PCR reaction Nos. 1 and 2, 5 μL of the reaction mixture was subjected to agarose gel electrophoresis (agarose concentration of 1.0 weight %), and an analysis of the DNA amplification product was carried out. As a result, the presence of the amplified DNA product was confirmed. From each of these PCR reaction mixtures, the excess primers and dNTP were removed using Microcon 100 (manufactured by Takara Shuzo Co., Ltd.), and then a 10 mM tris hydrochloride/1 m MEDTA buffer solution (pH 8.0) (hereinafter referred to as the TE solution) was added to each of the mixtures to prepare 50 μL each of solutions. 47.5 μL in total of an annealing solution containing 0.5 μL of both of the TE solutions (for the composition of the system, the instructions described in the mutagenesis kit were followed) was prepared, and this solution was subjected to annealing by performing thermal denaturation of the solution at 98 degrees centigrade for 10 minutes, subsequently cooling the solution to 37 degrees centigrade at a constant cooling rate over a period of 60 minutes, and then maintaining it at 37 degrees centigrade for 15 minutes.

To the thus annealed solution, 0.5 μL of TaKaRa LA Taq was added, and the mixture was heated at 72 degrees centigrade for 3 minutes, thus completing the formation of heterologous double-stranded DNA.

To this was added 50 pmoles of an M13 primer M4 (having the sequence as set forth in SEQ ID No: 62 in the Sequence Listing) and 50 pmoles of an M13 primer RV (having the sequence as set forth in SEQ ID No: 64 in the Sequence Listing) to give a reaction system of 50 μL in total, and the reaction consisted of 25 PCR cycles, in which one PCR cycle comprised thermal denaturation (98 degrees centigrade) for 15 seconds, annealing (55 degrees centigrade) for 30 seconds and chain extension (72 degrees centigrade) for 120 seconds to carry out the PCR reaction No. 3. After completion of the PCR reaction No. 3, 5 μL of the reaction mixture was subjected to agarose gel electrophoresis (using Type VII low-melting-point agarose, manufactured by Sigma Corporation; agarose concentration of 0.8 weight %), and an analysis of the DNA amplification product was carried out. As a result, the presence of the amplified DNA product of about 2 kb was confirmed.

Subsequently, an agarose fragment composed of only the DNA fragment of about 2 Kb was cut out of the agarose gel. The thus cut agarose fragment (about 0.1 g) was finely pulverized, suspended in 1 ml of the TE solution, and then kept at 55 degrees centigrade for 1 hour, whereby the agarose fragment was completely melted. The resulting agarose melt was then subjected to phenol/chloroform extraction and ethanol precipitation to purify the DNA fragment. The thus purified DNA fragment was finally dissolved in 10 μL of the TE solution. The amplified DNA fragment of about 2 Kb thus purified was cleaved by means of restriction enzymes EcoRI and HindIII, and this mixture treated with restriction enzymes was then subjected to phenol/chloroform extraction and ethanol precipitation to purify the DNA fragment. The thus purified DNA fragment was finally dissolved in 10 μL of the TE solution.

Likewise, the plasmid (1) expressing nitrile hydratase with the modified ribosome binding sequence described in Example 30-(1) was cleaved by means of EcoRI and HindIII, and then subjected to agarose gel electrophoresis (using Type VII low-melting-point agarose, manufactured by Sigma Corporation; agarose concentration of 0.7%). Only the DNA fragment of about 2.7 Kb was cut out of the agarose gel. The thus cut agarose fragment (about 0.1 g) was finely pulverized, suspended in 1 ml of the TE solution, and then kept at 55 degrees centigrade for 1 hour, whereby the agarose fragment was completely melted. The resulting agarose melt was then subjected to phenol/chloroform extraction and ethanol precipitation to purify the DNA fragment. The thus purified DNA fragment was finally dissolved in 10 μL of the TE solution.

The thus obtained DNA fragments of about 2 Kb and of about 2.7 Kb were subjected to DNA ligation using a DNA ligation kit (manufactured by Takara Shuzo Co., Ltd.). Then, a competent cell of *Escherichia coli* HB101 (manufactured by Toyobo Co., Ltd.) was transformed. The above operation was carried out using the plasmid extracted from the transformant as the template, and using the primer having the sequence as set forth in SEQ ID No: 65 instead of the primer having the sequence as set forth in SEQ ID No: 61, whereby a plasmid (3) encoding the above-mentioned nitrile hydratase variant was prepared. A competent cell of *Escherichia coli* HB101 (manufactured by Toyobo Co., Ltd.) was transformed with the plasmid to obtain a transformant (3).

Example 30-(4)

Construction (4) of Substituted Amino Acid Having Nitrile Hydratase Activity

In order to obtain a transformant (4) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 10, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 66 and 67 in the Sequence Listing were used for repeatedly carrying out the method described in Example 30-(3) per mutation point, whereby a plasmid (4) encoding the above-mentioned nitrile hydratase variant was prepared. A competent cell of *Escherichia coli* HB101 (manufactured by Toyobo Co., Ltd.) was transformed with the plasmid to obtain a transformant (4).

TABLE 10

| Transformant No. | Mutation site | Change in amino acid sequence | | Change in base sequence | |
|---|---|---|---|---|---|
| | | Before substitution | After substitution | Before substitution | After substitution |
| 2 | α-36th | Thr | Met | ACG | ATG |
| | α-148th | Gly | Asp | GGC | GAC |
| | α-204th | Val | Arg | GTC | CGC |
| | β-41st | Phe | Ile | TTC | ATC |
| | β-51st | Phe | Val | TTC | GTC |
| | β-108th | Glu | Asp | GAG | GAT |
| 3 | α-36th | Thr | Ser | ACG | TCG |
| | β-33rd | Ala | Val | GCG | GTG |
| 4 | β-40th | Thr | Ile | ACG | ATT |
| | β-61st | Ala | Val | GCC | GTC |

Example 30-(5)

Construction (5) of Substituted Amino Acid Having Nitrile Hydratase Activity

In order to obtain a transformant (5) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 11, the plasmid (2) recovered from the transformant (2) described in the above Example 30-(2) was used as the template, and the primer having the sequence as set forth in SEQ ID No: 68 in the Sequence Listing was used for carrying out the method using the mutagenesis kit described in Example 30-(3), whereby a plasmid (5) encoding the above-mentioned nitrile hydratase variant was prepared. A competent cell of *Escherichia coli* HB101 (manufactured by Toyobo Co., Ltd.) was transformed with the plasmid to obtain a transformant (5). Moreover, the plasmid was prepared from the above-mentioned fungus body by alkaline SDS extraction, and the base sequence of the nitrile hydratase gene was determined using a DNA sequencer. Then, it was confirmed that the transformant (5) had sequences according to the purpose in which mutation of 92nd Asp in the α-subunit with Glu was newly added to the plasmid (2) of Example 30-(2).

Example 30-(6)

Construction (6) of Substituted Amino Acid Having Nitrile Hydratase Activity

In order to obtain a transformant (6) obtained by mutating nitrile hydratase composed of the α-subunit as set forth in SEQ ID No: 3 in the Sequence Listing and the β-subunit as set forth in SEQ ID No: 4 in the Sequence Listing as shown in Table 11, the plasmid (3) recovered from the transformant (3) described in the above Example 30-(3) was used as the template, and the primer having the sequence as set forth in SEQ ID No: 68 in the Sequence Listing was used for carrying out the method using the mutagenesis kit described in Example 30-(3), whereby a plasmid (6) encoding the above-mentioned nitrile hydratase variant was prepared. A competent cell of *Escherichia coli* HB101 (manufactured by Toyobo Co., Ltd.) was transformed with the plasmid to obtain a transformant (6). Moreover, the plasmid was prepared from the above-mentioned fungus body by alkaline SDS extraction, and the base sequence of the nitrile hydratase gene was determined using a DNA sequencer. Then, it was confirmed that the transformant (6) had sequences according to the purpose in which mutation of 92nd Asp in the α-subunit with Glu was newly added to the plasmid (3) of Example 30-(3).

Example 30-(7)

Construction (7) of Substituted Amino Acid Having Nitrile Hydratase Activity

In order to obtain a transformant (7) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 11, the plasmid (4) recovered from the transformant (4) described in the above Example 30-(4) was used as the template, and the primer having the sequence as set forth in SEQ ID No: 68 in the Sequence Listing was used for carrying out the method using the mutagenesis kit described in Example 30-(3), whereby a plasmid (7) encoding the above-mentioned nitrile hydratase variant was prepared. A competent cell of *Escherichia coli* HB101 (manufactured by Toyobo Co., Ltd.) was transformed with the plasmid to obtain a transformant (7). Moreover, the plasmid was prepared from the above-mentioned fungus body by alkaline SDS extraction, and the base sequence of the nitrile hydratase gene was determined using a DNA sequencer. Then, it was confirmed that the transformant (7) had sequences according to the purpose in which mutation of 92nd Asp in the α-subunit with Glu was newly added to the plasmid (4) of Example 30-(4).

TABLE 11

| Trans- formant No. | Mutation site | Change in amino acid sequence | | Change in base sequence | |
| --- | --- | --- | --- | --- | --- |
| | | Before substi- tution | After substi- tution | Before substi- tution | After substi- tution |
| 5 | α-36th | Thr | Met | ACG | ATG |
| | α-92nd | Asp | Glu | GAC | GAG |
| | α-148th | Gly | Asp | GGC | GAC |
| | α-204th | Val | Arg | GTC | CGC |
| | β-41st | Phe | Ile | TTC | ATC |
| | β-51st | Phe | Val | TTC | GTC |
| | β-108th | Glu | Asp | GAG | GAT |
| 6 | α-36th | Thr | Ser | ACG | TCG |
| | α-92nd | Asp | Glu | GAC | GAG |
| | β-33rd | Ala | Val | GCG | GTG |
| 7 | α-92nd | Asp | Glu | GAC | GAG |
| | β-40th | Thr | Ile | ACG | ATT |
| | β-61st | Ala | Val | GCC | GTC |

Example 30-(8)

Construction (8) of Substituted Amino Acid Having Nitrile Hydratase Activity

In order to obtain a transformant (8) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 12, the plasmid described in Example 68 of Japanese Laid-open Patent Publication No. 2004-194588 was used as the template, and the ribosome binding sequence was modified by the method described in Example 30-(1) to prepare a plasmid (8) encoding the above-mentioned nitrile hydratase variant. A competent cell of *Escherichia coli* HB101 (manufactured by Toyobo Co., Ltd.) was transformed with the plasmid to obtain a transformant (8).

Example 30-(9)

Construction (9) of Substituted Amino Acid Having Nitrile Hydratase Activity

In order to obtain a transformant (9) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 12, the plasmid described in Example 73 of Japanese Laid-open Patent Publication No. 2004-194588 was used as the template, and the ribosome binding sequence was modified by the method described in Example 30-(1) to prepare a plasmid (9) encoding the above-mentioned nitrile hydratase variant. A competent cell of *Escherichia coli* HB101 (manufactured by Toyobo Co., Ltd.) was transformed with the plasmid to obtain a transformant (9).

Example 30-(10)

Construction (10) of Substituted Amino Acid Having Nitrile Hydratase Activity

In order to obtain a transformant (10) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 12, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 69 and 70 in the Sequence Listing were used for repeatedly carrying out the method described in Example 30-(3) per mutation point, whereby a plasmid (10) encoding the above-mentioned nitrile hydratase variant was prepared. A competent cell of *Escherichia coli* HB101 (manufactured by Toyobo Co., Ltd.) was transformed with the plasmid to obtain a transformant (10).

TABLE 12

| Trans- formant No. | Mutation site | Change in amino acid sequence | | Change in base sequence | |
| --- | --- | --- | --- | --- | --- |
| | | Before substi- tution | After substi- tution | Before substi- tution | After substi- tution |
| 8 | β-37th | Phe | Val | TTC | GTC |
| | β-108th | Glu | Asp | GAG | GAT |
| | β-200th | Ala | Glu | GCC | GAG |
| 9 | α-6th | Leu | Thr | CTG | ACG |
| | α-19th | Ala | Val | GCG | GTG |
| | α-126th | Phe | Tyr | TTC | TAC |
| | β-46th | Met | Lys | ATG | AAG |

TABLE 12-continued

| Trans-formant No. | Mutation site | Change in amino acid sequence | | Change in base sequence | |
|---|---|---|---|---|---|
| | | Before substitution | After substitution | Before substitution | After substitution |
| | β-108th | Glu | Arg | GAG | CGG |
| | β-212th | Ser | Tyr | TCC | TAC |
| 10 | β-61st | Ala | Gly | GCC | GGC |
| | β-150th | Ala | Asn | GCG | AAT |

Example 30-(11)

Construction (11) of Substituted Amino Acid Having Nitrile Hydratase Activity

In order to obtain a transformant (11) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 13, the plasmid (8) recovered from the transformant (8) described in the above Example 30-(8) was used as the template, and the primer having the sequence as set forth in SEQ ID No: 71 in the Sequence Listing was used for carrying out the method using the mutagenesis kit described in Example 30-(3), whereby a plasmid (11) encoding the above-mentioned nitrile hydratase variant was prepared. A competent cell of *Escherichia coli* HB101 (manufactured by Toyobo Co., Ltd.) was transformed with the plasmid to obtain a transformant (11). Moreover, the plasmid was prepared from the above-mentioned fungus body by alkaline SDS extraction, and the base sequence of the nitrile hydratase gene was determined using a DNA sequencer. Then, it was confirmed that the transformant (11) had sequences according to the purpose in which mutation of 94th Met in the α-subunit with Ile was newly added to the plasmid (8) of Example 30-(8).

Example 30-(12)

Construction (12) of Substituted Amino Acid Having Nitrile Hydratase Activity

In order to obtain a transformant (12) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 13, the plasmid (9) recovered from the transformant (9) described in the above Example 30-(9) was used as the template, and the primer having the sequence as set forth in SEQ ID No: 71 in the Sequence Listing was used for carrying out the method using the mutagenesis kit described in Example 30-(3), whereby a plasmid (12) encoding the above-mentioned nitrile hydratase variant was prepared. A competent cell of *Escherichia coli* HB101 (manufactured by Toyobo Co., Ltd.) was transformed with the plasmid to obtain a transformant (12). Moreover, the plasmid was prepared from the above-mentioned fungus body by alkaline SDS extraction, and the base sequence of the nitrile hydratase gene was determined using a DNA sequencer. Then, it was confirmed that the transformant (12) had sequences according to the purpose in which mutation of 94th Met in the α-subunit with Ile was newly added to the plasmid (9) of Example 30-(9).

Example 30-(13)

Construction (13) of Substituted Amino Acid Having Nitrile Hydratase Activity

In order to obtain a transformant (13) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 13, the plasmid (10) recovered from the transformant (10) described in the above Example 30-(10) was used as the template, and the primer having the sequence as set forth in SEQ ID No: 71 in the Sequence Listing was used for carrying out the method using the mutagenesis kit described in Example 30-(3), whereby a plasmid (13) encoding the above-mentioned nitrile hydratase variant was prepared. A competent cell of *Escherichia coli* HB101 (manufactured by Toyobo Co., Ltd.) was transformed with the plasmid to obtain a transformant (13). Moreover, the plasmid was prepared from the above-mentioned fungus body by alkaline SDS extraction, and the base sequence of the nitrile hydratase gene was determined using a DNA sequencer. Then, it was confirmed that the transformant (13) had sequences according to the purpose in which mutation of 94th Met in the α-subunit with Ile was newly added to the plasmid (10) of Example 30-(10).

TABLE 13

| Trans-formant No. | Mutation site | Change in amino acid sequence | | Change in base sequence | |
|---|---|---|---|---|---|
| | | Before substitution | After substitution | Before substitution | After substitution |
| 11 | α-94th | Met | Ile | ATG | ATC |
| | β-37th | Phe | Val | TTC | GTC |
| | β-108th | Glu | Asp | GAG | GAT |
| | β-200th | Ala | Glu | GCC | GAG |
| 12 | α-6th | Leu | Thr | CTG | ACG |
| | α-19th | Ala | Val | GCG | GTG |
| | α-94th | Met | Ile | ATG | ATC |
| | α-126th | Phe | Tyr | TTC | TAC |
| | β-46th | Met | Lys | ATG | AAG |
| | β-108th | Glu | Arg | GAG | CGG |
| | β-212th | Ser | Tyr | TCC | TAC |
| 13 | α-94th | Met | Ile | ATG | ATC |
| | β-61st | Ala | Gly | GCC | GGC |
| | β-150th | Ala | Asn | GCG | AAT |

Example 30-(14)

Construction (14) of Substituted Amino Acid Having Nitrile Hydratase Activity

In order to obtain a transformant (14) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 14, the plasmid described in Example 71 of Japanese Laid-open Patent Publication No. 2004-194588 was used as the template, and the ribosome binding sequence was modified by the method described in Example 30-(1) to prepare a plasmid (14) encoding the above-mentioned nitrile hydratase variant. A competent cell of Escherichia coli HB101 (manufactured by Toyobo Co., Ltd.) was transformed with the plasmid to obtain transformant (14).

Example 30-(15)

Construction (15) of Substituted Amino Acid Having Nitrile Hydratase Activity

In order to obtain a transformant (15) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 14, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 72 and 73 in the Sequence Listing were used for repeatedly carrying out the method described in Example 30-(3) per mutation point, whereby a plasmid (15) encoding the above-mentioned nitrile hydratase variant was prepared. A competent cell of Escherichia coli HB101 (manufactured by Toyobo Co., Ltd.) was transformed with the plasmid to obtain a transformant (15).

Example 30-(16)

Construction (16) of Substituted Amino Acid Having Nitrile Hydratase Activity

In order to obtain a transformant (16) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 14, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 74 and 75 in the Sequence Listing were used for repeatedly carrying out the method described in Example 30-(3) per mutation point, whereby a plasmid (16) encoding the above-mentioned nitrile hydratase variant was prepared. A competent cell of Escherichia coli HB101 (manufactured by Toyobo Co., Ltd.) was transformed with the plasmid to obtain a transformant (16).

TABLE 14

| Trans- formant No. | Mutation site | Change in amino acid sequence | | Change in base sequence | |
|---|---|---|---|---|---|
| | | Before substi- tution | After substi- tution | Before substi- tution | After substi- tution |
| 14 | β-48th | Leu | Val | CTG | GTG |
| | β-108th | Glu | Arg | GAG | CGG |
| | β-212th | Ser | Tyr | TCC | TAC |
| 15 | β-40th | Thr | Val | ACG | GTG |
| | β-218th | Cys | Met | TGC | ATG |

TABLE 14-continued

| Trans- formant No. | Mutation site | Change in amino acid sequence | | Change in base sequence | |
|---|---|---|---|---|---|
| | | Before substi- tution | After substi- tution | Before substi- tution | After substi- tution |
| 16 | β-160th | Arg | Cys | CGG | TGT |
| | β-168th | Thr | Glu | ACG | GAG |

Example 30-(17)

Construction (17) of Substituted Amino Acid Having Nitrile Hydratase Activity

In order to obtain a transformant (17) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 15, the plasmid (14) recovered from the transformant (14) described in the above Example 30-(14) was used as the template, and the primer having the sequence as set forth in SEQ ID No: 76 in the Sequence Listing was used for carrying out the method using the mutagenesis kit described in Example 30-(3), whereby a plasmid (17) encoding the above-mentioned nitrile hydratase variant was prepared. A competent cell of Escherichia coli HB101 (manufactured by Toyobo Co., Ltd.) was transformed with the plasmid to obtain a transformant (17). Moreover, the plasmid was prepared from the above-mentioned fungus body by alkaline SDS extraction, and the base sequence of the nitrile hydratase gene was determined using a DNA sequencer. Then, it was confirmed that the transformant (17) had sequences according to the purpose in which mutation of 197th Gly in the α-subunit with Cys was newly added to the plasmid (14) of Example 30-(14).

Example 30-(18)

Construction (18) of Substituted Amino Acid Having Nitrile Hydratase Activity

In order to obtain a transformant (18) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 15, the plasmid (15) recovered from the transformant (15) described in the above Example 30-(15) was used as the template, and the primer having the sequence as set forth in SEQ ID No: 76 in the Sequence Listing was used for carrying out the method using the mutagenesis kit described in Example 30-(3), whereby a plasmid (18) encoding the above-mentioned nitrile hydratase variant was prepared. A competent cell of Escherichia coli HB101 (manufactured by Toyobo Co., Ltd.) was transformed with the plasmid to obtain a transformant (18). Moreover, the plasmid was prepared from the above-mentioned fungus body by alkaline SDS extraction, and the base sequence of the nitrile hydratase gene was determined using a DNA sequencer. Then, it was confirmed that the transformant (18) had sequences according to the purpose in which mutation of 197th Gly in the α-subunit with Cys was newly added to the plasmid (15) of Example 30-(15).

Example 30-(19)

Construction (19) of Substituted Amino Acid Having Nitrile Hydratase Activity In order to obtain a transformant (19) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 15, the plasmid (16) recovered from the transformant (16) described in the above Example 30-(16) was used as the template, and the primer having the sequence as set forth in SEQ ID No: 76 in the Sequence Listing was used for carrying out the method using the mutagenesis kit described in Example 30-(3), whereby a plasmid (19) encoding the above-mentioned nitrile hydratase variant was prepared. A competent cell of *Escherichia coli* HB101 (manufactured by Toyobo Co., Ltd.) was transformed with the plasmid to obtain a transformant (19). Moreover, the plasmid was prepared from the above-mentioned fungus body by alkaline SDS extraction, and the base sequence of the nitrile hydratase gene was determined using a DNA sequencer. Then, it was confirmed that the transformant (19) had sequences according to the purpose in which mutation of 197th Gly in the α-subunit with Cys was newly added to the plasmid (16) of Example 30-(16).

TABLE 15

| Trans-formant No. | Mutation site | Change in amino acid sequence | | Change in base sequence | |
|---|---|---|---|---|---|
| | | Before substitution | After substitution | Before substitution | After substitution |
| 17 | α-197th | Gly | Cys | GGC | TGC |
| | β-48th | Leu | Val | CTG | GTG |
| | β-108th | Glu | Arg | GAG | CGG |
| | β-212th | Ser | Tyr | TCC | TAC |
| 18 | α-197th | Gly | Cys | GGC | TGC |
| | β-40th | Thr | Val | ACG | GTG |
| | β-218th | Cys | Met | TGC | ATG |
| 19 | α-197th | Gly | Cys | GGC | TGC |
| | β-160th | Arg | Cys | CGG | TGT |
| | β-168th | Thr | Glu | ACG | GAG |

Example 30-(20)

Construction (20) of Substituted Amino Acid Having Nitrile Hydratase Activity In order to obtain a transformant (20) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 16, the plasmid described in Example 75 of Japanese Laid-open Patent Publication No. 2004-194588 was used as the template, and the ribosome binding sequence was modified by the method described in Example 30-(1) to prepare a plasmid (20) encoding the above-mentioned nitrile hydratase variant. A competent cell of *Escherichia coli* HB101 (manufactured by Toyobo Co., Ltd.) was transformed with the plasmid to obtain a transformant (20).

Example 30-(21)

Construction (21) of Substituted Amino Acid Having Nitrile Hydratase Activity In order to obtain a transformant (21) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 16, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 77 and 78 in the Sequence Listing were used for repeatedly carrying out the method described in Example 30-(3) per mutation point, whereby a plasmid (21) encoding the above-mentioned nitrile hydratase variant was prepared. A competent cell of *Escherichia coli* HB101 (manufactured by Toyobo Co., Ltd.) was transformed with the plasmid to obtain a transformant (21).

Example 30-(22)

Construction (22) of Substituted Amino Acid Having Nitrile Hydratase Activity In order to obtain a transformant (22) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 16, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 79 and 80 in the Sequence Listing were used for repeatedly carrying out the method described in Example 30-(3) per mutation point, whereby a plasmid (22) encoding the above-mentioned nitrile hydratase variant was prepared. A competent cell of *Escherichia coli* HB101 (manufactured by Toyobo Co., Ltd.) was transformed with the plasmid to obtain a transformant (22).

TABLE 16

| Trans-formant No. | Mutation site | Change in amino acid sequence | | Change in base sequence | |
|---|---|---|---|---|---|
| | | Before substitution | After substitution | Before substitution | After substitution |
| 20 | α-6th | Leu | Ala | CTG | GCG |
| | α-19th | Ala | Val | GCG | GTG |
| | α-126th | Phe | Tyr | TTC | TAC |
| | β-127th | Leu | Ser | CTG | TCG |
| | β-160th | Arg | Trp | CGG | TGG |
| | β-186th | Leu | Arg | CTG | CGG |
| 21 | α-36th | Thr | Gly | ACG | GGG |
| | α-188th | Thr | Gly | ACC | GGC |
| 22 | β-176th | Tyr | Ala | TAC | GCC |
| | α-217th | Asp | Val | GAC | GTC |

Example 30-(23)

Construction (23) of Substituted Amino Acid Having Nitrile Hydratase Activity In order to obtain a transformant (23) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 17, the plasmid (20) recovered from the transformant (20) described in the above Example 30-(20) was used as the template, and the primer having the sequence as set forth in SEQ ID No: 81 in the Sequence Listing was used for carrying out the method using the mutagenesis kit described in Example 30-(3), whereby a plasmid (23) encoding the above-mentioned nitrile hydratase variant was prepared. A competent cell of *Escherichia coli* HB101 (manufactured by Toyobo Co., Ltd.) was transformed with the plasmid to obtain a transformant (23). Moreover, the plasmid was prepared from the above-mentioned fungus body by alkaline SDS extraction, and the base sequence of the nitrile hydratase gene was determined using a DNA sequencer. Then, it was confirmed that the transformant (23) had sequences according to the purpose in which mutation of 4th Val in the β-subunit with Met was newly added to the plasmid (20) of Example 30-(20).

Example 30-(24)

Construction (24) of Substituted Amino Acid Having Nitrile Hydratase Activity In order to obtain a transformant (24) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 17, the plasmid (21) recovered from the transformant (21) described in the above Example 30-(21) was used as the template, and the primer having the sequence as set forth in SEQ ID No: 81 in the Sequence Listing was used for carrying out the method using the mutagenesis kit described in Example 30-(3), whereby a plasmid (24) encoding the above-mentioned nitrile hydratase variant was prepared. A competent cell of *Escherichia coli* HB101 (manufactured by Toyobo Co., Ltd.) was transformed with the plasmid to obtain a transformant (24). Moreover, the plasmid was prepared from the above-mentioned fungus body by alkaline SDS extraction, and the base sequence of the nitrile hydratase gene was determined using a DNA sequencer. Then, it was confirmed that the transformant (24) had sequences according to the purpose in which mutation of 4th Val in the β-subunit with Met was newly added to the plasmid (21) of Example 30-(21).

Example 30-(25)

Construction (25) of Substituted Amino Acid Having Nitrile Hydratase Activity In order to obtain a transformant (25) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 17, the plasmid (22) recovered from the transformant (22) described in the above Example 30-(22) was used as the template, and the primer having the sequence as set forth in SEQ ID No: 81 in the Sequence Listing was used for carrying out the method using the mutagenesis kit described in Example 30-(3), whereby a plasmid (25) encoding the above-mentioned nitrile hydratase variant was prepared. A competent cell of *Escherichia coli* HB101 (manufactured by Toyobo Co., Ltd.) was transformed with the plasmid to obtain a transformant (25). Moreover, the plasmid was prepared from the above-mentioned fungus body by alkaline SDS extraction, and the base sequence of the nitrile hydratase gene was determined using a DNA sequencer. Then, it was confirmed that the transformant (25) had sequences according to the purpose in which mutation of 4th Val in the β-subunit with Met was newly added to the plasmid (22) of Example 30-(22).

TABLE 17

| Transformant No. | Mutation site | Change in amino acid sequence | | Change in base sequence | |
|---|---|---|---|---|---|
| | | Before substitution | After substitution | Before substitution | After substitution |
| 23 | α-6th | Leu | Ala | CTG | GCG |
| | α-19th | Ala | Val | GCG | GTG |
| | α-126th | Phe | Tyr | TTC | TAC |
| | β-4th | Val | Met | GTG | ATG |
| | β-127th | Leu | Ser | CTG | TCG |
| | β-160th | Arg | Trp | CGG | TGG |
| | β-186th | Leu | Arg | CTG | CGG |
| 24 | α-36th | Thr | Gly | ACG | GGG |
| | α-188th | Thr | Gly | ACC | GGC |
| | β-4th | Val | Met | GTG | ATG |
| 25 | β-4th | Val | Met | GTG | ATG |
| | β-176th | Tyr | Ala | TAC | GCC |
| | β-217th | Asp | Val | GAC | GTC |

Example 30-(26)

Construction (26) of Substituted Amino Acid Having Nitrile Hydratase Activity In order to obtain a transformant (26) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 18, the plasmid described in Example 72 of Japanese Laid-open Patent Publication No. 2004-194588 was used as the template, and the ribosome binding sequence was modified by the method described in Example 30-(1) to prepare a plasmid (26) encoding the above-mentioned nitrile hydratase variant. A competent cell of *Escherichia coli* HB101 (manufactured by Toyobo Co., Ltd.) was transformed with the plasmid to obtain a transformant (26).

Example 30-(27)

Construction (27) of Substituted Amino Acid Having Nitrile Hydratase Activity In order to obtain a transformant (27) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 18, the plasmid described in Example 77 of Japanese Laid-open Patent Publication No. 2004-194588 was used as the template, and the ribosome binding sequence was modified by the method described in Example 30-(1) to prepare a plasmid (27) encoding the above-mentioned nitrile hydratase variant. A competent cell of *Escherichia coli* HB101 (manufactured by Toyobo Co., Ltd.) was transformed with the plasmid to obtain a transformant (27).

TABLE 18

| Transformant No. | Mutation site | Change in amino acid sequence | | Change in base sequence | |
|---|---|---|---|---|---|
| | | Before substitution | After substitution | Before substitution | After substitution |
| 26 | β-127th | Leu | Ser | CTG | TCG |
| | β-160th | Arg | Trp | CGG | TGG |
| | β-186th | Leu | Arg | CTG | CGG |
| 27 | α-19th | Ala | Val | GCG | GTG |
| | α-71st | Arg | His | CGT | CAT |
| | α-126th | Phe | Tyr | TTC | TAC |
| | β-37th | Phe | Leu | TTC | CTC |
| | β-108th | Glu | Asp | GAG | GAT |
| | β-200th | Ala | Glu | GCC | GAG |

Example 30-(28)

Construction (28) of Substituted Amino Acid Having Nitrile Hydratase Activity

In order to obtain a transformant (28) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 19, the plasmid (26) recovered from the transformant (26) described in the above Example 30-(26) was used as the template, and the primer having the sequence as set forth in SEQ ID No: 82 in the Sequence Listing was used for carrying out the method using the mutagenesis kit described in Example 30-(3), whereby a plasmid (28) encoding the above-mentioned nitrile hydratase variant was prepared. A competent cell of *Escherichia coli* HB101 (manufactured by Toyobo Co., Ltd.) was transformed with the plasmid to obtain a transformant (28). Moreover, the plasmid was prepared from the above-mentioned fungus body by alkaline SDS extraction, and the base sequence of the nitrile hydratase gene was determined using a DNA sequencer. Then, it was confirmed that the transformant (28) had sequences according to the purpose in which mutation of 8th Gly in the β-subunit with Ala was newly added to the plasmid (26) of Example 30-(26).

Example 30-(29)

Construction (29) of Substituted Amino Acid Having Nitrile Hydratase Activity

In order to obtain a transformant (29) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 19, the plasmid (27) recovered from the transformant (27) described in the above Example 30-(27) was used as the template, and the primer having the sequence as set forth in SEQ ID No: 82 in the Sequence Listing was used for carrying out the method using the mutagenesis kit described in Example 30-(3), whereby a plasmid (29) encoding the above-mentioned nitrile hydratase variant was prepared. A competent cell of *Escherichia coli* HB101 (manufactured by Toyobo Co., Ltd.) was transformed with the plasmid to obtain a transformant (29). Moreover, the plasmid was prepared from the above-mentioned fungus body by alkaline SDS extraction, and the base sequence of the nitrile hydratase gene was determined using a DNA sequencer. Then, it was confirmed that the transformant (29) had sequences according to the purpose in which mutation of 8th Gly in the β-subunit with Ala was newly added to the plasmid (27) of Example 30-(27).

Example 30-(30)

Construction (30) of Substituted Amino Acid Having Nitrile Hydratase Activity

In order to obtain a transformant (30) expressing the nitrile hydratase variant obtained by mutating nitrile hydratase composed of the α-subunit as set forth in SEQ ID No: 3 in the Sequence Listing and the (β-subunit as set forth in SEQ ID No: 4 in the Sequence Listing as shown in Table 19, the plasmid (16) recovered from the transformant (16) described in the above Example 30-(16) was used as the template, and the primer having the sequence as set forth in SEQ ID No: 82 in the Sequence Listing was used for carrying out the method using the mutagenesis kit described in Example 30-(3), whereby a plasmid (30) encoding the above-mentioned nitrile hydratase variant was prepared. A competent cell of *Escherichia coli* HB101 (manufactured by Toyobo Co., Ltd.) was transformed with the plasmid to obtain a transformant (30). Moreover, the plasmid was prepared from the above-mentioned fungus body by alkaline SDS extraction, and the base sequence of the nitrile hydratase gene was determined using a DNA sequencer. Then, it was confirmed that the transformant (30) had sequences according to the purpose in which mutation of 8th Gly in the β-subunit with Ala was newly added to the plasmid (16) of Example 30-(16).

TABLE 19

| Transformant No. | Mutation site | Change in amino acid sequence | | Change in base sequence | |
|---|---|---|---|---|---|
| | | Before substitution | After substitution | Before substitution | After substitution |
| 28 | β-8th | Gly | Ala | GGC | GCC |
| | β-127th | Leu | Ser | CTG | TCG |
| | β-160th | Arg | Trp | CGG | TGG |
| | β-186th | Leu | Arg | CTG | CGG |
| 29 | α-19th | Ala | Val | GCG | GTG |
| | α-71st | Arg | His | CGT | CAT |
| | α-126th | Phe | Tyr | TTC | TAC |
| | β-8th | Gly | Ala | GGC | GCC |
| | β-37th | Phe | Leu | TTC | CTC |
| | β-108th | Glu | Asp | GAG | GAT |
| | β-200th | Ala | Glu | GCC | GAG |
| 30 | β-8th | Gly | Ala | GGC | GCC |
| | β-160th | Arg | Cys | CGG | TGT |
| | β-168th | Thr | Glu | ACG | GAG |

Example 30-(31)

Construction (31) of Substituted Amino Acid Having Nitrile Hydratase Activity In order to obtain a transformant (31) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 20, the plasmid described in Example 78 of Japanese Laid-open Patent Publication No. 2004-194588 was used as the template, and the ribosome binding sequence was modified by the method described in Example 30-(1) to prepare a plasmid (31) encoding the above-mentioned nitrile hydratase variant. A competent cell of *Escherichia coli* HB101 (manufactured by Toyobo Co., Ltd.) was transformed with the plasmid to obtain a transformant (31).

Example 30-(32)

Construction (32) of Substituted Amino Acid Having Nitrile Hydratase Activity In order to obtain a transformant (32) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 20, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 83 and 84 in the Sequence Listing were used for repeatedly carrying out the method described in Example 30-(3) per mutation point, whereby a plasmid (32) encoding the above-mentioned nitrile hydratase variant was prepared. A competent cell of *Escherichia coli* HB101 (manufactured by Toyobo Co., Ltd.) was transformed with the plasmid to obtain a transformant (32).

TABLE 20

| Trans-formant No. | Mutation site | Change in amino acid sequence | | Change in base sequence | |
|---|---|---|---|---|---|
| | | Before substitution | After substitution | Before substitution | After substitution |
| 31 | α-19th | Ala | Val | GCG | GTG |
| | α-71st | Arg | His | CGT | CAT |
| | α-126th | Phe | Tyr | TTC | TAC |
| | β-37th | Phe | Val | TTC | GTC |
| | β-108th | Glu | Asp | GAG | GAT |
| | β-200th | Ala | Glu | GCC | GAG |
| 32 | β-33rd | Ala | Met | GCG | ATG |
| | β-176th | Tyr | Thr | TAC | ACC |

Example 30-(33)

Construction (33) of Substituted Amino Acid Having Nitrile Hydratase Activity In order to obtain a transformant (33) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 21, the plasmid (31) recovered from the transformant (31) described in the above Example 30-(31) was used as the template, and the primer having the sequence as set forth in SEQ ID No: 85 in the Sequence Listing was used for carrying out the method using the mutagenesis kit described in Example 30-(3), whereby a plasmid (33) encoding the above-mentioned nitrile hydratase variant was prepared. A competent cell of *Escherichia coli* HB101 (manufactured by Toyobo Co., Ltd.) was transformed with the plasmid to obtain a transformant (33). Moreover, the plasmid was prepared from the above-mentioned fungus body by alkaline SDS extraction, and the base sequence of the nitrile hydratase gene was determined using a DNA sequencer. Then, it was confirmed that the transformant (33) had sequences according to the purpose in which mutation of 79th His in the β-subunit with Asn was newly added to the plasmid (31) of Example 30-(31).

Example 30-(34)

Construction (34) of Substituted Amino Acid Having Nitrile Hydratase Activity In order to obtain a transformant (34) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 21, the plasmid (32) recovered from the transformant (32) described in the above Example 30-(32) was used as the template, and the primer having the sequence as set forth in SEQ ID No: 85 in the Sequence Listing was used for carrying out the method using the mutagenesis kit described in Example 30-(3), whereby a plasmid (34) encoding the above-mentioned nitrile hydratase variant was prepared. A competent cell of *Escherichia coli* HB101 (manufactured by Toyobo Co., Ltd.) was transformed with the plasmid to obtain a transformant (34). Moreover, the plasmid was prepared from the above-mentioned fungus body by alkaline SDS extraction, and the base sequence of the nitrile hydratase gene was determined using a DNA sequencer. Then, it was confirmed that the transformant (34) had sequences according to the purpose in which mutation of 79th His in the β-subunit with Asn was newly added to the plasmid (32) of Example 30-(32).

Example 30-(35)

Construction (35) of Substituted Amino Acid Having Nitrile Hydratase Activity In order to obtain a transformant (35) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 21, the plasmid (10) recovered from the transformant (10) described in the above Example 30-(10) was used as the template, and the primer having the sequence as set forth in SEQ ID No: 85 in the Sequence Listing was used for carrying out the method using the mutagenesis kit described in Example 30-(3), whereby a plasmid (35) encoding the above-mentioned nitrile hydratase variant was prepared. A competent cell of *Escherichia coli* HB101 (manufactured by Toyobo Co., Ltd.) was transformed with the plasmid to obtain a transformant (35). Moreover, the plasmid was prepared from the above-mentioned fungus body by alkaline SDS extraction, and the base sequence of the nitrile hydratase gene was determined using a DNA sequencer. Then, it was confirmed that the transformant (35) had sequences according to the purpose in which mutation of 79th H is in the β-subunit with Asn was newly added to the plasmid (10) of Example 30-(10).

TABLE 21

| Trans-formant No. | Mutation site | Change in amino acid sequence | | Change in base sequence | |
|---|---|---|---|---|---|
| | | Before substitution | After substitution | Before substitution | After substitution |
| 33 | α-19th | Ala | Val | GCG | GTG |
| | α-71st | Arg | His | CGT | CAT |
| | α-126th | Phe | Tyr | TTC | TAC |
| | β-37th | Phe | Val | TTC | GTC |
| | β-79th | His | Asn | CAC | AAC |
| | β-108th | Glu | Asp | GAG | GAT |
| | β-200th | Ala | Glu | GCC | GAG |
| 34 | β-33rd | Ala | Met | GCG | ATG |
| | β-79th | His | Asn | CAC | AAC |
| | β-176th | Tyr | Thr | TAC | ACC |
| 35 | β-61st | Ala | Gly | GCC | GGC |
| | β-79th | His | Asn | CAC | AAC |
| | β-150th | Ala | Asn | GCG | AAT |

Example 30-(36)

Construction (36) of Substituted Amino Acid Having Nitrile Hydratase Activity

In order to obtain a transformant (36) expressing the nitrile hydratase variant obtained by mutating nitrile hydratase composed of the α-subunit as set forth in SEQ ID No: 3 in the Sequence Listing and the β-subunit as set forth in SEQ ID No 4 in the Sequence Listing as shown in Table 22, the plasmid described in Example 58 of Japanese Laid-open Patent Publication No. 2004-194588 was used as the template, and the ribosome binding sequence was modified by the method described in Example 30-(1) to prepare a plasmid (36) encoding the above-mentioned nitrile hydratase variant. A competent cell of *Escherichia coli* HB101 (manufactured by Toyobo Co., Ltd.) was transformed with the plasmid to obtain a transformant (36).

Example 30-(37)

Construction (37) of Substituted Amino Acid Having Nitrile Hydratase Activity

In order to obtain a transformant (37) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 22, the plasmid described in Example 65 of Japanese Laid-open Patent Publication No. 2004-194588 was used as the template, and the ribosome binding sequence was modified by the method described in Example 30-(1) to prepare a plasmid (37) encoding the above-mentioned nitrile hydratase variant. A competent cell of *Escherichia coli* HB101 (manufactured by Toyobo Co., Ltd.) was transformed with the plasmid to obtain a transformant (37).

Example 30-(38)

Construction (38) of Substituted Amino Acid Having Nitrile Hydratase Activity

In order to obtain a transformant (38) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 22, the plasmid described in Example 74 of Japanese Laid-open Patent Publication No. 2004-194588 was used as the template, and the ribosome binding sequence was modified by the method described in Example 30-(1) to prepare a plasmid (38) encoding the above-mentioned nitrile hydratase variant. A competent cell of *Escherichia coli* HB101 (manufactured by Toyobo Co., Ltd.) was transformed with the plasmid to obtain a transformant (38).

TABLE 22

| Trans-formant No. | Mutation site | Change in amino acid sequence | | Change in base sequence | |
|---|---|---|---|---|---|
| | | Before substitution | After substitution | Before substitution | After substitution |
| 36 | α-36th | Thr | Met | ACG | ATG |
| | α-126th | Phe | Tyr | TTC | TAC |
| 37 | α-36th | Thr | Met | ACG | ATG |
| | α-148th | Gly | Asp | GGC | GAC |
| | α-204th | Val | Arg | GTC | CGC |
| 38 | α-6th | Leu | Thr | CTG | ACG |
| | α-19th | Ala | Val | GCG | GTG |
| | α-126th | Phe | Tyr | TTC | TAC |
| | β-48th | Leu | Val | CTG | GTG |
| | β-108th | Glu | Arg | GAG | CGG |
| | β-212th | Ser | Tyr | TCC | TAC |

Example 30-(39)

Construction (39) of Substituted Amino Acid Having Nitrile Hydratase Activity

In order to obtain a transformant (39) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 23, the plasmid (36) recovered from the transformant (36) described in the above Example 30-(36) was used as the template, and the primer having the sequence as set forth in SEQ ID No: 86 in the Sequence Listing was used for carrying out the method using the mutagenesis kit described in Example 30-(3), whereby a plasmid (39) encoding the above-mentioned nitrile hydratase variant was prepared. A competent cell of *Escherichia coli* HB101 (manufactured by Toyobo Co., Ltd.) was transformed with the plasmid to obtain a transformant (39). Moreover, the plasmid was prepared from the above-mentioned fungus body by alkaline SDS extraction, and the base sequence of the nitrile hydratase gene was determined using a DNA sequencer. Then, it was confirmed that the transformant (39) had sequences according to the purpose in which mutation of 96th Gln in the β-subunit with Arg was newly added to the plasmid (36) of Example 30-(36).

Example 30-(40)

Construction (40) of Substituted Amino Acid Having Nitrile Hydratase Activity In order to obtain a transformant (40) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 23, the plasmid (37) recovered from the transformant (37) described in the above Example 30-(37) was used as the template, and the primer having the sequence as set forth in SEQ ID No: 86 in the Sequence Listing was used for carrying out the method using the mutagenesis kit described in Example 30-(3), whereby a plasmid (40) encoding the above-mentioned nitrile hydratase variant was prepared. A competent cell of *Escherichia coli* HB101 (manufactured by Toyobo Co., Ltd.) was transformed with the plasmid to obtain a transformant (40). Moreover, the plasmid was prepared from the above-mentioned fungus body by alkaline SDS extraction, and the base sequence of the nitrile hydratase gene was determined using a DNA sequencer. Then, it was confirmed that the transformant (40) had sequences according to the purpose in which mutation of 96th Gln in the β-subunit with Arg was newly added to the plasmid (37) of Example 30-(37).

Example 30-(41)

Construction (41) of Substituted Amino Acid Having Nitrile Hydratase Activity In order to obtain a transformant (41) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 23, the plasmid (38) recovered from the transformant (38) described in the above Example 30-(38) was used as the template, and the primer having the sequence as set forth in SEQ ID No: 86 in the Sequence Listing was used for carrying out the method using the mutagenesis kit described in Example 30-(3), whereby a plasmid (41) encoding the above-mentioned nitrile hydratase variant was prepared. A competent cell of *Escherichia coli* HB101 (manufactured by Toyobo Co., Ltd.) was transformed with the plasmid to obtain a transformant (41). Moreover, the plasmid was prepared from the above-mentioned fungus body by alkaline SDS extraction, and the base sequence of the nitrile hydratase gene was determined using a DNA sequencer. Then, it was confirmed that the transformant (41) had sequences according to the purpose in which mutation of 96th Gln in the β-subunit with Arg was newly added to the plasmid (38) of Example 30-(38).

TABLE 23

| Trans-formant No. | Mutation site | Change in amino acid sequence | | Change in base sequence | |
|---|---|---|---|---|---|
| | | Before substi-tution | After substi-tution | Before substi-tution | After substi-tution |
| 39 | α-36th | Thr | Met | ACG | ATG |
| | α-126th | Phe | Tyr | TTC | TAC |
| | β-96th | Gln | Arg | CAG | CGT |

TABLE 23-continued

| Trans-formant No. | Mutation site | Change in amino acid sequence | | Change in base sequence | |
|---|---|---|---|---|---|
| | | Before substi-tution | After substi-tution | Before substi-tution | After substi-tution |
| 40 | α-36th | Thr | Met | ACG | ATG |
| | α-148th | Gly | Asp | GGC | GAC |
| | α-204th | Val | Arg | GTC | CGC |
| | β-96th | Gln | Arg | CAG | CGT |
| 41 | α-6th | Leu | Thr | CTG | ACG |
| | α-19th | Ala | Val | GCG | GTG |
| | α-126th | Phe | Tyr | TTC | TAC |
| | β-48th | Leu | Val | CTG | GTG |
| | β-96th | Gln | Arg | CAG | CGT |
| | β-108th | Glu | Arg | GAG | CGG |
| | β-212th | Ser | Tyr | TCC | TAC |

Example 30-(42)

Construction (42) of Substituted Amino Acid Having Nitrile Hydratase Activity In order to obtain a transformant (42) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 24, the plasmid described in Example 62 of Japanese Laid-open Patent Publication No. 2004-194588 was used as the template, and the ribosome binding sequence was modified by the method described in Example 30-(1) to prepare a plasmid (42) encoding the above-mentioned nitrile hydratase variant. A competent cell of *Escherichia coli* HB101 (manufactured by Toyobo Co., Ltd.) was transformed with the plasmid to obtain a transformant (42).

Example 30-(43)

Construction (43) of Substituted Amino Acid Having Nitrile Hydratase Activity In order to obtain a transformant (43) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 24, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 87 and 88 in the Sequence Listing were used for repeatedly carrying out the method described in Example 30-(3) per mutation point, whereby a plasmid (43) encoding the above-mentioned nitrile hydratase variant was prepared. A competent cell of *Escherichia coli* HB101 (manufactured by Toyobo Co., Ltd.) was transformed with the plasmid to obtain a transformant (43).

TABLE 24

| Trans- formant No. | Mutation site | Change in amino acid sequence | | Change in base sequence | |
|---|---|---|---|---|---|
| | | Before substi- tution | After substi- tution | Before substi- tution | After substi- tution |
| 42 | β-160th | Arg | Trp | CGG | TGG |
| | β-186th | Leu | Arg | CTG | CGG |
| 43 | β-61st | Ala | Trp | GCC | TGG |
| | β-217th | Asp | His | GAC | CAC |

Example 30-(44)

Construction (44) of Substituted Amino Acid Having Nitrile Hydratase Activity

In order to obtain a transformant (44) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 25, the plasmid (42) recovered from the transformant (42) described in the above Example 30-(42) was used as the template, and the primer having the sequence as set forth in SEQ ID No: 89 in the Sequence Listing was used for carrying out the method using the mutagenesis kit described in Example 30-(3), whereby a plasmid (44) encoding the above-mentioned nitrile hydratase variant was prepared. A competent cell of *Escherichia coli* HB101 (manufactured by Toyobo Co., Ltd.) was transformed with the plasmid to obtain a transformant (44). Moreover, the plasmid was prepared from the above-mentioned fungus body by alkaline SDS extraction, and the base sequence of the nitrile hydratase gene was determined using a DNA sequencer. Then, it was confirmed that the transformant (44) had sequences according to the purpose in which mutation of 107th Pro in the β-subunit with Met was newly added to the plasmid (42) of Example 30-(42).

Example 30-(45)

Construction (45) of Substituted Amino Acid Having Nitrile Hydratase Activity

In order to obtain a transformant (45) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 25, the plasmid (31) recovered from the transformant (31) described in the above Example 30-(31) was used as the template, and the primer having the sequence as set forth in SEQ ID No: 120 in the Sequence Listing was used for carrying out the method using the mutagenesis kit described in Example 30-(3), whereby a plasmid (45) encoding the above-mentioned nitrile hydratase variant was prepared. A competent cell of *Escherichia coli* HB101 (manufactured by Toyobo Co., Ltd.) was transformed with the plasmid to obtain a transformant (45). Moreover, the plasmid was prepared from the above-mentioned fungus body by alkaline SDS extraction, and the base sequence of the nitrile hydratase gene was determined using a DNA sequencer. Then, it was confirmed that the transformant (45) had sequences according to the purpose in which mutation of 107th Pro in the β-subunit with Met was newly added to the plasmid (31) of Example 30-(31).

Example 30-(46)

Construction (46) of Substituted Amino Acid Having Nitrile Hydratase Activity

In order to obtain a transformant (46) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 25, the plasmid (43) recovered from the transformant (43) described in the above Example 30-(43) was used as the template, and the primer having the sequence as set forth in SEQ ID No: 89 in the Sequence Listing was used for carrying out the method using the mutagenesis kit described in Example 30-(3), whereby a plasmid (46) encoding the above-mentioned nitrile hydratase variant was prepared. A competent cell of *Escherichia coli* HB101 (manufactured by Toyobo Co., Ltd.) was transformed with the plasmid to obtain a transformant (46). Moreover, the plasmid was prepared from the above-mentioned fungus body by alkaline SDS extraction, and the base sequence of the nitrile hydratase gene was determined using a DNA sequencer. Then, it was confirmed that the transformant (46) had sequences according to the purpose in which mutation of 107th Pro in the β-subunit with Met was newly added to the plasmid (43) of Example 30-(43).

TABLE 25

| Transfor- mant No. | Mutation site | Change in amino acid sequence | | Change in base sequence | |
|---|---|---|---|---|---|
| | | Before substi- tution | After substi- tution | Before substi- tution | After substi- tution |
| 44 | β-107th | Pro | Met | CCC | ATG |
| | β-160th | Arg | Trp | CGG | TGG |
| | β-186th | Leu | Arg | CTG | CGG |
| 45 | α-19th | Ala | Val | GCG | GTG |
| | α-71st | Arg | His | CGT | CAT |
| | α-126th | Phe | Tyr | TTC | TAC |
| | β-37th | Phe | Val | TTC | GTC |
| | β-107th | Pro | Met | CCC | ATG |
| | β-108th | Glu | Asp | GAG | GAT |
| | β-200th | Ala | Glu | GCC | GAG |
| 46 | β-61st | Ala | Trp | GCC | TGG |
| | β-107th | Pro | Met | CCC | ATG |
| | β-217th | Asp | His | GAC | CAC |

Example 30-(47)

Construction (47) of Substituted Amino Acid Having Nitrile Hydratase Activity

In order to obtain a transformant (47) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 26, the plasmid (36) recovered from the transformant (36) described in the above Example 30-(36) was used as the template, and the primer having the sequence as set forth in SEQ ID No: 90 in the Sequence Listing was used for carrying out the method using the mutagenesis kit described in Example 30-(3), whereby a plasmid (47) encoding the above-mentioned nitrile hydratase variant was prepared. A competent cell of *Escherichia coli* HB101 (manufactured by Toyobo Co., Ltd.) was transformed with the plasmid to obtain a transformant (47). Moreover, the plasmid was prepared from the above-mentioned fungus body by alkaline SDS extraction, and the base sequence of the nitrile hydratase gene was determined using a DNA sequencer. Then, it was confirmed that the transformant (47) had sequences according to the purpose in which mutation of 226th Val in the β-subunit with Ile was newly added to the plasmid (36) of Example 30-(36).

Example 30-(48)

Construction (48) of Substituted Amino Acid Having Nitrile Hydratase Activity

In order to obtain a transformant (48) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 26, the plasmid (8) recovered from the transformant (8) described in the above Example 30-(8) was used as the template, and the primer having the sequence as set forth in SEQ ID No: 90 in the Sequence Listing was used for carrying out the method using the mutagenesis kit described in Example 30-(3), whereby a plasmid (48) encoding the above-mentioned nitrile hydratase variant was prepared. A competent cell of *Escherichia coli* HB101 (manufactured by Toyobo Co., Ltd.) was transformed with the plasmid to obtain a transformant (48). Moreover, the plasmid was prepared from the above-mentioned fungus body by alkaline SDS extraction, and the base sequence of the nitrile hydratase gene was determined using a DNA sequencer. Then, it was confirmed that the transformant (48) had sequences according to the purpose in which mutation of 226th Val in the β-subunit with Ile was newly added to the plasmid (8) of Example 30-(8).

Example 30-(49)

Construction (49) of Substituted Amino Acid Having Nitrile Hydratase Activity

In order to obtain a transformant (49) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 26, the plasmid (15) recovered from the transformant (15) described in the above Example 30-(15) was used as the template, and the primer having the sequence as set forth in SEQ ID No: 90 in the Sequence Listing was used for carrying out the method using the mutagenesis kit described in Example 30-(3), whereby a plasmid (49) encoding the above-mentioned nitrile hydratase variant was prepared. A competent cell of *Escherichia coli* HB101 (manufactured by Toyobo Co., Ltd.) was transformed with the plasmid to obtain a transformant (49). Moreover, the plasmid was prepared from the above-mentioned fungus body by alkaline SDS extraction, and the base sequence of the nitrile hydratase gene was determined using a DNA sequencer. Then, it was confirmed that the transformant (49) had sequences according to the purpose in which mutation of 226th Val in the β-subunit with Ile was newly added to the plasmid (15) of Example 30-(15).

TABLE 26

| Transformant No. | Mutation site | Change in amino acid sequence | | Change in base sequence | |
|---|---|---|---|---|---|
| | | Before substitution | After substitution | Before substitution | After substitution |
| 47 | α-36th | Thr | Met | ACG | ATG |
| | α-126th | Phe | Tyr | TTC | TAC |
| | β-226th | Val | Ile | GTC | ATC |
| 48 | β-37th | Phe | Val | TTC | GTC |
| | β-108th | Glu | Asp | GAG | GAT |
| | β-200th | Ala | Glu | GCC | GAG |
| | β-226th | Val | Ile | GTC | ATC |
| 49 | β-40th | Thr | Val | ACG | GTG |
| | β-218th | Cys | Met | TGC | ATG |
| | β-226th | Val | Ile | GTC | ATC |

Example 30-(50)

Construction (50) of Substituted Amino Acid Having Nitrile Hydratase Activity

In order to obtain a transformant (50) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 27, the plasmid described in Example 63 of Japanese Laid-open Patent Publication No. 2004-194588 was used as the template, and the ribosome binding sequence was modified by the method described in Example 30-(1) to prepare a plasmid (50) encoding the above-mentioned nitrile hydratase variant. A competent cell of *Escherichia coli* HB101 (manufactured by Toyobo Co., Ltd.) was transformed with the plasmid to obtain a transformant (50).

Example 30-(51)

Construction (51) of Substituted Amino Acid Having Nitrile Hydratase Activity

In order to obtain a transformant (51) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 27, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 91 and 92 in the Sequence Listing were used for repeatedly carrying out the method described in Example 30-(3) per mutation point, whereby a plasmid (51) encoding the above-mentioned nitrile hydratase variant was prepared. A competent cell of *Escherichia coli* HB101 (manufactured by Toyobo Co., Ltd.) was transformed with the plasmid to obtain a transformant (51).

Example 30-(52)

Construction (52) of Substituted Amino Acid Having Nitrile Hydratase Activity

In order to obtain a transformant (52) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 27, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 93 and 94 in the Sequence Listing were used for repeatedly carrying out the method described in Example 30-(3) per mutation point, whereby a plasmid (52) encoding the above-mentioned nitrile hydratase variant was prepared. A competent cell of *Escherichia coli* HB101 (manufactured by Toyobo Co., Ltd.) was transformed with the plasmid to obtain a transformant (52).

TABLE 27

| Transformant No. | Mutation site | Change in amino acid sequence | | Change in base sequence | |
|---|---|---|---|---|---|
| | | Before substitution | After substitution | Before substitution | After substitution |
| 50 | α-6th | Leu | Thr | CTG | ACG |
| | α-36th | Thr | Met | ACG | ATG |
| | α-126th | Phe | Tyr | TTC | TAC |
| 51 | β-61st | Ala | Ser | GCC | TCG |
| | β-160th | Arg | Met | CGG | ATG |
| 52 | β-112th | Lys | Val | AAG | GTG |
| | β-217th | Asp | Met | GAC | ATG |

Example 30-(53)

Construction (53) of Substituted Amino Acid Having Nitrile Hydratase Activity

In order to obtain a transformant (53) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 28, the plasmid (50) recovered from the transformant (50) described in the above Example 30-(50) was used as the template, and the primers having the sequence as set forth in SEQ ID Nos: 95 and 71 in the Sequence Listing were used for repeatedly carrying out the method described in Example 30-(3) per mutation point, whereby a plasmid (53) encoding the above-mentioned nitrile hydratase variant was prepared. A competent cell of *Escherichia coli* HB101 (manufactured by Toyobo Co., Ltd.) was transformed with the plasmid to obtain a transformant (53). Moreover, the plasmid was prepared from the above-mentioned fungus body by alkaline SDS extraction, and the base sequence of the nitrile hydratase gene was determined using a DNA sequencer. Then, it was confirmed that the transformant (53) had sequences according to the purpose in which mutation of 13th Ile in the α-subunit with Leu and mutation of 94th Met in the α-subunit with Ile were newly added to the plasmid (50) of Example 30-(50).

Example 30-(54)

Construction (54) of Substituted Amino Acid Having Nitrile Hydratase Activity

In order to obtain a transformant (54) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 28, the plasmid (51) recovered from the transformant (51) described in the above Example 30-(51) was used as the template, and the primers having the sequence as set forth in SEQ ID Nos: 95 and 71 in the Sequence Listing were used for repeatedly carrying out the method described in Example 30-(3) per mutation point, whereby a plasmid (54) encoding the above-mentioned nitrile hydratase variant was prepared. A competent cell of *Escherichia coli* HB101 (manufactured by Toyobo Co., Ltd.) was transformed with the plasmid to obtain a transformant (54). Moreover, the plasmid was prepared from the above-mentioned fungus body by alkaline SDS extraction, and the base sequence of the nitrile hydratase gene was determined using a DNA sequencer. Then, it was confirmed that the transformant (54) had sequences according to the purpose in which mutation of 13th Ile in the α-subunit with Leu and mutation of 94th Met in the α-subunit with Ile were newly added to the plasmid (51) of Example 30-(51).

Example 30-(55)

Construction (55) of Substituted Amino Acid Having Nitrile Hydratase Activity

In order to obtain a transformant (55) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 28, the plasmid (52) recovered from the transformant (52) described in the above Example 30-(50) was used as the template, and the primers having the sequence as set forth in SEQ ID Nos: 95 and 71 in the Sequence Listing were used for repeatedly carrying out the method described in Example 30-(3) per mutation point, whereby a plasmid (55) encoding the above-mentioned nitrile hydratase variant was prepared. A competent cell of *Escherichia coli* HB101 (manufactured by Toyobo Co., Ltd.) was transformed with the plasmid to obtain a transformant (55). Moreover, the plasmid was prepared from the above-mentioned fungus body by alkaline SDS extraction, and the base sequence of the nitrile hydratase gene was determined using a DNA sequencer. Then, it was confirmed that the transformant (55) had sequences according to the purpose in which mutation of 13th Ile in the α-subunit with Leu and mutation of 94th Met in the α-subunit with Ile were newly added to the plasmid (52) of Example 30-(52).

TABLE 28

| Transformant No. | Mutation site | Change in amino acid sequence | | Change in base sequence | |
|---|---|---|---|---|---|
| | | Before substitution | After substitution | Before substitution | After substitution |
| 53 | α-6th | Leu | Thr | CTG | ACG |
| | α-13th | Ile | Leu | ATC | CTC |
| | α-36th | Thr | Met | ACG | ATG |
| | α-94th | Met | Ile | ATG | ATC |
| | α-126th | Phe | Tyr | TTC | TAC |
| 54 | α-13th | Ile | Leu | ATC | CTC |
| | α-94th | Met | Ile | ATG | ATC |
| | β-61st | Ala | Ser | GCC | TCG |
| | β-160th | Arg | Met | CGG | ATG |

TABLE 28-continued

| Transformant No. | Mutation site | Change in amino acid sequence | | Change in base sequence | |
|---|---|---|---|---|---|
| | | Before substitution | After substitution | Before substitution | After substitution |
| 55 | α-13th | Ile | Leu | ATC | CTC |
| | α-94th | Met | Ile | ATG | ATC |
| | β-112th | Lys | Val | AAG | GTG |
| | β-217th | Asp | Met | GAC | ATG |

Example 30-(56)

Construction (56) of Substituted Amino Acid Having Nitrile Hydratase Activity

In order to obtain a transformant (56) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 29, the plasmid described in Example 70 of Japanese Laid-open Patent Publication No. 2004-194588 was used as the template, and the ribosome binding sequence was modified by the method described in Example 30-(1) to prepare a plasmid (56) encoding the above-mentioned nitrile hydratase variant. A competent cell of *Escherichia coli* HB101 (manufactured by Toyobo Co., Ltd.) was transformed with the plasmid to obtain a transformant (56).

Example 30-(57)

Construction (57) of Substituted Amino Acid Having Nitrile Hydratase Activity

In order to obtain a transformant (57) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 29, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 96 and 97 in the Sequence Listing were used for repeatedly carrying out the method described in Example 30-(3) per mutation point, whereby a plasmid (57) encoding the above-mentioned nitrile hydratase variant was prepared. A competent cell of *Escherichia coli* HB101 (manufactured by Toyobo Co., Ltd.) was transformed with the plasmid to obtain a transformant (57).

TABLE 29

| Transformant No. | Mutation site | Change in amino acid sequence | | Change in base sequence | |
|---|---|---|---|---|---|
| | | Before substitution | After substitution | Before substitution | After substitution |
| 56 | β-46th | Met | Lys | ATG | AAG |
| | β-108th | Glu | Arg | GAG | CGG |
| | β-212th | Ser | Tyr | TCC | TAC |

TABLE 29-continued

| Transformant No. | Mutation site | Change in amino acid sequence | | Change in base sequence | |
|---|---|---|---|---|---|
| | | Before substitution | After substitution | Before substitution | After substitution |
| 57 | α-36th | Thr | Ala | ACG | GCG |
| | α-48th | Asn | Gln | AAC | CAA |

Example 30-(58)

Construction (58) of Substituted Amino Acid Having Nitrile Hydratase Activity

In order to obtain a transformant (58) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 30, the plasmid (56) recovered from the transformant (56) described in the above Example 30-(56) was used as the template, and the primers having the sequence as set forth in SEQ ID Nos: 86 and 95 in the Sequence Listing were used for repeatedly carrying out the method described in Example 30-(3) per mutation point, whereby a plasmid (58) encoding the above-mentioned nitrile hydratase variant was prepared. A competent cell of *Escherichia coli* HB101 (manufactured by Toyobo Co., Ltd.) was transformed with the plasmid to obtain a transformant (58). Moreover, the plasmid was prepared from the above-mentioned fungus body by alkaline SDS extraction, and the base sequence of the nitrile hydratase gene was determined using a DNA sequencer. Then, it was confirmed that the transformant (58) had sequences according to the purpose in which mutation of 13th Ile in the α-subunit with Leu and mutation of 96th Gln in the β-subunit with Arg were newly added to the plasmid (56) of Example 30-(56).

Example 30-(59)

Construction (59) of Substituted Amino Acid Having Nitrile Hydratase Activity

In order to obtain a transformant (59) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 30, the plasmid (27) recovered from the transformant (27) described in the above Example 30-(27) was used as the template, and the primers having the sequence as set forth in SEQ ID Nos: 86 and 95 in the Sequence Listing were used for repeatedly carrying out the method described in Example 30-(3) per mutation point, whereby a plasmid (59) encoding the above-mentioned nitrile hydratase variant was prepared. A competent cell of *Escherichia coli* HB101 (manufactured by Toyobo Co., Ltd.) was transformed with the plasmid to obtain a transformant (59). Moreover, the plasmid was prepared from the above-mentioned fungus body by alkaline SDS extraction, and the base sequence of the nitrile hydratase gene was determined using a DNA sequencer. Then, it was confirmed that the transformant (59) had sequences according to the purpose in which mutation of 13th Ile in the α-subunit with Leu and mutation of 96th Gln in the β-subunit with Arg were newly added to the plasmid (27) of Example 30-(27).

Example 30-(60)

Construction (60) of Substituted Amino Acid Having Nitrile Hydratase Activity

In order to obtain a transformant (60) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 30, the plasmid (57) recovered from the transformant (57) described in the above Example 30-(57) was used as the template, and the primers having the sequence as set forth in SEQ ID Nos: 86 and 95 in the Sequence Listing were used for repeatedly carrying out the method described in Example 30-(3) per mutation point, whereby a plasmid (60) encoding the above-mentioned nitrile hydratase variant was prepared. A competent cell of *Escherichia coli* HB101 (manufactured by Toyobo Co., Ltd.) was transformed with the plasmid to obtain a transformant (60). Moreover, the plasmid was prepared from the above-mentioned fungus body by alkaline SDS extraction, and the base sequence of the nitrile hydratase gene was determined using a DNA sequencer. Then, it was confirmed that the transformant (60) had sequences according to the purpose in which mutation of 13th Ile in the α-subunit with Leu and mutation of 96th Gln in the β-subunit with Arg were newly added to the plasmid (57) of Example 30-(57).

TABLE 30

| Transformant No. | Mutation site | Change in amino acid sequence | | Change in base sequence | |
|---|---|---|---|---|---|
| | | Before substitution | After substitution | Before substitution | After substitution |
| 58 | α-13th | Ile | Leu | ATC | CTC |
| | β-46th | Met | Lys | ATG | AAG |
| | β-96th | Gln | Arg | CAG | CGT |
| | β-108th | Glu | Arg | GAG | CGG |
| | β-212th | Ser | Tyr | TCC | TAC |
| 59 | α-13th | Ile | Leu | ATC | CTC |
| | α-19th | Ala | Val | GCG | GTG |
| | α-71st | Arg | His | CGT | CAT |
| | α-126th | Phe | Tyr | TTC | TAC |
| | β-37th | Phe | Leu | TTC | CTC |
| | β-96th | Gln | Arg | CAG | CGT |
| | β-108th | Glu | Asp | GAG | GAT |
| | β-200th | Ala | Glu | GCC | GAG |
| 60 | α-13th | Ile | Leu | ATC | CTC |
| | α-36th | Thr | Ala | ACG | GCG |
| | α-48th | Asn | Gln | AAC | CAA |
| | β-96th | Gln | Arg | CAG | CGT |

Example 30-(61)

Construction (61) of Substituted Amino Acid Having Nitrile Hydratase Activity

In order to obtain a transformant (61) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 31, the plasmid (50) recovered from the transformant (50) described in the above Example 30-(50) was used as the template, and the primers having the sequence as set forth in SEQ ID Nos: 71 and 98 in the Sequence Listing were used for repeatedly carrying out the method described in Example 30-(3) per mutation point, whereby a plasmid (61) encoding the above-mentioned nitrile hydratase variant was prepared. A competent cell of *Escherichia coli* HB101 (manufactured by Toyobo Co., Ltd.) was transformed with the plasmid to obtain a transformant (61). Moreover, the plasmid was prepared from the above-mentioned fungus body by alkaline SDS extraction, and the base sequence of the nitrile hydratase gene was determined using a DNA sequencer. Then, it was confirmed that the transformant (61) had sequences according to the purpose in which mutation of 27th Met in the α-subunit with Ile and mutation of 94th Met in the α-subunit with Ile were newly added to the plasmid (50) of Example 30-(50).

Example 30-(62)

Construction (62) of Substituted Amino Acid Having Nitrile Hydratase Activity

In order to obtain a transformant (62) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 31, the plasmid (26) recovered from the transformant (26) described in the above Example 30-(26) was used as the template, and the primers having the sequence as set forth in SEQ ID Nos: 71 and 98 in the Sequence Listing were used for repeatedly carrying out the method described in Example 30-(3) per mutation point, whereby a plasmid (62) encoding the above-mentioned nitrile hydratase variant was prepared. A competent cell of *Escherichia coli* HB101 (manufactured by Toyobo Co., Ltd.) was transformed with the plasmid to obtain a transformant (62). Moreover, the plasmid was prepared from the above-mentioned fungus body by alkaline SDS extraction, and the base sequence of the nitrile hydratase gene was determined using a DNA sequencer. Then, it was confirmed that the transformant (62) had sequences according to the purpose in which mutation of 27th Met in the α-subunit with Ile and mutation of 94th Met in the α-subunit with Ile were newly added to the plasmid (26) of Example 30-(26).

Example 30-(63)

Construction (63) of Substituted Amino Acid Having Nitrile Hydratase Activity

In order to obtain a transformant (63) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 31, the plasmid (21) recovered from the transformant (21) described in the above Example 30-(21) was used as the template, and the primers having the sequence as set forth in SEQ ID Nos: 71 and 98 in the Sequence Listing were used for repeatedly carrying out the method described in Example 30-(3) per mutation point, whereby a plasmid (63) encoding the above-mentioned nitrile hydratase variant was prepared. A competent cell of *Escherichia coli* HB101 (manufactured by Toyobo Co., Ltd.) was transformed with the plasmid to obtain a transformant (63). Moreover, the plasmid was prepared from the above-mentioned fungus body by alkaline SDS extraction, and the base sequence of the nitrile hydratase gene was determined using a DNA sequencer. Then, it was confirmed that the transformant (63) had sequences according to the purpose in which mutation of 27th Met in the α-subunit with Ile and mutation of 94th Met in the α-subunit with Ile were newly added to the plasmid (21) of Example 30-(21).

TABLE 31

| Transformant No. | Mutation site | Change in amino acid sequence | | Change in base sequence | |
|---|---|---|---|---|---|
| | | Before substitution | After substitution | Before substitution | After substitution |
| 61 | α-6th | Leu | Thr | CTG | ACG |
| | α-27th | Met | Ile | ATG | ATC |
| | α-36th | Thr | Met | ACG | ATG |
| | α-94th | Met | Ile | ATG | ATC |
| | α-126th | Phe | Tyr | TTC | TAC |
| 62 | α-27th | Met | Ile | ATG | ATC |
| | α-94th | Met | Ile | ATG | ATC |
| | β-127th | Leu | Ser | CTG | TCG |
| | β-160th | Arg | Trp | CGG | TGG |
| | β-186th | Leu | Arg | CTG | CGG |
| 63 | α-27th | Met | Ile | ATG | ATC |
| | α-36th | Thr | Gly | ACG | GGG |
| | α-94th | Met | Ile | ATG | ATC |
| | α-188th | Thr | Gly | ACC | GGC |

Example 30-(64)

Construction (64) of Substituted Amino Acid Having Nitrile Hydratase Activity

In order to obtain a transformant (64) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 32, the plasmid described in Example 67 of Japanese Laid-open Patent Publication No. 2004-194588 was used as the template, and the ribosome binding sequence was modified by the method described in Example 30-(1) to prepare a plasmid (64) encoding the above-mentioned nitrile hydratase variant. A competent cell of *Escherichia coli* HB101 (manufactured by Toyobo Co., Ltd.) was transformed with the plasmid to obtain a transformant (64).

Example 30-(65)

Construction (65) of Substituted Amino Acid Having Nitrile Hydratase Activity

In order to obtain a transformant (65) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 32, the plasmid described in Example 76 of Japanese Laid-open Patent Publication No. 2004-194588 was used as the template, and the ribosome binding sequence was modified by the method described in Example 30-(1) to prepare a plasmid (65) encoding the above-mentioned nitrile hydratase variant. A competent cell of *Escherichia coli* HB101 (manufactured by Toyobo Co., Ltd.) was transformed with the plasmid to obtain a transformant (65).

Example 30-(66)

Construction (66) of Substituted Amino Acid Having Nitrile Hydratase Activity

In order to obtain a transformant (66) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 32, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 99 and 100 in the Sequence Listing were used for repeatedly carrying out the method described in Example 30-(2) per mutation point, whereby a plasmid (66) encoding the above-mentioned nitrile hydratase variant was prepared. A competent cell of *Escherichia coli* HB101 (manufactured by Toyobo Co., Ltd.) was transformed with the plasmid to obtain a transformant (66).

TABLE 32

| Transformant No. | Mutation site | Change in amino acid sequence | | Change in base sequence | |
|---|---|---|---|---|---|
| | | Before substitution | After substitution | Before substitution | After substitution |
| 64 | β-37th | Phe | Leu | TTC | CTC |
| | β-108th | Glu | Asp | GAG | GAT |
| | β-200th | Ala | Glu | GCC | GAG |
| 65 | α-6th | Leu | Thr | CTG | ACG |
| | α-36th | Thr | Met | ACG | ATG |
| | α-126th | Phe | Tyr | TTC | TAC |
| | β-10th | Thr | Asp | ACC | GAC |
| | β-118th | Phe | Val | TTC | GTC |
| | β-200th | Ala | Glu | GCC | GAG |
| 66 | β-176th | Tyr | Met | TAC | ATG |
| | β-217th | Asp | Gly | GAC | GGC |

Example 30-(67)

Construction (67) of Substituted Amino Acid Having Nitrile Hydratase Activity

In order to obtain a transformant (67) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 33, the plasmid (64) recovered from the transformant (64) described in the above Example 30-(64) was used as the template, and the primers having the sequence as set forth in SEQ ID Nos: 98 and 120 in the Sequence Listing were used for repeatedly carrying out the method described in Example 30-(3) per mutation point, whereby a plasmid (67) encoding the above-mentioned nitrile hydratase variant was prepared. A competent cell of *Escherichia coli* HB101 (manufactured by Toyobo Co., Ltd.) was transformed with the plasmid to obtain a transformant (67). Moreover, the plasmid was prepared from the above-mentioned fungus body by alkaline SDS extraction, and the base sequence of the nitrile hydratase gene was determined using a DNA sequencer. Then, it was confirmed that the transformant (67) had sequences according to the purpose in which mutation of 27th Met in the α-subunit with Ile and mutation of 107th Pro in the β-subunit with Met were newly added to the plasmid (64) of Example 30-(64).

Example 30-(68)

Construction (68) of Substituted Amino Acid Having Nitrile Hydratase Activity

In order to obtain a transformant (68) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 33, the plasmid (65) recovered from the transformant (65) described in the above Example 30-(65) was used as the template, and the primers having the sequence as set forth in SEQ ID Nos: 89 and 98 in the Sequence Listing were used for repeatedly carrying out the method described in Example 30-(3) per mutation point, whereby a plasmid (68) encoding the above-mentioned nitrile hydratase variant was prepared. A competent cell of *Escherichia coli* HB101 (manufactured by Toyobo Co., Ltd.) was transformed with the plasmid to obtain a transformant (68). Moreover, the plasmid was prepared from the above-mentioned fungus body by alkaline SDS extraction, and the base sequence of the nitrile hydratase gene was determined using a DNA sequencer. Then, it was confirmed that the transformant (68) had sequences according to the purpose in which mutation of 27th Met in the α-subunit with Ile and mutation of 107th Pro in the β-subunit with Met were newly added to the plasmid (65) of Example 30-(65).

Example 30-(69)

Construction (69) of Substituted Amino Acid Having Nitrile Hydratase Activity

In order to obtain a transformant (69) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 33, the plasmid (66) recovered from the transformant (66) described in the above Example 30-(66) was used as the template, and the primers having the sequence as set forth in SEQ ID Nos: 89 and 98 in the Sequence Listing were used for repeatedly carrying out the method described in Example 30-(3) per mutation point, whereby a plasmid (69) encoding the above-mentioned nitrile hydratase variant was prepared. A competent cell of *Escherichia coli* HB101 (manufactured by Toyobo Co., Ltd.) was transformed with the plasmid to obtain a transformant (69). Moreover, the plasmid was prepared from the above-mentioned fungus body by alkaline SDS extraction, and the base sequence of the nitrile hydratase gene was determined using a DNA sequencer. Then, it was confirmed that the transformant (69) had sequences according to the purpose in which mutation of 27th Met in the α-subunit with Ile and mutation of 107th Pro in the β-subunit with Met were newly added to the plasmid (66) of Example 30-(66).

TABLE 33

| Transformant No. | Mutation site | Change in amino acid sequence | | Change in base sequence | |
|---|---|---|---|---|---|
| | | Before substitution | After substitution | Before substitution | After substitution |
| 67 | α-27th | Met | Ile | ATG | ATC |
| | β-37th | Phe | Leu | TTC | CTC |
| | β-107th | Pro | Met | CCC | ATG |
| | β-108th | Glu | Asp | GAG | GAT |
| | β-200th | Ala | Glu | GCC | GAG |
| 68 | α-6th | Leu | Thr | CTG | ACG |
| | α-27th | Met | Ile | ATG | ATC |
| | α-36th | Thr | Met | ACG | ATG |
| | α-126th | Phe | Tyr | TTC | TAC |
| | β-10th | Thr | Asp | ACC | GAC |
| | β-107th | Pro | Met | CCC | ATG |
| | β-118th | Phe | Val | TTC | GTC |
| | β-200th | Ala | Glu | GCC | GAG |
| 69 | α-27th | Met | Ile | ATG | ATC |
| | β-107th | Pro | Met | CCC | ATG |
| | β-176th | Tyr | Met | TAC | ATG |
| | β-217th | Asp | Gly | GAC | GGC |

Example 30-(70)

Construction (70) of Substituted Amino Acid Having Nitrile Hydratase Activity

In order to obtain a transformant (70) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 34, the plasmid described in Example 69 of Japanese Laid-open Patent Publication No. 2004-194588 was used as the template, and the ribosome binding sequence was modified by the method described in Example 30-(1) to prepare a plasmid (70) encoding the above-mentioned nitrile hydratase variant. A competent cell of *Escherichia coli* HB101 (manufactured by Toyobo Co., Ltd.) was transformed with the plasmid to obtain a transformant (70).

Example 30-(71)

Construction (71) of Substituted Amino Acid Having Nitrile Hydratase Activity

In order to obtain a transformant (71) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 34, the plasmid described in Example 80 of Japanese Laid-open Patent Publication No. 2004-194588 was used as the template, and the ribosome binding sequence was modified by the method described in Example 30-(1) to prepare a plasmid (71) encoding the above-mentioned nitrile hydratase variant. A competent cell of *Escherichia coli* HB101 (manufactured by Toyobo Co., Ltd.) was transformed with the plasmid to obtain a transformant (71).

Example 30-(72)

Construction (72) of Substituted Amino Acid Having Nitrile Hydratase Activity

In order to obtain a transformant (72) expressing the nitrile hydratase variant obtained by mutating nitrile hydratase composed of the α-subunit as set forth in SEQ ID No: 3 in the Sequence Listing and the α-subunit as set forth in SEQ ID No: 4 in the Sequence Listing as shown in Table 34, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 101 and 102 in the Sequence Listing were used for repeatedly carrying out the method described in Example 30-(3) permutation point, whereby a plasmid (72) encoding the above-mentioned nitrile hydratase variant was prepared. A competent cell of *Escherichia coli* HB101 (manufactured by Toyobo Co., Ltd.) was transformed with the plasmid to obtain a transformant (72).

TABLE 34

| Transformant No. | Mutation site | Change in amino acid sequence | | Change in base sequence | |
|---|---|---|---|---|---|
| | | Before substitution | After substitution | Before substitution | After substitution |
| 70 | β-41st | Phe | Ile | TTC | ATC |
| | β-51st | Phe | Val | TTC | GTC |
| | β-108th | Glu | Asp | GAG | GAT |
| 71 | α-148th | Gly | Asp | GGC | GAC |
| | α-204th | Val | Arg | GTC | CGC |
| | β-108th | Glu | Asp | GAG | GAT |
| | β-200th | Ala | Glu | GCC | GAG |
| 72 | β-61st | Ala | Leu | GCC | CTC |
| | β-112th | Lys | Ile | AAG | ATT |

Example 30-(73)

Construction (73) of Substituted Amino Acid Having Nitrile Hydratase Activity

In order to obtain a transformant (73) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 35, the plasmid (70) recovered from the transformant (70) described in the above Example 30-(70) was used as the template, and the primers having the sequence as set forth in SEQ ID Nos: 68 and 90 in the Sequence Listing were used for repeatedly carrying out the method described in Example 30-(3) per mutation point, whereby a plasmid (73) encoding the above-mentioned nitrile hydratase variant was prepared. A competent cell of *Escherichia coli* HB101 (manufactured by Toyobo Co., Ltd.) was transformed with the plasmid to obtain a transformant (73). Moreover, the plasmid was prepared from the above-mentioned fungus body by alkaline SDS extraction, and the base sequence of the nitrile hydratase gene was determined using a DNA sequencer. Then, it was confirmed that the transformant (73) had sequences according to the purpose in which mutation of 92nd Asp in the α-subunit with Glu and mutation of 226th Val in the β-subunit with Ile were newly added to the plasmid (70) of Example 30-(70).

Example 30-(74)

Construction (74) of Substituted Amino Acid Having Nitrile Hydratase Activity

In order to obtain a transformant (74) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 35, the plasmid (71) recovered from the transformant (71) described in the above Example 30-(71) was used as the template, and the primers having the sequence as set forth in SEQ ID Nos: 68 and 90 in the Sequence Listing were used for repeatedly carrying out the method described in Example 30-(3) per mutation point, whereby a plasmid (74) encoding the above-mentioned nitrile hydratase variant was prepared. A competent cell of *Escherichia coli* HB101 (manufactured by Toyobo Co., Ltd.) was transformed with the plasmid to obtain a transformant (74). Moreover, the plasmid was prepared from the above-mentioned fungus body by alkaline SDS extraction, and the base sequence of the nitrile hydratase gene was determined using a DNA sequencer. Then, it was confirmed that the transformant (74) had sequences according to the purpose in which mutation of 92nd Asp in the α-subunit with Glu and mutation of 226th Val in the β-subunit with Ile were newly added to the plasmid (71) of Example 30-(71).

Example 30-(75)

Construction (75) of Substituted Amino Acid Having Nitrile Hydratase Activity

In order to obtain a transformant (75) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 35, the plasmid (72) recovered from the transformant (72) described in the above Example 30-(72) was used as the template, and the primers having the sequence as set forth in SEQ ID Nos: 68 and 90 in the Sequence Listing were used for repeatedly carrying out the method described in Example 30-(3) per mutation point, whereby a plasmid (75) encoding the above-mentioned nitrile hydratase variant was prepared. A competent cell of *Escherichia coli* HB101 (manufactured by Toyobo Co., Ltd.) was transformed with the plasmid to obtain a transformant (75). Moreover, the plasmid was prepared from the above-mentioned fungus body by alkaline SDS extraction, and the base sequence of the nitrile hydratase gene was determined using a DNA sequencer. Then, it was confirmed that the transformant (75) had sequences according to the purpose in which mutation of 92nd Asp in the α-subunit with Glu and mutation of 226th Val in the β-subunit with Ile were newly added to the plasmid (72) of Example 30-(72).

TABLE 35

| Transformant No. | Mutation site | Change in amino acid sequence | | Change in base sequence | |
|---|---|---|---|---|---|
| | | Before substitution | After substitution | Before substitution | After substitution |
| 73 | α-92nd | Asp | Glu | GAC | GAG |
| | β-41st | Phe | Ile | TTC | ATC |
| | β-51st | Phe | Val | TTC | GTC |
| | β-108th | Glu | Asp | GAG | GAT |
| | β-226th | Val | Ile | GTC | ATC |
| 74 | α-92nd | Asp | Glu | GAC | GAG |
| | α-148th | Gly | Asp | GGC | GAC |
| | α-204th | Val | Arg | GTC | CGC |
| | β-108th | Glu | Asp | GAG | GAT |
| | β-200th | Ala | Glu | GCC | GAG |
| | β-226th | Val | Ile | GTC | ATC |
| 75 | α-92nd | Asp | Glu | GAC | GAG |
| | β-61st | Ala | Leu | GCC | CTC |
| | β-112th | Lys | Ile | AAG | ATT |
| | β-226th | Val | Ile | GTC | ATC |

Example 30-(76)

Construction (76) of Substituted Amino Acid Having Nitrile Hydratase Activity

In order to obtain a transformant (76) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 36, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 103 and 104 in the Sequence Listing were used for repeatedly carrying out the method described in Example 30-(3) permutation point, whereby a plasmid (76) encoding the above-mentioned nitrile hydratase variant was prepared. A competent cell of *Escherichia coli* HB101 (manufactured by Toyobo Co., Ltd.) was transformed with the plasmid to obtain a transformant (76).

Example 30-(77)

Construction (77) of Substituted Amino Acid Having Nitrile Hydratase Activity

In order to obtain a transformant (77) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 36, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 105 and 106 in the Sequence Listing were used for repeatedly carrying out the method described in Example 30-(3) permutation point, whereby a plasmid (77) encoding the above-mentioned nitrile hydratase variant was prepared. A competent cell of *Escherichia coli* HB101 (manufactured by Toyobo Co., Ltd.) was transformed with the plasmid to obtain a transformant (77).

TABLE 36

| Transformant No. | Mutation site | Change in amino acid sequence | | Change in base sequence | |
|---|---|---|---|---|---|
| | | Before substitution | After substitution | Before substitution | After substitution |
| 76 | β-61st | Ala | Thr | GCC | ACG |
| | β-218th | Cys | Ser | TGC | TCC |
| 77 | β-146th | Arg | Gly | CGG | GGG |
| | β-217th | Asp | Ser | GAC | AGC |

Example 30-(78)

Construction (78) of Substituted Amino Acid Having Nitrile Hydratase Activity

In order to obtain a transformant (78) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 37, the plasmid (14) recovered from the transformant (14) described in the above Example 30-(14) was used as the template, and the primers having the sequence as set forth in SEQ ID. Nos: 81 and 85 in the Sequence Listing were used for repeatedly carrying out the method described in Example 30-(3) per mutation point, whereby a plasmid (78) encoding the above-mentioned nitrile hydratase variant was prepared. A competent cell of *Escherichia coli* HB101 (manufactured by Toyobo Co., Ltd.) was transformed with the plasmid to obtain a transformant (78). Moreover, the plasmid was prepared from the above-mentioned fungus body by alkaline SDS extraction, and the base sequence of the nitrile hydratase gene was determined using a DNA sequencer. Then, it was confirmed that the transformant (78) had sequences according to the purpose in which mutation of 4th Val in the β-subunit with Met and mutation of 79th His in the β-subunit with Asn were newly added to the plasmid (14) of Example 30-(14).

Example 30-(79)

Construction (79) of Substituted Amino Acid Having Nitrile Hydratase Activity

In order to obtain a transformant (79) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 37, the plasmid (76) recovered from the transformant (76) described in the above Example 30-(76) was used as the template, and the primers having the sequence as set forth in SEQ ID Nos: 81 and 85 in the Sequence Listing were used for repeatedly carrying out the method described in Example 30-(3) per mutation point, whereby a plasmid (79) encoding the above-mentioned nitrile hydratase variant was prepared. A competent cell of *Escherichia coli* HB101 (manufactured by Toyobo Co., Ltd.) was transformed with the plasmid to obtain a transformant (79). Moreover, the plasmid was prepared from the above-mentioned fungus body by alkaline SDS extraction, and the base sequence of the nitrile hydratase gene was determined using a DNA sequencer. Then, it was confirmed that the transformant (79) had sequences according to the purpose in which mutation of 4th Val in the β-subunit with Met and mutation of 79th His in the β-subunit with Asn were newly added to the plasmid (76) of Example 30-(76).

Example 30-(80)

Construction (80) of Substituted Amino Acid Having Nitrile Hydratase Activity

In order to obtain a transformant (80) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 37, the plasmid (77) recovered from the transformant (77) described in the above Example 30-(77) was used as the template, and the primers having the sequence as set forth in SEQ ID Nos: 81 and 85 in the Sequence Listing were used for repeatedly carrying out the method described in Example 30-(3) per mutation point, whereby a plasmid (80) encoding the above-mentioned nitrile hydratase variant was prepared. A competent cell of *Escherichia coli* HB101 (manufactured by Toyobo Co., Ltd.) was transformed with the plasmid to obtain a transformant (80). Moreover, the plasmid was prepared from the above-mentioned fungus body by alkaline SDS extraction, and the base sequence of the nitrile hydratase gene was determined using a DNA sequencer. Then, it was confirmed that the transformant (80) had sequences according to the purpose in which mutation of 4th Val in the β-subunit with Met and mutation of 79th His in the β-subunit with Asn were newly added to the plasmid (77) of Example 30-(77).

TABLE 37

| Transformant No. | Mutation site | Change in amino acid sequence | | Change in base sequence | |
|---|---|---|---|---|---|
| | | Before substitution | After substitution | Before substitution | After substitution |
| 78 | β-4th | Val | Met | GTG | ATG |
| | β-48th | Leu | Val | CTG | GTG |
| | β-79th | His | Asn | CAC | AAC |
| | β-108th | Glu | Arg | GAG | CGG |
| | β-212th | Ser | Tyr | TCC | TAC |
| 79 | β-4th | Val | Met | GTG | ATG |
| | β-61st | Ala | Thr | GCC | ACG |
| | β-79th | His | Asn | CAC | AAC |
| | β-218th | Cys | Ser | TGC | TCC |
| 80 | β-4th | Val | Met | GTG | ATG |
| | β-79th | His | Asn | CAC | AAC |
| | β-146th | Arg | Gly | CGG | GGG |
| | β-217th | Asp | Ser | GAC | AGC |

Example 30-(81)

Construction (81) of Substituted Amino Acid Having Nitrile Hydratase Activity

In order to obtain a transformant (81) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 38, the plasmid described in Example 64 of Japanese Laid-open Patent Publication No. 2004-194588 was used as the template, and the ribosome binding sequence was modified by the method described in Example 30-(1) to prepare a plasmid (81) encoding the above-mentioned nitrile hydratase variant. A competent cell of *Escherichia coli* HB101 (manufactured by Toyobo Co., Ltd.) was transformed with the plasmid to obtain a transformant (81).

Example 30-(82)

Construction (82) of Substituted Amino Acid Having Nitrile Hydratase Activity

In order to obtain a transformant (82) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 38, the plasmid described in Example 66 of Japanese Laid-open Patent Publication No. 2004-194588 was used as the template, and the ribosome binding sequence was modified by the method described in Example 30-(1) to prepare a plasmid (82) encoding the above-mentioned nitrile hydratase variant. A competent cell of *Escherichia coli* HB101 (manufactured by Toyobo Co., Ltd.) was transformed with the plasmid to obtain a transformant (82).

TABLE 38

| Transformant No. | Mutation site | Change in amino acid sequence | | Change in base sequence | |
|---|---|---|---|---|---|
| | | Before substitution | After substitution | Before substitution | After substitution |
| 81 | α-19th | Ala | Val | GCG | GTG |
| | α-71st | Arg | His | CGT | CAT |
| | α-126th | Phe | Tyr | TTC | TAC |
| 82 | β-10th | Thr | Asp | ACC | GAC |
| | β-118th | Phe | Val | TTC | GTC |
| | β-200th | Ala | Glu | GCC | GAG |

Example 30-(83)

Construction (83) of Substituted Amino Acid Having Nitrile Hydratase Activity

In order to obtain a transformant (83) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 39, the plasmid (81) recovered from the transformant (81) described in the above Example 30-(81) was used as the template, and the primers having the sequence as set forth in SEQ ID Nos: 85 and 112 in the Sequence Listing were used for repeatedly carrying out the method described in Example 30-(3) per mutation point, whereby a plasmid (83) encoding the above-mentioned nitrile hydratase variant was prepared. A competent cell of *Escherichia coli* HB101 (manufactured by Toyobo Co., Ltd.) was transformed with the plasmid to obtain a transformant (83). Moreover, the plasmid was prepared from the above-mentioned fungus body by alkaline SDS extraction, and the base sequence of the nitrile hydratase gene was determined using a DNA sequencer. Then, it was confirmed that the transformant (83) had sequences according to the purpose in which mutation of 79th His in the β-subunit with Asn and mutation of 230th Ala in the β-subunit with Glu were newly added to the plasmid (81) of Example 30-(81).

Example 30-(84)

Construction (84) of Substituted Amino Acid Having Nitrile Hydratase Activity

In order to obtain a transformant (84) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 39, the plasmid (82) recovered from the transformant (82) described in the above Example 30-(82) was used as the template, and the primers having the sequence as set forth in SEQ ID Nos: 85 and 112 in the Sequence Listing were used for repeatedly carrying out the method described in Example 30-(3) per mutation point, whereby a plasmid (84) encoding the above-mentioned nitrile hydratase variant was prepared. A competent cell of *Escherichia coli* HB101 (manufactured by Toyobo Co., Ltd.) was transformed with the plasmid to obtain a transformant (84). Moreover, the plasmid was prepared from the above-mentioned fungus body by alkaline SDS extraction, and the base sequence of the nitrile hydratase gene was determined using a DNA sequencer. Then, it was confirmed that the transformant (84) had sequences according to the purpose in which mutation of 79th His in the β-subunit with Asn and mutation of 230th Ala in the β-subunit with Glu were newly added to the plasmid (82) of Example 30-(82).

Example 30-(85)

Construction (85) of Substituted Amino Acid Having Nitrile Hydratase Activity

In order to obtain a transformant (85) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 39, the plasmid (38) recovered from the transformant (38) described in the above Example 30-(38) was used as the template, and the primers having the sequence as set forth in SEQ ID Nos: 85 and 112 in the Sequence Listing were used for repeatedly carrying out the method described in Example 30-(3) per mutation point, whereby a plasmid (85) encoding the above-mentioned nitrile hydratase variant was prepared. A competent cell of *Escherichia coli* HB101 (manufactured by Toyobo Co., Ltd.) was transformed with the plasmid to obtain a transformant (85). Moreover, the plasmid was prepared from the above-mentioned fungus body by alkaline SDS extraction, and the base sequence of the nitrile hydratase gene was determined using a DNA sequencer. Then, it was confirmed that the transformant (85) had sequences according to the purpose in which mutation of 79th His in the β-subunit with Asn and mutation of 230th Ala in the β-subunit with Glu were newly added to the plasmid (38) of Example 30-(38).

TABLE 39

| Transformant No. | Mutation site | Change in amino acid sequence | | Change in base sequence | |
|---|---|---|---|---|---|
| | | Before substitution | After substitution | Before substitution | After substitution |
| 83 | α-19th | Ala | Val | GCG | GTG |
| | α-71st | Arg | His | CGT | CAT |
| | α-126th | Phe | Tyr | TTC | TAC |
| | β-79th | His | Asn | CAC | AAC |
| | β-230th | Ala | Glu | GCG | GAG |
| 84 | β-10th | Thr | Asp | ACC | GAC |
| | β-79th | His | Asn | CAC | AAC |
| | β-118th | Phe | Val | TTC | GTC |
| | β-200th | Ala | Glu | GCC | GAG |
| | β-230th | Ala | Glu | GCG | GAG |
| 85 | α-6th | Leu | Thr | CTG | ACG |
| | α-19th | Ala | Val | GCG | GTG |
| | α-126th | Phe | Tyr | TTC | TAC |
| | β-48th | Leu | Val | CTG | GTG |
| | β-79th | His | Asn | CAC | AAC |
| | β-108th | Glu | Arg | GAG | CGG |
| | β-212th | Ser | Tyr | TCC | TAC |
| | β-230th | Ala | Glu | GCG | GAG |

Example 30-(86)

Construction (86) of Substituted Amino Acid Having Nitrile Hydratase Activity

In order to obtain a transformant (86) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 40, the plasmid described in Example 61 of Japanese Laid-open Patent Publication No. 2004-194588 was used as the template, and the ribosome binding sequence was modified by the method described in Example 30-(1) to prepare a plasmid (86) encoding the above-mentioned nitrile hydratase variant. A competent cell of *Escherichia coli* HB101 (manufactured by Toyobo Co., Ltd.) was transformed with the plasmid to obtain a transformant (86).

Example 30-(87)

Construction (87) of Substituted Amino Acid Having Nitrile Hydratase Activity

In order to obtain a transformant (87) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 40, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 107 and 108 in the Sequence Listing were used for repeatedly carrying out the method described in Example 30-(3) permutation point, whereby a plasmid (87) encoding the above-mentioned nitrile hydratase variant was prepared. A competent cell of *Escherichia coli* HB101

(manufactured by Toyobo Co., Ltd.) was transformed with the plasmid to obtain a transformant (87).

TABLE 40

| Trans- formant No. | Mutation site | Change in amino acid sequence | | Change in base sequence | |
|---|---|---|---|---|---|
| | | Before substi- tution | After substi- tution | Before substi- tution | After substi- tution |
| 86 | β-118th | Phe | Val | TTC | GTC |
| | β-200th | Ala | Glu | GCC | GAG |
| 87 | β-40th | Thr | Leu | ACG | CTG |
| | β-127th | Asp | Leu | GAC | CTC |

Example 30-(88)

Construction (88) of Substituted Amino Acid Having Nitrile Hydratase Activity

In order to obtain a transformant (88) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 41, the plasmid (86) recovered from the transformant (86) described in the above Example 30-(86) was used as the template, and the primers having the sequence as set forth in SEQ ID Nos: 109 and 110 in the Sequence Listing were used for repeatedly carrying out the method described in Example 30-(3) per mutation point, whereby a plasmid (88) encoding the above-mentioned nitrile hydratase variant was prepared. A competent cell of *Escherichia coli* HB101 (manufactured by Toyobo Co., Ltd.) was transformed with the plasmid to obtain a transformant (88). Moreover, the plasmid was prepared from the above-mentioned fungus body by alkaline SDS extraction, and the base sequence of the nitrile hydratase gene was determined using a DNA sequencer. Then, it was confirmed that the transformant (88) had sequences according to the purpose in which mutation of 110th Glu in the β-subunit with Asn and mutation of 231st Ala in the β-subunit with Val were newly added to the plasmid (86) of Example 30-(86).

Example 30-(89)

Construction (89) of Substituted Amino Acid Having Nitrile Hydratase Activity

In order to obtain a transformant (89) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 41, the plasmid (64) recovered from the transformant (64) described in the above Example 30-(64) was used as the template, and the primers having the sequence as set forth in SEQ ID Nos: 109 and 110 in the Sequence Listing were used for repeatedly carrying out the method described in Example 30-(3) per mutation point, whereby a plasmid (89) encoding the above-mentioned nitrile hydratase variant was prepared. A competent cell of *Escherichia coli* HB101 (manufactured by Toyobo Co., Ltd.) was transformed with the plasmid to obtain a transformant (89). Moreover, the plasmid was prepared from the above-mentioned fungus body by alkaline SDS extraction, and the base sequence of the nitrile hydratase gene was determined using a DNA sequencer. Then, it was confirmed that the transformant (89) had sequences according to the purpose in which mutation of 110th Glu in the β-subunit with Asn and mutation of 231st Ala in the β-subunit with Val were newly added to the plasmid (64) of Example 30-(64).

Example 30-(90)

Construction (90) of Substituted Amino Acid Having Nitrile Hydratase Activity

In order to obtain a transformant (90) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 41, the plasmid (87) recovered from the transformant (87) described in the above Example 30-(87) was used as the template, and the primers having the sequence as set forth in SEQ ID Nos: 109 and 110 in the Sequence Listing were used for repeatedly carrying out the method described in Example 30-(3) per mutation point, whereby a plasmid (90) encoding the above-mentioned nitrile hydratase variant was prepared. A competent cell of *Escherichia coli* HB101 (manufactured by Toyobo Co., Ltd.) was transformed with the plasmid to obtain a transformant (90). Moreover, the plasmid was prepared from the above-mentioned fungus body by alkaline SDS extraction, and the base sequence of the nitrile hydratase gene was determined using a DNA sequencer. Then, it was confirmed that the transformant (90) had sequences according to the purpose in which mutation of 110th Glu in the β-subunit with Asn and mutation of 231st Ala in the β-subunit with Val were newly added to the plasmid (87) of Example 30-(87).

TABLE 41

| Trans- formant No. | Mutation site | Change in amino acid sequence | | Change in base sequence | |
|---|---|---|---|---|---|
| | | Before substi- tution | After substi- tution | Before substi- tution | After substi- tution |
| 88 | β-110th | Glu | Asn | GAG | AAC |
| | β-118th | Phe | Val | TTC | GTC |
| | β-200th | Ala | Glu | GCC | GAG |
| | β-231st | Ala | Val | GCC | GTC |
| 89 | β-37th | Phe | Leu | TTC | CTC |
| | β-108th | Glu | Asp | GAG | GAT |
| | β-110th | Glu | Asn | GAG | AAC |
| | β-200th | Ala | Glu | GCC | GAG |
| | β-231st | Ala | Val | GCC | GTC |
| 90 | β-40th | Thr | Leu | ACG | CTG |
| | β-110th | Glu | Asn | GAG | AAC |
| | β-217th | Asp | Leu | GAC | CTC |
| | β-231st | Ala | Val | GCC | GTC |

Example 30-(91)

Construction (91) of Substituted Amino Acid Having Nitrile Hydratase Activity

In order to obtain a transformant (91) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 42, the plasmid (86) recovered from the transformant (86) described in the above Example 30-(86) was used as the template, and the primers having the sequence as set forth in SEQ ID Nos: 111 and 112 in the Sequence Listing were used for repeatedly carrying out the method described in Example 30-(3) per mutation point, whereby a plasmid (91) encoding the above-mentioned nitrile hydratase variant was prepared. A competent cell of *Escherichia coli* HB101 (manufactured by Toyobo Co., Ltd.) was transformed with the plasmid to obtain a transformant (91). Moreover, the plasmid was prepared from the above-mentioned fungus body by alkaline SDS extraction, and the base sequence of the nitrile hydratase gene was determined using a DNA sequencer. Then, it was confirmed that the transformant (91) had sequences according to the purpose in which mutation of 206th Pro in the β-subunit with Leu and mutation of 230th Ala in the β-subunit with Glu were newly added to the plasmid (86) of Example 30-(86).

Example 30-(92)

Construction (92) of Substituted Amino Acid Having Nitrile Hydratase Activity

In order to obtain a transformant (92) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 42, the plasmid (65) recovered from the transformant (65) described in the above Example 30-(65) was used as the template, and the primers having the sequence as set forth in SEQ ID Nos: 111 and 112 in the Sequence Listing were used for repeatedly carrying out the method described in Example 30-(3) per mutation point, whereby a plasmid (92) encoding the above-mentioned nitrile hydratase variant was prepared. A competent cell of *Escherichia coli* HB101 (manufactured by Toyobo Co., Ltd.) was transformed with the plasmid to obtain a transformant (92). Moreover, the plasmid was prepared from the above-mentioned fungus body by alkaline SDS extraction, and the base sequence of the nitrile hydratase gene was determined using a DNA sequencer. Then, it was confirmed that the transformant (92) had sequences according to the purpose in which mutation of 206th Pro in the β-subunit with Leu and mutation of 230th Ala in the β-subunit with Glu were newly added to the plasmid (65) of Example 30-(65).

Example 30-(93)

Construction (93) of Substituted Amino Acid Having Nitrile Hydratase Activity

In order to obtain a transformant (93) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 42, the plasmid (2) recovered from the transformant (2) described in the above Example 30-(2) was used as the template, and the primers having the sequence as set forth in SEQ ID Nos: 111 and 112 in the Sequence Listing were used for repeatedly carrying out the method described in Example 30-(3) per mutation point, whereby a plasmid (93) encoding the above-mentioned nitrile hydratase variant was prepared. A competent cell of *Escherichia coli* HB101 (manufactured by Toyobo Co., Ltd.) was transformed with the plasmid to obtain a transformant (93). Moreover, the plasmid was prepared from the above-mentioned fungus body by alkaline SDS extraction, and the base sequence of the nitrile hydratase gene was determined using a DNA sequencer. Then, it was confirmed that the transformant (93) had sequences according to the purpose in which mutation of 206th Pro in the O-subunit with Leu and mutation of 230th Ala in the O-subunit with Glu were newly added to the plasmid (2) of Example 30-(2).

TABLE 42

| Trans-formant No. | Mutation site | Change in amino acid sequence | | Change in base sequence | |
|---|---|---|---|---|---|
| | | Before substitution | After substitution | Before substitution | After substitution |
| 91 | β-118th | Phe | Val | TTC | GTC |
| | β-200th | Ala | Glu | GCC | GAG |
| | β-206th | Pro | Leu | CCG | CTG |
| | β-230th | Ala | Glu | GCG | GAG |
| 92 | α-6th | Leu | Thr | CTG | ACG |
| | α-36th | Thr | Met | ACG | ATG |
| | α-126th | Phe | Tyr | TTC | TAC |
| | β-10th | Thr | Asp | ACC | GAC |
| | β-118th | Phe | Val | TTC | GTC |
| | β-200th | Ala | Glu | GCC | GAG |
| | β-206th | Pro | Leu | CCG | CTG |
| | β-230th | Ala | Glu | GCG | GAG |
| 93 | α-36th | Thr | Met | ACG | ATG |
| | α-148th | Gly | Asp | GGC | GAC |
| | α-204th | Val | Arg | GTC | CGC |
| | β-41st | Phe | Ile | TTC | ATC |
| | β-51st | Phe | Val | TTC | GTC |
| | β-108th | Glu | Asp | GAG | GAT |
| | β-206th | Pro | Leu | CCG | CTG |
| | β-230th | Ala | Glu | GCG | GAG |

Example 30-(94)

Construction (94) of Substituted Amino Acid Having Nitrile Hydratase Activity

In order to obtain a transformant (94) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 43, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 113 and 114 in the Sequence Listing were used for repeatedly carrying out the method described in Example 30-(3) permutation point, whereby a plasmid (94) encoding the above-mentioned nitrile hydratase variant was prepared. A competent cell of *Escherichia coli* HB101 (manufactured by Toyobo Co., Ltd.) was transformed with the plasmid to obtain a transformant (94).

TABLE 43

| Trans-formant No. | Mutation site | Change in amino acid sequence | | Change in base sequence | |
|---|---|---|---|---|---|
| | | Before substitution | After substitution | Before substitution | After substitution |
| 94 | β-150th | Ala | Ser | GCG | TCG |
| | β-217th | Asp | Cys | GAC | TGT |

Example 30-(95)

Construction (95) of Substituted Amino Acid Having Nitrile Hydratase Activity In order to obtain a transformant (95) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 44, the plasmid (81) recovered from the transformant (81) described in the above Example 30-(81) was used as the template, and the primers having the sequence as set forth in SEQ ID Nos: 95, 9.8 and 109 in the Sequence Listing were used for repeatedly carrying out the method described in Example 30-(3) per mutation point, whereby a plasmid (95) encoding the above-mentioned nitrile hydratase variant was prepared. A competent cell of *Escherichia coli* HB101 (manufactured by Toyobo Co., Ltd.) was transformed with the plasmid to obtain a transformant (95). Moreover, the plasmid was prepared from the above-mentioned fungus body by alkaline SDS extraction, and the base sequence of the nitrile hydratase gene was determined using a DNA sequencer. Then, it was confirmed that the transformant (95) had sequences according to the purpose in which mutation of 13th Ile in the α-subunit with Leu, mutation of 27th Met in the α-subunit with Ile and mutation of 110th Glu in the β-subunit with Asn were newly added to the plasmid (81) of Example 30-(81).

Example 30-(96)

Construction (96) of Substituted Amino Acid Having Nitrile Hydratase Activity In order to obtain a transformant (96) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 44, the plasmid (56) recovered from the transformant (56) described in the above Example 30-(56) was used as the template, and the primers having the sequence as set forth in SEQ ID Nos: 95, 98 and 109 in the Sequence Listing were used for repeatedly carrying out the method described in Example 30-(3) per mutation point, whereby a plasmid (96) encoding the above-mentioned nitrile hydratase variant was prepared. A competent cell of *Escherichia coli* HB101 (manufactured by Toyobo Co., Ltd.) was transformed with the plasmid to obtain a transformant (96). Moreover, the plasmid was prepared from the above-mentioned fungus body by alkaline SDS extraction, and the base sequence of the nitrile hydratase gene was determined using a DNA sequencer. Then, it was confirmed that the transformant (96) had sequences according to the purpose in which mutation of 13th Ile in the α-subunit with Leu, mutation of 27th Met in the α-subunit with Ile and mutation of 110th Glu in the β-subunit with Asn were newly added to the plasmid (56) of Example 30-(56).

Example 30-(97)

Construction (97) of Substituted Amino Acid Having Nitrile Hydratase Activity In order to obtain a transformant (97) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 44, the plasmid (94) recovered from the transformant (94) described in the above Example 30-(94) was used as the template, and the primers having the sequence as set forth in SEQ ID Nos: 95, 98 and 109 in the Sequence Listing were used for repeatedly carrying out the method described in Example 30-(3) per mutation point, whereby a plasmid (97) encoding the above-mentioned nitrile hydratase variant was prepared. A competent cell of *Escherichia coli* HB101 (manufactured by Toyobo Co., Ltd.) was transformed with the plasmid to obtain a transformant (97). Moreover, the plasmid was prepared from the above-mentioned fungus body by alkaline SDS extraction, and the base sequence of the nitrile hydratase gene was determined using a DNA sequencer. Then, it was confirmed that the transformant (97) had sequences according to the purpose in which mutation of 13th Ile in the α-subunit with Leu, mutation of 27th Met in the α-subunit with Ile and mutation of 110th Glu in the β-subunit with Asn were newly added to the plasmid (94) of Example 30-(94).

TABLE 44

| Trans-formant No. | Mutation site | Change in amino acid sequence | | Change in base sequence | |
|---|---|---|---|---|---|
| | | Before substi-tution | After substi-tution | Before substi-tution | After substi-tution |
| 95 | α-13th | Ile | Leu | ATC | CTC |
| | α-19th | Ala | Val | GCG | GTG |
| | α-27th | Met | Ile | ATG | ATC |
| | α-71st | Arg | His | CGT | CAT |
| | α-126th | Phe | Tyr | TTC | TAC |
| | β-110th | Glu | Asn | GAG | AAC |
| 96 | α-13th | Ile | Leu | ATC | CTC |
| | α-27th | Met | Ile | ATG | ATC |
| | α-46th | Met | Lys | ATG | AAG |
| | β-108th | Glu | Arg | GAG | CGG |
| | β-110th | Glu | Asn | GAG | AAC |
| | β-212th | Ser | Tyr | TCC | TAC |
| 97 | α-13th | Ile | Leu | ATC | CTC |
| | α-27th | Met | Ile | ATG | ATC |
| | β-110th | Glu | Asn | GAG | AAC |
| | β-150th | Ala | Ser | GCG | TCG |
| | β-217th | Asp | Cys | GAC | TGT |

Example 30-(98)

Construction (98) of Substituted Amino Acid Having Nitrile Hydratase Activity In order to obtain a transformant (98) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 45, the plasmid described in Example 59 of Japanese Laid-open Patent Publication No. 2004-194588 was used as the template, and the ribosome binding sequence was modified by the method described in Example 30-(1) to prepare a plasmid (98) encoding the above-mentioned nitrile hydratase variant. A competent cell of *Escherichia coli* HB101 (manufactured by Toyobo Co., Ltd.) was transformed with the plasmid to obtain a transformant (98).

TABLE 45

| Trans-formant No. | Mutation site | Change in amino acid sequence | | Change in base sequence | |
|---|---|---|---|---|---|
| | | Before substitution | After substitution | Before substitution | After substitution |
| 98 | α-148th | Gly | Asp | GGC | GAC |
| | α-204th | Val | Arg | GTC | CGC |

Example 30-(99)

Construction (99) of Substituted Amino Acid Having Nitrile Hydratase Activity

In order to obtain a transformant (99) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 46, the plasmid (98) recovered from the transformant (98) described in the above Example 30-(98) was used as the template, and the primers having the sequence as set forth in SEQ ID Nos: 90, 95 and 111 in the Sequence Listing were used for repeatedly carrying out the method described in Example 30-(3) per mutation point, whereby a plasmid (99) encoding the above-mentioned nitrile hydratase variant was prepared. A competent cell of Escherichia coli HB101 (manufactured by Toyobo Co., Ltd.) was transformed with the plasmid to obtain a transformant (99). Moreover, the plasmid was prepared from the above-mentioned fungus body by alkaline SDS extraction, and the base sequence of the nitrile hydratase gene was determined using a DNA sequencer. Then, it was confirmed that the transformant (99) had sequences according to the purpose in which mutation of 13th Ile in the α-subunit with Leu, mutation of 206th Pro in the β-subunit with Leu and mutation of 226th Val in the β-subunit with Ile were newly added to the plasmid (98) of Example 30-(98).

Example 30-(100)

Construction (100) of Substituted Amino Acid Having Nitrile Hydratase Activity

In order to obtain a transformant (100) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 46, the plasmid (82) recovered from the transformant (82) described in the above Example 30-(82) was used as the template, and the primers having the sequence as set forth in SEQ ID Nos: 90, 95 and 111 in the Sequence Listing were used for repeatedly carrying out the method described in Example 30-(3) per mutation point, whereby a plasmid (100) encoding the above-mentioned nitrile hydratase variant was prepared. A competent cell of Escherichia coli HB101 (manufactured by Toyobo Co., Ltd.) was transformed with the plasmid to obtain a transformant (100). Moreover, the plasmid was prepared from the above-mentioned fungus body by alkaline SDS extraction, and the base sequence of the nitrile hydratase gene was determined using a DNA sequencer. Then, it was confirmed that the transformant (100) had sequences according to the purpose in which mutation of 13th Ile in the α-subunit with Leu, mutation of 206th Pro in the β-subunit with Leu and mutation of 226th Val in the β-subunit with Ile were newly added to the plasmid (82) of Example 30-(82).

Example 30-(101)

Construction (101) of Substituted Amino Acid Having Nitrile Hydratase Activity

In order to obtain a transformant (101) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 46, the plasmid (4) recovered from the transformant (4) described in the above Example 30-(4) was used as the template, and the primers having the sequence as set forth in SEQ ID Nos: 90, 95 and 111 in the Sequence Listing were used for repeatedly carrying out the method described in Example 30-(3) per mutation point, whereby a plasmid (101) encoding the above-mentioned nitrile hydratase variant was prepared. A competent cell of Escherichia coli HB101 (manufactured by Toyobo Co., Ltd.) was transformed with the plasmid to obtain a transformant (101). Moreover, the plasmid was prepared from the above-mentioned fungus body by alkaline SDS extraction, and the base sequence of the nitrile hydratase gene was determined using a DNA sequencer. Then, it was confirmed that the transformant (101) had sequences according to the purpose in which mutation of 13th Ile in the α-subunit with Leu, mutation of 206th Pro in the β-subunit with Leu and mutation of 226th Val in the β-subunit with Ile were newly added to the plasmid (4) of Example 30-(4).

TABLE 46

| Trans-formant No. | Mutation site | Chage in amino acid equence | | Change in base sequence | |
|---|---|---|---|---|---|
| | | Before substitution | After substitution | Before substitution | After substitution |
| 99 | α-13th | Ile | Leu | ATC | CTC |
| | α-148th | Gly | Asp | GGC | GAC |
| | α-204th | Val | Arg | GTC | CGC |
| | β-206th | Pro | Leu | CCG | CTG |
| | β-226th | Val | Ile | GTC | ATC |
| 100 | α-13th | Ile | Leu | ATC | CTC |
| | β-10th | Thr | Asp | ACC | GAC |
| | β-118th | Phe | Val | TTC | GTC |
| | β-200th | Ala | Glu | GCC | GAG |
| | β-206th | Pro | Leu | CCG | CTG |
| | β-226th | Val | Ile | GTC | ATC |
| 101 | α-13th | Ile | Leu | ATC | CTC |
| | β-40th | Thr | Ile | ACG | ATT |
| | β-61st | Ala | Val | GCC | GTC |
| | β-206th | Pro | Leu | CCG | CTG |
| | β-226th | Val | Ile | GTC | ATC |

Example 30-(102)

Construction (102) of Substituted Amino Acid Having Nitrile Hydratase Activity

In order to obtain a transformant (102) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 47, the plasmid described in Example 60 of Japanese Laid-open Patent Publication No. 2004-194588 was used as the template, and the ribosome binding sequence was modified by the method described in Example 30-(1) to prepare a plasmid (102) encoding the above-mentioned nitrile hydratase variant. A competent cell of *Escherichia coli* HB101 (manufactured by Toyobo Co., Ltd.) was transformed with the plasmid to obtain a transformant (102).

TABLE 47

| Transformant No. | Mutation site | Change in amino acid sequence | | Change in base sequence | |
|---|---|---|---|---|---|
| | | Before substitution | After substitution | Before substitution | After substitution |
| 102 | β-51st | Phe | Val | TTC | GTC |
| | β-108th | Glu | Asp | GAG | GAT |

Example 30-(103)

Construction (103) of Substituted Amino Acid Having Nitrile Hydratase Activity

In order to obtain a transformant (103) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 48, the plasmid (98) recovered from the transformant (98) described in the above Example 30-(98) was used as the template, and the primers having the sequence as set forth in SEQ ID Nos: 68, 81 and 111 in the Sequence Listing were used for repeatedly carrying out the method described in Example 30-(3) per mutation point, whereby a plasmid (103) encoding the above-mentioned nitrile hydratase variant was prepared. A competent cell of *Escherichia coli* HB101 (manufactured by Toyobo Co., Ltd.) was transformed with the plasmid to obtain a transformant (103). Moreover, the plasmid was prepared from the above-mentioned fungus body by alkaline SDS extraction, and the base sequence of the nitrile hydratase gene was determined using a DNA sequencer. Then, it was confirmed that the transformant (103) had sequences according to the purpose in which mutation of 92nd Asp in the α-subunit with Glu, mutation of 4th Val in the β-subunit with Met and mutation of 206th Pro in the β-subunit with Leu were newly added to the plasmid (98) of Example 30-(98).

Example 30-(104)

Construction (104) of Substituted Amino Acid Having Nitrile Hydratase Activity

In order to obtain a transformant (104) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 48, the plasmid (37) recovered from the transformant (37) described in the above Example 30-(37) was used as the template, and the primers having the sequence as set forth in SEQ ID Nos: 68, 81 and 111 in the Sequence Listing were used for repeatedly carrying out the method described in Example 30-(3) per mutation point, whereby a plasmid (104) encoding the above-mentioned nitrile hydratase variant was prepared. A competent cell of *Escherichia coli* HB101 (manufactured by Toyobo Co., Ltd.) was transformed with the plasmid to obtain a transformant (104). Moreover, the plasmid was prepared from the above-mentioned fungus body by alkaline SDS extraction, and the base sequence of the nitrile hydratase gene was determined using a DNA sequencer. Then, it was confirmed that the transformant (104) had sequences according to the purpose in which mutation of 92nd Asp in the α-subunit with Glu, mutation of 4th Val in the β-subunit with Met and mutation of 206th Pro in the β-subunit with Leu were newly added to the plasmid (37) of Example 30-(37).

Example 30-(105)

Construction (105) of Substituted Amino Acid Having Nitrile Hydratase Activity

In order to obtain a transformant (105) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 48, the plasmid (102) recovered from the transformant (102) described in the above Example 30-(102) was used as the template, and the primers having the sequence as set forth in SEQ ID Nos: 68, 81 and 111 in the Sequence Listing were used for repeatedly carrying out the method described in Example 30-(3) per mutation point, whereby a plasmid (105) encoding the above-mentioned nitrile hydratase variant was prepared. A competent cell of *Escherichia coli* HB101 (manufactured by Toyobo Co., Ltd.) was transformed with the plasmid to obtain a transformant (105). Moreover, the plasmid was prepared from the above-mentioned fungus body by alkaline SDS extraction, and the base sequence of the nitrile hydratase gene was determined using a DNA sequencer. Then, it was confirmed that the transformant (105) had sequences according to the purpose in which mutation of 92nd Asp in the α-subunit with Glu, mutation of 4th Val in the β-subunit with Met and mutation of 206th Pro in the β-subunit with Leu were newly added to the plasmid (102) of Example 30-(102).

TABLE 48

| Transformant No. | Mutation site | Change in amino acid sequence | | Change in base sequence | |
|---|---|---|---|---|---|
| | | Before substitution | After substitution | Before substitution | After substitution |
| 103 | α-92nd | Asp | Glu | GAC | GAG |
| | α-148th | Gly | Asp | GGC | GAC |
| | α-204th | Val | Arg | GTC | CGC |
| | β-4th | Val | Met | GTG | ATG |
| | β-206th | Pro | Leu | CCG | CTG |
| 104 | α-36th | Thr | Met | ACG | ATG |
| | α-92nd | Asp | Glu | GAC | GAG |
| | α-148th | Gly | Asp | GGC | GAC |
| | α-204th | Val | Arg | GTC | CGC |
| | β-4th | Val | Met | GTG | ATG |
| | β-206th | Pro | Leu | CCG | CTG |
| 105 | α-92nd | Asp | Glu | GAC | GAG |
| | β-4th | Val | Met | GTG | ATG |
| | β-51st | Phe | Val | TTC | GTC |
| | β-108th | Glu | Asp | GAG | GAT |
| | β-206th | Pro | Leu | CCG | CTG |

Example 30-(106)

Construction (106) of Substituted Amino Acid Having Nitrile Hydratase Activity In order to obtain a transformant (106) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 49, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 115 and 116 in the Sequence Listing were used for repeatedly carrying out the method described in Example 30-(3) per mutation point, whereby a plasmid (106) encoding the above-mentioned nitrile hydratase variant was prepared. A competent cell of *Escherichia coli* HB101 (manufactured by Toyobo Co., Ltd.) was transformed with the plasmid to obtain a transformant (106).

TABLE 49

| Trans-formant No. | Mutation site | Change in amino acid sequence | | Change in base sequence | |
|---|---|---|---|---|---|
| | | Before substitution | After substitution | Before substitution | After substitution |
| 106 | β-171th | Lys | Ala | AAG | GCG |
| | β-217th | Asp | Thr | GAC | ACC |

Example 30-(107)

Construction (107) of Substituted Amino Acid Having Nitrile Hydratase Activity In order to obtain a transformant (107) expressing the nitrile hydratase variant obtained by mutating nitrile hydratase composed of the α-subunit asset forth in SEQ ID No: 3 in the Sequence Listing and the β-subunit as set forth in SEQ ID No: 4 in the Sequence Listing as shown in Table 50, the plasmid (42) recovered from the transformant (42) described in the above Example 30-(42) was used as the template, and the primers having the sequence as set forth in SEQ ID Nos: 71, 82 and 86 in the Sequence Listing were used for repeatedly carrying out the method described in Example 30-(3) per mutation point, whereby a plasmid (107) encoding the above-mentioned nitrile hydratase variant was prepared. A competent cell of *Escherichia coli* HB101 (manufactured by Toyobo Co., Ltd.) was transformed with the plasmid to obtain a transformant (107). Moreover, the plasmid was prepared from the above-mentioned fungus body by alkaline SDS extraction, and the base sequence of the nitrile hydratase gene was determined using a DNA sequencer. Then, it was confirmed that the transformant (107) had sequences according to the purpose in which mutation of 94th Met in the α-subunit with Ile, mutation of 8th Gly in the β-subunit with Ala and mutation of 96th Gln in the β-subunit with Arg were newly added to the plasmid (42) of Example 30-(42).

Example 30-(108)

Construction (108) of Substituted Amino Acid Having Nitrile Hydratase Activity In order to obtain a transformant (108) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 50, the plasmid (20) recovered from the transformant (20) described in the above Example 30-(20) was used as the template, and the primers having the sequence as set forth in SEQ ID Nos: 71, 82 and 86 in the Sequence Listing were used for repeatedly carrying out the method described in Example 30-(3) per mutation point, whereby a plasmid (108) encoding the above-mentioned nitrile hydratase variant was prepared. A competent cell of *Escherichia coli* HB101 (manufactured by Toyobo Co., Ltd.) was transformed with the plasmid to obtain a transformant (108). Moreover, the plasmid was prepared from the above-mentioned fungus body by alkaline SDS extraction, and the base sequence of the nitrile hydratase gene was determined using a DNA sequencer. Then, it was confirmed that the transformant (108) had sequences according to the purpose in which mutation of 94th Met in the α-subunit with Ile, mutation of 8th Gly in the β-subunit with Ala and mutation of 96th Gln in the β-subunit with Arg were newly added to the plasmid (20) of Example 30-(20).

Example 30-(109)

Construction (109) of Substituted Amino Acid Having Nitrile Hydratase Activity In order to obtain a transformant (109) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 50, the plasmid (106) recovered from the transformant (106) described in the above Example 30-(106) was used as the template, and the primers having the sequence as set forth in SEQ ID Nos: 71, 82 and 86 in the Sequence Listing were used for repeatedly carrying out the method described in Example 30-(3) per mutation point, whereby a plasmid (109) encoding the above-mentioned nitrile hydratase variant was prepared. A competent cell of *Escherichia coli* HB101 (manufactured by Toyobo Co., Ltd.) was transformed with the plasmid to obtain a transformant (109). Moreover, the plasmid was prepared from the above-mentioned fungus body by alkaline SDS extraction, and the base sequence, of the nitrile hydratase gene was determined using a DNA sequencer. Then, it was confirmed that the transformant (109) had sequences according to the purpose in which mutation of 94th Met in the α-subunit with Ile, mutation of 8th Gly in the β-subunit with Ala and mutation of 96th Gln in the β-subunit with Arg were newly added to the plasmid (106) of Example 30-(106).

TABLE 50

| Trans-formant No. | Mutation site | Change in amino acid sequence | | Change in base sequence | |
|---|---|---|---|---|---|
| | | Before substitution | After substitution | Before substitution | After substitution |
| 107 | α-94th | Met | Ile | ATG | ATC |
| | β-8th | Gly | Ala | GGC | GCC |
| | β-96th | Gln | Arg | CAG | CGT |
| | β-160th | Arg | Trp | CGG | TGG |
| | β-186th | Leu | Arg | CTG | CGG |
| 108 | α-6th | Leu | Ala | CTG | GCG |
| | α-19th | Ala | Val | GCG | GTG |

TABLE 50-continued

| Trans-formant No. | Mutation site | Change in amino acid sequence | | Change in base sequence | |
|---|---|---|---|---|---|
| | | Before substi-tution | After substi-tution | Before substi-tution | After substi-tution |
| | α-94th | Met | Ile | ATG | ATC |
| | α-126th | Phe | Tyr | TTC | TAC |
| | β-8th | Gly | Ala | GGC | GCC |
| | β-96th | Gln | Arg | CAG | CGT |
| | β-127th | Leu | Ser | CTG | TCG |
| | β-160th | Arg | Trp | CGG | TGG |
| | β-186th | Leu | Arg | CTG | CGG |
| 109 | α-94th | Met | Ile | ATG | ATC |
| | β-8th | Gly | Ala | GGC | GCC |
| | β-96th | Gln | Arg | CAG | CGT |
| | β-171st | Lys | Ala | AAG | GCG |
| | β-217th | Asp | Thr | GAC | ACC |

Example 30-(110)

Construction (110) of Substituted Amino Acid Having Nitrile Hydratase Activity

In order to obtain a transformant (110) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 51, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 105 and 117 in the Sequence Listing were used for repeatedly carrying out the method described in Example 30-(3) per mutation point, whereby a plasmid (110) encoding the above-mentioned nitrile hydratase variant was prepared. A competent cell of *Escherichia coli* HB101 (manufactured by Toyobo Co., Ltd.) was transformed with the plasmid to obtain a transformant (110).

TABLE 51

| Trans-formant No. | Mutation site | Change in amino acid sequence | | Change in base sequence | |
|---|---|---|---|---|---|
| | | Before substi-tution | After substi-tution | Before substi-tution | After substi-tution |
| 110 | α-48th | Asn | Glu | AAC | GAA |
| | β-146th | Arg | Gly | CGG | GGG |

Example 30-(111)

Construction (111) of Substituted Amino Acid Having Nitrile Hydratase Activity

In order to obtain a transformant (111) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 52, the plasmid (102) recovered from the transformant (102) described in the above Example 30-(102) was used as the template, and the primers having the sequence as set forth in SEQ ID Nos: 76, 89 and 112 in the Sequence Listing were used for repeatedly carrying out the method described in Example 30-(3) per mutation point, whereby a plasmid (111) encoding the above-mentioned nitrile hydratase variant was prepared. A competent cell of *Escherichia coli* HB101 (manufactured by Toyobo Co., Ltd.) was transformed with the plasmid to obtain a transformant (111). Moreover, the plasmid was prepared from the above-mentioned fungus body by alkaline SDS extraction, and the base sequence of the nitrile hydratase gene was determined using a DNA sequencer. Then, it was confirmed that the transformant (111) had sequences according to the purpose in which mutation of 197th Gly in the α-subunit with Cys, mutation of 107th Pro in the β-subunit with Met and mutation of 230th Ala in the β-subunit with Glu were newly added to the plasmid (102) of Example 30-(102).

Example 30-(112)

Construction (112) of Substituted Amino Acid Having Nitrile Hydratase Activity

In order to obtain a transformant (112) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 52, the plasmid (70) recovered from the transformant (70) described in the above Example 30-(70) was used as the template, and the primers having the sequence as set forth in SEQ ID Nos: 76, 89 and 112 in the Sequence Listing were used for repeatedly carrying out the method described in Example 30-(3) per mutation point, whereby a plasmid (112) encoding the above-mentioned nitrile hydratase variant was prepared. A competent cell of *Escherichia coli* HB101 (manufactured by Toyobo Co., Ltd.) was transformed with the plasmid to obtain a transformant (112). Moreover, the plasmid was prepared from the above-mentioned fungus body by alkaline SDS extraction, and the base sequence of the nitrile hydratase gene was determined using a DNA sequencer. Then, it was confirmed that the transformant (112) had sequences according to the purpose in which mutation of 197th Gly in the α-subunit with Cys, mutation of 107th Pro in the β-subunit with Met and mutation of 230th Ala in the β-subunit with Glu were newly added to the plasmid (70) of Example 30-(70).

Example 30-(113)

Construction (113) of Substituted Amino Acid Having Nitrile Hydratase Activity

In order to obtain a transformant (113) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 52, the plasmid (110) recovered from the transformant (110) described in the above Example 30-(110) was used as the template, and the primers having the sequence as set forth in SEQ ID Nos: 76, 89 and 112 in the Sequence Listing were used for repeatedly carrying out the method described in Example 30-(3) per mutation point, whereby a plasmid (113) encoding the above-mentioned nitrile hydratase variant was prepared. A competent cell of *Escherichia coli* HB101 (manufactured by Toyobo Co., Ltd.) was transformed with the plasmid to obtain a transformant (113). Moreover, the plasmid was prepared from the above-mentioned fungus body by alkaline SDS extraction, and the base sequence of the nitrile hydratase gene was determined using a DNA sequencer. Then, it was confirmed that the transformant (113) had sequences according to the purpose in which mutation of 197th Gly in the α-subunit with Cys, mutation of 107th Pro in the β-subunit with Met and mutation of 230th Ala in the β-subunit with Glu were newly added to the plasmid (110) of Example 30-(110).

TABLE 52

| Trans-formant No. | Mutation site | Change in amino acid sequence | | Change in base sequence | |
|---|---|---|---|---|---|
| | | Before substi-tution | After substi-tution | Before substi-tution | After substi-tution |
| 111 | α-197th | Gly | Cys | GGC | TGC |
| | β-51st | Phe | Val | TTC | GTC |
| | β-107th | Pro | Met | CCC | ATG |
| | β-108th | Glu | Asp | GAG | GAT |
| | β-230th | Ala | Glu | GCG | GAG |
| 112 | α-197th | Gly | Cys | GGC | TGC |
| | β-41st | Phe | Ile | TTC | ATC |
| | β-51st | Phe | Val | TTC | GTC |
| | β-107th | Pro | Met | CCC | ATG |
| | β-108th | Glu | Asp | GAG | GAT |
| | β-230th | Ala | Glu | GCG | GAG |
| 113 | α-48th | Asn | Glu | AAC | GAA |
| | α-197th | Gly | Cys | GGC | TGC |
| | β-107th | Pro | Met | CCC | ATG |
| | β-146th | Arg | Gly | CGG | GGG |
| | β-230th | Ala | Glu | GCG | GAG |

Example 30-(114)

Construction (114) of Substituted Amino Acid Having Nitrile Hydratase Activity

In order to obtain a transformant (114) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 53, introduction of site-specific mutation was performed using the mutagenesis kit described in the above Example 30-(3). The plasmid (1) expressing nitrile hydratase with the modified ribosome binding sequence described in Example 30-(1) was used as the template, and the primers having the sequence as set forth in SEQ ID Nos: 118 and 119 in the Sequence Listing were used for repeatedly carrying out the method described in Example 30-(3) per mutation point, whereby a plasmid (114) encoding the above-mentioned nitrile hydratase variant was prepared. A competent cell of *Escherichia coli* HB101 (manufactured by Toyobo Co., Ltd.) was transformed with the plasmid to obtain a transformant (114).

TABLE 53

| Trans-formant No. | Mutation site | Change in amino acid sequence | | Change in base sequence | |
|---|---|---|---|---|---|
| | | Before substi-tution | After substi-tution | Before substi-tution | After substi-tution |
| 114 | α-36th | Thr | Trp | ACG | TGG |
| | β-176th | Tyr | Cys | TAC | TGC |

Example 30-(115)

Construction (115) of Substituted Amino Acid Having Nitrile Hydratase Activity

In order to obtain a transformant (115) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 54, the plasmid (38) recovered from the transformant (38) described in the above Example 30-(38) was used as the template, and the primers having the sequence as set forth in SEQ ID Nos: 85 and 121 in the Sequence Listing were used for repeatedly carrying out the method described in Example 30-(3) per mutation point, whereby a plasmid (115) encoding the above-mentioned nitrile hydratase variant was prepared. A competent cell of *Escherichia coli* HB101 (manufactured by Toyobo Co., Ltd.) was transformed with the plasmid to obtain a transformant (115). Moreover, the plasmid was prepared from the above-mentioned fungus body by alkaline SDS extraction, and the base sequence of the nitrile hydratase gene was determined using a DNA sequencer. Then, it was confirmed that the transformant (115) had sequences according to the purpose in which mutation of 79th His in the β-subunit with Asn, mutation of 230th Ala in the β-subunit with Glu and mutation of 231st Ala in the β-subunit with Val were newly added to the plasmid (38) of Example 30-(38).

Example 30-(116)

Construction (116) of Substituted Amino Acid Having Nitrile Hydratase Activity

In order to obtain a transformant (116) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 54, the plasmid (9) recovered from the transformant (9) described in the above Example 30-(9) was used as the template, and the primers having the sequence as set forth in SEQ ID Nos: 85 and 121 in the Sequence Listing were used for repeatedly carrying out the method described in Example 30-(3) per mutation point, whereby a plasmid (116) encoding the above-mentioned nitrile hydratase variant was prepared. A competent cell of *Escherichia coli* HB101 (manufactured by Toyobo Co., Ltd.) was transformed with the plasmid to obtain a transformant (116). Moreover, the plasmid was prepared from the above-mentioned fungus body by alkaline SDS extraction, and the base sequence of the nitrile hydratase gene was determined using a DNA sequencer. Then, it was confirmed that the transformant (116) had sequences according to the purpose in which mutation of 79th His in the β-subunit with Asn, mutation of 230th Ala in the β-subunit with Glu and mutation of 231st Ala in the β-subunit with Val were newly added to the plasmid (9) of Example 30-(9).

Example 30-(117)

Construction (117) of Substituted Amino Acid Having Nitrile Hydratase Activity

In order to obtain a transformant (117) expressing the nitrile hydratase variant obtained by mutating nitrile hydratase composed of the α-subunit as set forth in SEQ ID No: 3 in the Sequence Listing and the β-subunit as set forth in SEQ ID No: 4 in the Sequence Listing as shown in Table 54, the plasmid (114) recovered from the transformant (114) described in the above Example 30-(114) was used as the template, and the primers having the sequence as set forth in SEQ ID Nos: 85 and 121 in the Sequence Listing were used for repeatedly carrying out the method described in Example 30-(3) per mutation point, whereby a plasmid (117) encoding the above-mentioned nitrile hydratase variant was prepared. A competent cell of *Escherichia coli* HB101 (manufactured by Toyobo Co., Ltd.) was transformed with the plasmid to obtain a transformant (117). Moreover, the plasmid was prepared from the above-mentioned fungus body by alkaline SDS extraction, and the base sequence of the nitrile hydratase gene was determined using a DNA sequencer. Then, it was confirmed that the transformant (117) had sequences according to the purpose in which mutation of 79th His in the β-subunit with Asn, mutation of 230th Ala in the β-subunit with Glu and mutation of 231st Ala in the β-subunit with Val were newly added to the plasmid (114) of Example 30-(114).

TABLE 54

| Trans formant No. | Mutation site | Change in amino acid sequence | | Change in base sequence | |
|---|---|---|---|---|---|
| | | Before substi- tution | After substi- tution | Before substi- tution | After substi- tution |
| 115 | α-6th | Leu | Thr | CTG | ACG |
| | α-19th | Ala | Val | GCG | GTG |
| | α-126th | Phe | Tyr | TTC | TAC |
| | β-48th | Leu | Val | CTG | GTG |
| | β-79th | His | Asn | CAC | AAC |
| | β-108th | Glu | Arg | GAG | CGG |
| | β-212th | Ser | Tyr | TCC | TAC |
| | β-230th | Ala | Glu | GCG | GAG |
| | β-231st | Ala | Val | GCC | GTC |
| 116 | α-6th | Leu | Thr | CTG | ACG |
| | α-19th | Ala | Val | GCG | GTG |
| | α-126th | Phe | Tyr | TTC | TAC |
| | β-46th | Met | Lys | ATG | AAG |
| | β-79th | His | Asn | CAC | AAC |
| | β-108th | Glu | Arg | GAG | CGG |
| | β-212th | Ser | Tyr | TCC | TAC |
| | β-230th | Ala | Glu | GCG | GAG |
| | β-231st | Ala | Val | GCC | GTC |
| 117 | α-36th | Thr | Trp | ACG | TGG |
| | β-79th | His | Asn | CAC | AAC |
| | β-176th | Tyr | Cys | TAC | TGC |
| | β-230th | Ala | Glu | GCG | GAG |
| | β-231st | Ala | Val | GCC | GTC |

Evaluation

Each of the transformants 1 to 117 was cultured in the same manner as in the Pth-nitrile hydratase-producing bacteria used in Example 1 to prepare a fungal suspension. 3-mercaptopropionitrile was reacted in the same manner as in Example 29, except that each of the transformants 1 to 117 prepared was used instead of the Pth-nitrile hydratase and as a result, equal to or more than 99% of 3-mercaptopropionitrile was converted to 3-mercaptopropionamide in all cases.

Example 31

1 g of the amidase-producing bacteria shown in Table 55 was respectively added to the reaction solution of 3-mercaptopropionamide obtained in the reaction of Example 30, and reacted for 20 hours. The results are shown in Table 55.

TABLE 55

| | Reaction temperature (° C.) | Conversation rate (%) of 3-mercaptopropionitrile |
|---|---|---|
| Ppu-amidase | 10 | >99 |
| | 20 | >99 |
| | 30 | >99 |
| Pth-amidase | 10 | >99 |
| | 20 | >99 |
| | 30 | >99 |
| Psp-amidase | 10 | 45 |
| | 20 | 30 |
| | 30 | 20 |

Example 32

Reaction by Hydrogen Sulfide-containing 3-mercaptopropionitrile (Pth-amidase)

Hydrogen sulfide gas was blown in 500 g of a 1M sodium phosphate buffer solution (pH 7.0). Since the weight after blowing of the gas was 500.22 g, the hydrogen sulfide concentration of the buffer solution became 440 ppm. The buffer solution was added to 0.5 mL of purified 3-mercaptopropionitrile prepared in Example 1 to have the hydrogen sulfide concentration of from 15 to 180 ppm, thus to give the total amount of 4.5 mL. 0.25 mL of the suspension of Pth-nitrile hydratase-producing bacteria used in Example 1 and 0.25 mL of the suspension of Pth-amidase-producing bacteria were added thereto, and the temperature was kept at 25 degrees centigrade for 6 hours. The results are shown in Table 56.

TABLE 56

| Hydrogen sulfide concentration (ppm) | Reaction yield |
|---|---|
| 0 | 97% |
| 15 | 95% |
| 36 | 80% |
| 180 | 68% |

Example 33

Reaction by 3-mercaptopropionitrile with Hydrogen Sulfide
Subjected to Degassing Treatment (Pth-amidase)

36.12 g of water was added to 144.92 g (1.2 mole) of a 46.42 w/v % sodium hydrogen sulfide solution, and 53.06 g of (1.0 mole) of acrylonitrile was added dropwise thereto over 1 hour while keeping the temperature at 40 degrees centigrade, and then the mixture was aged at 40 degrees centigrade for 10 hours. Subsequently, while the temperature of the reaction mixture was kept at 25 to 30 degrees centigrade, 125.3 g (0.3 mole) of 47 w/v % sulfuric acid was added dropwise thereto over 2 hours to have the pH of from 14 to pH of 6.5 to 7, and then the mixture was aged at 25 to 30 degrees centigrade for 1 hour. The concentration of hydrogen sulfide in the reaction mixture was analyzed by the head-space gas chromatography method. The concentration of hydrogen sulfide in the aged reaction mixture was 8,000 ppm. Hydrogen sulfide in the reaction mixture was removed under reduced pressure until the concentration of hydrogen sulfide in the reaction mixture became 15 ppm (25 to 30 degrees centigrade, 6.7 kPa (50 torr), 3 hours). During dropwise addition of sulfuric acid, during aging, during vacuum degassing, hydrogen sulfide gas discharged out of the reaction system was collected using a caustic trap. Next, 75.6 g of the upper crude 3-mercaptopropionitrile and 270.0 g of the lower aqueous layer were acquired from the 2-layer separated reaction mixture by decantation. The acquired crude 3-mercaptopropionitrile and aqueous layer were used at a weight ratio of 75.6:270. 1 g of the upper crude 3-mercaptopropionitrile and 3.6 g of the lower aqueous layer were weighed, and the pH was adjusted to 7.0 with the use of sulfuric acid and sodium hydroxide to give the total weight of 5.5 g. 1 g of the suspension of Pth-nitrile hydratase-producing bacteria and 1 g of the suspension of Pth-amidase-producing bacteria were added thereto, and the mixture was stirred at 20 degrees centigrade for 24 hours. Equal to or more than 99% of 3-mercaptopropionitrile in the reaction solution was converted to a 3-mercaptopropionic acid.

Example 34

Distilled water was added to the mixture of 3-mercaptopropionitrile, 3-mercaptopropionamide and 3-mercaptopropionic acid obtained in Example 29, and the pH was adjusted to 7.0 with the use of sulfuric acid and sodium hydroxide. 1 g of the suspension of Pth-nitrile hydratase-producing bacteria and 1 g of the suspension of Pth-amidase-producing bacteria were added to 5 g of the reaction solution, and the concentration of 3-mercaptopropionitrile was adjusted to 13 weight %, and the mixture was stirred at 20 degrees centigrade for 24 hours. Equal to or more than 99% of 3-mercaptopropionitrile was converted to a 3-mercaptopropionic acid.

Example 35

An operation was carried in the same manner as in Example 34, except that the Ppu-amidase-producing bacteria was used instead of the Pth-amidase-producing bacteria. Equal to or more than 99% of 3-mercaptopropionitrile was converted to a 3-mercaptopropionic acid.

Example 36

Synthesis of 3,3'-dithiodipropionamide by Enzyme of 3,3'-dithiodipropiononitrile 3.72 g of water was added to 0.43 g (0.0025 mole) of 3,3'-dithiodipropiononitrile and the temperature was adjusted to 20 degrees centigrade. The pH was adjusted to 7.0 using 0.02 g of a 0.02 w/v % NaOH aqueous solution with stirring, and subsequently 0.73 g of water was fed thereto. While the reaction solution with the pH of 7.0 was kept and stirred at 20 degrees centigrade, 0.1 g of the suspension of Pth-nitrile hydratase-producing bacteria was added thereto, and stirred and reacted for 24 hours. The reaction solution was analyzed by HPLC and as a result, it was confirmed that the peak of 3,3'-dithiodipropiononitrile was disappeared, and the peak of 3,3'-dithiodipropionamide was generated. The peak area of the 3,3'-dithiodipropionic acid was 100.0% by HPLC, and equal to or more than 99% of 3,3'-dithiodipropiononitrile was converted to 3,3'-dithiodipropionamide.

Example 37

Synthesis of 3,3'-dithiodipropionic Acid by Enzyme of 3,3'-dithiodipropionamide

While the reaction solution of 3,3'-dithiodipropionamide obtained in Example 36 was stirred at 20 degrees centigrade, 0.6 g of the suspension of Pth-amidase-producing bacteria was added thereto, and reacted at 20 degrees centigrade for 24 hours. The reaction solution was analyzed by HPLC and as a result, it was confirmed that the peak of 3,3'-dithiodipropionamide was disappeared, and the peak of the 3,3'-dithiodipropionic acid was generated. The peak area of the 3,3'-dithiodipropionic acid was 100.0% by HPLC, and equal to or more than 99% of 3,3'-dithiodipropionamide was converted to a 3,3'-dithiodipropionic acid.

Example 38

Synthesis of 3,3'-dithiodipropionic Acid by Enzyme of 3,3'-dithiodipropiononitrile 3.72 g of water was added to 0.43 g (0.0025 mole) of 3,3'-dithiodipropiononitrile and the temperature was adjusted to 30 degrees centigrade. While the slurry liquid was stirred at 30 degrees centigrade, the pH was adjusted to 7.0 using 0.02 g of a 0.02 w/v % NaOH aqueous solution, and subsequently 0.73 g of water was fed thereto. While the slurry liquid with the pH of 7.0 was kept and stirred at 30 degrees centigrade, 0.14 g of the suspension of Pth-nitrile hydratase-producing bacteria was added and subsequently 0.6 g of the suspension of Pth-amidase-producing bacteria was added thereto, and the mixture was reacted at 30 degrees centigrade for 24 hours. The reaction solution was analyzed by HPLC and as a result, it was confirmed that the peak of 3,3'-dithiodipropiononitrile was disappeared, and the peak of the 3,3'-dithiodipropionic acid was generated. The peak area of the 3,3'-dithiodipropionic acid was 100.0% by HPLC, and equal to or more than 99% of 3,3'-dithiodipropiononitrile was converted to a 3,3'-dithiodipropionic acid.

Example 39

Reduction of 3,3'-dithiodipropionic Acid with Zinc Powder 20 g of water was added to 0.526 g (0.0025 mole) of the 3,3'-dithiodipropionic acid prepared in Example 38. 0.67 g of a 32 w/v % NaOH aqueous solution was added thereto. 0.41 g (0.0063 mole) of zinc powder was added to the aqueous solution with stirring at 35 degrees centigrade, 5.58 g of 47 w/v % aqueous sulfuric acid was fed dropwise thereto for 42 minutes, and the mixture was aged at that temperature for 1 hour. The reduced reaction solution was analyzed by HPLC and as a result, it was confirmed that the peak of the 3,3'-dithiodipropionic acid was disappeared, and the peak of the 3-mercaptopropionic acid was generated. The peak area of the 3-mercaptopropionic acid was 100.0% by HPLC, and equal to or more than 99% of the 3,3'-dithiodipropionic acid was converted to a 3-mercaptopropionic acid.

Example 40

Reduction of 3,3'-dithiodipropionic Acid with Iron Powder
The reaction and aging were carried out in the absolutely same manner as in Example 39, except that 0.35 g (0.0063 mole) of iron powder was used instead of zinc powder of Example 39. The reduced reaction solution was analyzed by HPLC and as a result, it was confirmed that the peak of the 3,3'-dithiodipropionic acid was disappeared, and the peak of the 3-mercaptopropionic acid was generated. The peak area of the 3-mercaptopropionic acid was 100.0% by HPLC, and equal to or more than 99% of the 3,3'-dithiodipropionic acid was converted to a 3-mercaptopropionic acid.

Example 41

Synthesis of Pentaerythritol Tetrakis(3-mercaptopropionate)

The reaction was repeatedly carried out in the same manner as in Example 34. 2,000 g of the reaction solution was fed into a 3-liter, 4-necked flask equipped with a stirrer, a condenser tube, a nitrogen gas purge tube, a thermometer and a pH meter, and the system was overheated to 60 degrees centigrade with stirring. 22.6 g of zinc powder was fed to the reaction solution, and the pH was adjusted to equal to or less than 1.0 using 506 g of 47 w/v % aqueous sulfuric acid. The reaction solution was kept at 60 degrees centigrade, aged for 1 hour with stirring, and cooled down to room temperature. While the reaction solution was stirred, and 83.1 g of activated carbon (PMSX) was fed at room temperature over 0.5 hours to adsorb unnecessary fungus component. The mixture treated with activated carbon was filtered and washed with water to remove unnecessary fungus component along with waste activated carbon in the filter cake, whereby a 3-mercaptopropionic acid was obtained from the filtrate. The filtrate was repeatedly extracted and separated with 350 g of n-butyl acetate at 40 degrees centigrade three times, and the butyl acetate layer was combined. The obtained butyl acetate layer was concentrated and subsequently distilled, whereby a 3-mercaptopropionic acid of high purity (equal to or more than 99.9%) was obtained at a yield of 91 (%/acrylonitrile). The method was repeatedly carried out to produce a 3-mercaptopropionic acid.

442.3 g (4.15 mole) of the 3-mercaptopropionic acid obtained by the above method, 136.2 g (1.00 mole) of pentaerythritol, 3.82 g (0.02 mole) of p-toluenesulfonic acid monohydrate, and 185.2 g of toluene were added to a 1-L, 4-necked reaction flask equipped with a stirrer, a reflux condenser with a water separator, a nitrogen gas purge tube and a thermometer. While water by-produced under heat reflux was continuously taken out of the system, the reaction was carried out for 10 hours (internal temperature: 102 to 122 degrees centigrade), and thereafter the system was cooled down to room temperature. The reaction solution was washed with a base and subsequently washed with water, to remove toluene and a very small amount of water under reduced pressure with heating. Thereafter, 463.6 g of pentaerythritol tetrakis(3-mercaptopropionate) was obtained by filtration. The obtained pentaerythritol tetrakis(3-mercaptopropionate) color hue (Yellowness: YI) was 1.0.

Example 42

Production of Plastic Lens 0.014 g (200 ppm relative to the total weight of polymerizable composition) of di-n-butyltin dichloride, 0.084 g of an internal mold release agent (product name: Zelec UN, manufactured by Stepan Co., Ltd.), and 0.035 g of an ultraviolet absorber (product name: Viosorb 583, manufactured by Kyodo Chemical Co., Ltd.) were mixed to 35.4 g of a mixture of 2,5-bis(isocyanatomethyl)-bicyclo[2.2.1]heptane and 2,6-bis(isocyanatomethyl)-bicyclo[2.2.1]heptane at 20 degrees centigrade and dissolved to give a uniform solution. A mixed solution of 16.7 g of pentaerythritol tetrakis(3-mercaptopropionate) and 17.9 g of 4-mercaptomethyl-1,8-dimercapto-3,6-dithaoctane was added to the uniform solution, mixed and dissolved at 20 degrees centigrade. This mixed solution was degassed at 400 Pa for 1 hour, and then filtered using a 1-μm PTFE filter, and injected into a mold composed of a glass mold and a tape. This mold was put into a polymerization oven, elevated temperature slowly from 25 to 120 degrees centigrade over 21 hours for polymerization. After completion of the polymerization, the mold was taken out from the oven, whereby a resin was released from the mold. The obtained resin was additionally annealed at 130 degree centigrade for 4 hours. The obtained resin had transparency. Further, it had a refractive index (ne) of 1.597, Abbe number (ve) of 40.6, heat resistance (Tg) of 118.1 degrees centigrade, and color hue (Yellowness: YI) of 3.8. It was suitable as an optical transparent resin. With respect to the catalyst activity, the viscosity after the polymerizable composition was kept at 20 degrees centigrade for 5 hours was 61 mPa·s.

---

The invention claimed is:

1. A method for producing a carboxylic acid represented by the general formula (2) or a salt thereof from amide represented by the general formula (1) or a salt thereof comprising contacting the amide represented by the general formula (1) or a salt thereof with amidase,

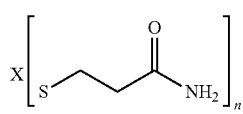  (1)

wherein, in the general formula (1), X represents any of H, S—$C_2H_4$—$CONH_2$, S—$C_2H_4$—COOH and a cation; and n represents 1 when X is H, S—$C_2H_4$—$CONH_2$ or S—$C_2H_4$—COOH, and n represents the same integer as the valence of X when X is a cation,

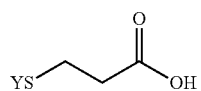  (2)

wherein, in the general formula (2), Y represents any of H and S—$C_2H_4$—COOH, and wherein the amide represented by the general formula (1) or the salt thereof is produced from nitrile represented by the general formula (3) or a salt thereof using nitrite hydratase obtained from a bacterium belonging to the genus *Pseudonocardia*, and the carboxylic acid represented by the general formula (2) or the salt thereof is produced from the amide or the salt thereof,

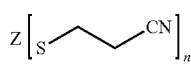  (3)

wherein, in the general formula (3), Z represents any of H, S—$C_2H_4$—CN, S—$C_2H_4$—$CONH_2$ and a cation; and n represents 1 when Z is H or S—$C_2H_4$—$CONH_2$, and n represents the same integer as the valence of Z when Z is a cation.

2. The method according to claim 1, in which the carboxylic acid represented by the general formula (2) or the salt thereof is produced from the nitrile represented by the general formula (3) or the salt thereof in the presence of nitrile hydratase and amidase.

3. The method according to claim 1, in which the concentration of at least one of the amide represented by the general formula (1) or the salt thereof, and the nitrile represented by the general formula (3) or the salt thereof in a reaction solution is equal to or more than 11 weight %.

4. The method according to claim 1, in which the nitrile represented by the general formula (3) or the salt thereof is obtained by reacting acrylonitrile with a compound containing a sulfur atom.

5. The method according to claim 4, in which said compound containing a sulfur atom is sodium hydrogen sulfide.

6. The method according to claim 1, in which said amidase belongs to the amidase signature family.

7. A method for producing pentaerythritol tetrakis(3-mercaptopropionate) comprising:

producing a carboxylic acid represented by the general formula (2) using the method according to claim 1; and carrying out an esterification reaction of said obtained carboxylic acid and pentaerythritol.

8. A method for producing an optical material comprising:

producing pentaerythritol tetrakis(3-mercaptopropionate) using the method according to claim 7; and monopolymerizing or copolymerizing the obtained pentaerythritol tetrakis(3-mercaptopropionate), and then curing it.

9. A method for producing a carboxylic acid represented by the general formula (2) or a salt thereof from amide represented by the general formula (1) or a salt thereof comprising contacting the amide represented by the general formula (1) or a salt thereof with amidase,

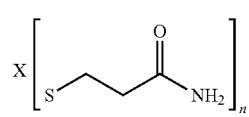  (1)

wherein, in the general formula (1), X represents any of H, S—$C_2H_4$—$CONH_2$, S—$C_2H_4$—COOH and a cation; and n represents 1 when X is H, S—$C_2H_4$—$CONH_2$ or S—$C_2H_4$—COOH, and n represents the same integer as the valence of X when X is a cation,

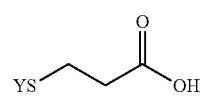  (2)

wherein, in the general formula (2), Y represents any of H and S—$C_2H_4$—COOH and wherein the amide represented by the general formula (1) or the salt thereof is produced from nitrile represented by the general formula (3) or a salt thereof using nitrile hydratase obtained from a bacterium belonging to the genus *Pseudonocardia*, and the carboxylic acid represented by the general formula (2) or the salt thereof is produced from the amide or the salt thereof,

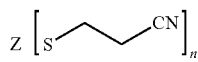 (3)

wherein, in the general formula (3), Z represents any of H, S—$C_2H_4$—CN, S—$C_2H_4$—$CONH_2$ and a cation; and n represents 1 when Z is H or S—$C_2H_4$—$CONH_2$, and n represents the same integer as the valence of Z when Z is a cation, and wherein the nitrile represented by the general formula (3) or the salt thereof is obtained by reacting acrylonitrile with sodium hydrogen sulfide.

10. A method for producing a carboxylic acid represented by the general formula (2) or a salt thereof from amide represented by the general formula (1) or a salt thereof comprising contacting the amide represented by the general formula (1) or a salt thereof with amidase belonging to the amidase signature family,

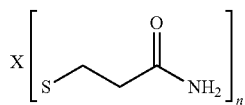 (1)

wherein, in the general formula (1), X represents any of H, S—$C_2H_4$—$CONH_2$, S—$C_2H_4$—COOH and a cation; and n represents 1 when X is H, S—$C_2H_4$—$CONH_2$ or S—$C_2H_4$—COOH, and n represents the same integer as the valence of X when X is a cation,

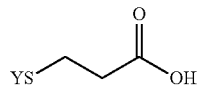 (2)

wherein, in the general formula (2), Y represents any of H and S—$C_2H_4$—COOH.

11. A method for producing pentaerythritol tetrakis(3-mercaptopropionate) comprising:
producing a carboxylic acid represented by the general formula (2); and
carrying out an esterification reaction of said obtained carboxylic acid and pentaerythritol,
wherein the method for producing the carboxylic acid represented by the general formula (2) comprises contacting an amide represented by the general formula (1) or a salt thereof with amidase,

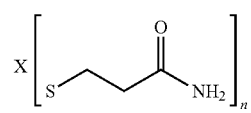 (1)

wherein, in the general formula (1), X represents any of H, S—$C_2H_4$—$CONH_2$, S—$C_2H_4$—COOH and a cation; and n represents 1 when X is H, S—$C_2H_4$—$CONH_2$ or S—$C_2H_4$—COOH, and n represents the same integer as the valence of X when X is a cation,

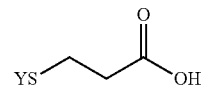 (2)

wherein, in the general formula (2), Y represents any of H and S—$C_2H_4$—COOH.

12. A method for producing an optical material comprising:
producing pentaerythritol tetrakis(3-mercaptopropionate) using the method according to claim 11; and
monopolymerizing or copolymerizing the obtained pentaerythritol tetrakis(3-mercaptopropionate), and then curing it.

* * * * *